(12) United States Patent
Soltero et al.

(10) Patent No.: US 7,166,571 B2
(45) Date of Patent: *Jan. 23, 2007

(54) INSULIN POLYPEPTIDE-OLIGOMER CONJUGATES, PROINSULIN POLYPEPTIDE-OLIGOMER CONJUGATES AND METHODS OF SYNTHESIZING SAME

(75) Inventors: Richard Soltero, Holly Springs, NC (US); Balasingam Radhakrishnan, Chapel Hill, NC (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 420 days.

This patent is subject to a terminal disclaimer.

(21) Appl. No.: 10/382,022

(22) Filed: Mar. 5, 2003

(65) Prior Publication Data

US 2003/0229009 A1 Dec. 11, 2003

Related U.S. Application Data

(63) Continuation-in-part of application No. 10/036,744, filed on Dec. 21, 2001, now Pat. No. 6,913,903.

(60) Provisional application No. 60/318,197, filed on Sep. 7, 2001.

(51) Int. Cl.
  *A61K 38/28* (2006.01)
  *C12P 31/06* (2006.01)
  *C07P 5/00* (2006.01)
  *C07P 7/00* (2006.01)
  *C07P 16/00* (2006.01)
  *C07P 17/00* (2006.01)

(52) U.S. Cl. ............... 514/3; 435/68.1; 530/303

(58) Field of Classification Search ............... None
See application file for complete search history.

(56) References Cited

U.S. PATENT DOCUMENTS

| | | | |
|---|---|---|---|
| 3,256,153 A | 6/1966 | Heimlech |
| 3,868,356 A | 2/1975 | Smyth |
| 3,919,411 A | 11/1975 | Glass et al. |
| 3,950,517 A | 4/1976 | Lindsay et al. |
| 4,003,792 A | 1/1977 | Mill et al. |
| 4,044,196 A | 8/1977 | Huper et al. |
| 4,087,390 A | 5/1978 | Shields |
| 4,093,574 A | 6/1978 | Shields |
| 4,100,117 A | 7/1978 | Shields |
| 4,179,337 A | 12/1979 | Davis et al. |
| 4,229,438 A | 10/1980 | Fujino et al. |
| 4,253,998 A | 3/1981 | Sarantakis |
| 4,277,394 A | 7/1981 | Fujino et al. |
| 4,338,306 A | 7/1982 | Kitao et al. |
| 4,348,387 A | 9/1982 | Brownlee et al. |
| 4,410,547 A | 10/1983 | Ueno et al. |
| 4,469,681 A | 9/1984 | Brownlee et al. |
| 4,472,382 A | 9/1984 | Labrie et al. |
| 4,554,101 A | 11/1985 | Hopp |
| 4,579,730 A | 4/1986 | Kidron et al. |
| 4,585,754 A | 4/1986 | Meisner et al. |
| 4,622,392 A | 11/1986 | Hong et al. |
| 4,684,524 A | 8/1987 | Eckenhoff et al. |
| 4,698,264 A | 10/1987 | Steinke |
| 4,717,566 A | 1/1988 | Eckenhoff et al. |
| 4,744,976 A | 5/1988 | Snipes et al. |
| 4,772,471 A | 9/1988 | Vanlerberghe et al. |
| 4,797,288 A | 1/1989 | Sharma et al. |
| 4,839,341 A | 6/1989 | Massey et al. |
| 4,840,799 A | 6/1989 | Applegren et al. |
| 4,849,405 A | 7/1989 | Ecanow |
| 4,917,888 A | 4/1990 | Katre et al. |

(Continued)

FOREIGN PATENT DOCUMENTS

EP 0 031 567 7/1981

(Continued)

OTHER PUBLICATIONS

A. Guzman & R. Garcia, "Effects of Fatty Ethers and Stearic Acid on the Gastrointestinal Absorption of Insulin," PRHSJ, 9(2): 155-159 (1990).

Abuchowski, A. and F. F. Davis, "Soluble Polymer-Enzyme Adducts," pp. 368-383, Enzymes as Drugs, J. S. Holcenberg, John Wiley, 1981.

Akiyama, M. et al., "The Synthesis of New Derivatives of 1-.beta.-D-Arabinofuranosylcytosine," Chem. Pharm. Bull., 1978, 26(3): p. 981-984.

Allcock et al., "Contemporary Polymer Chemistry," 394-403 (2nd. ed., 1991).

Ansell, S. et al., "Application of Oligo-(14-amino-3,6,9,12-tetraoxatetradecanoic acid) Lipid Conjugates as Steric Barrier Molecules in Liposomal Formulations," Bioconjugate Chem., 10: 353-666 (1999).

(Continued)

*Primary Examiner*—Christopher R Tate
*Assistant Examiner*—Marcela M Cordero Garcia
(74) *Attorney, Agent, or Firm*—Marianne Fuierer; William A. Barrett; Moore & Van Allen PLLC

(57) ABSTRACT

Methods for synthesizing proinsulin polypeptides are described that include contacting a proinsulin polypeptide including an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate. Methods of synthesizing proinsulin polypeptide-oligomer conjugates are also provided as are proinsulin polypeptide-oligomer conjugates. Methods of synthesizing C-peptide polypeptide-oligomer conjugates and other pro-polypeptide-oligomer conjugates are also provided.

132 Claims, 40 Drawing Sheets

U.S. PATENT DOCUMENTS

| | | |
|---|---|---|
| 4,935,246 A | 6/1990 | Ahrens |
| 4,946,828 A | 8/1990 | Markussen |
| 4,957,910 A | 9/1990 | Sutton et al. |
| 4,963,367 A | 10/1990 | Ecanow |
| 4,994,439 A | 2/1991 | Longenecker et al. |
| 5,013,556 A | 5/1991 | Woodle et al. |
| 5,055,300 A | 10/1991 | Gupta |
| 5,055,304 A | 10/1991 | Makino et al. |
| 5,089,261 A | 2/1992 | Nitecki et al. |
| 5,093,198 A | 3/1992 | Speaker et al. |
| 5,157,021 A | 10/1992 | Balschmidt et al. |
| 5,162,430 A | 11/1992 | Rhee et al. |
| 5,164,366 A | 11/1992 | Balschmidt et al. |
| 5,202,415 A | 4/1993 | Jonassen et al. |
| 5,206,219 A | 4/1993 | Desai |
| 5,283,236 A | 2/1994 | Chiou |
| 5,286,637 A | 2/1994 | Veronese et al. |
| 5,292,802 A | 3/1994 | Rhee et al. |
| 5,304,473 A | 4/1994 | Belagaje et al. |
| 5,308,889 A | 5/1994 | Rhee et al. |
| 5,312,808 A | 5/1994 | Shorr et al. |
| 5,324,775 A | 6/1994 | Rhee et al. |
| 5,328,955 A | 7/1994 | Rhee et al. |
| 5,359,030 A | 10/1994 | Ekwuribe |
| 5,405,621 A | 4/1995 | Sipos |
| 5,405,877 A | 4/1995 | Greenwald et al. |
| 5,413,791 A | 5/1995 | Rhee et al. |
| 5,415,872 A | 5/1995 | Sipos |
| 5,438,040 A | 8/1995 | Ekwuribe |
| 5,444,041 A | 8/1995 | Owen et al. |
| 5,446,091 A | 8/1995 | Rhee et al. |
| 5,457,066 A | 10/1995 | Frank et al. |
| 5,461,031 A | 10/1995 | De Felippis |
| 5,468,478 A | 11/1995 | Saifer et al. |
| 5,504,188 A | 4/1996 | Baker et al. |
| 5,506,203 A | 4/1996 | Backstrom et al. |
| 5,518,998 A | 5/1996 | Backstrom et al. |
| 5,523,348 A | 6/1996 | Rhee et al. |
| 5,529,915 A | 6/1996 | Phillips et al. |
| 5,545,618 A | 8/1996 | Buckley et al. |
| 5,550,188 A | 8/1996 | Rhee et al. |
| 5,567,422 A | 10/1996 | Greenwald |
| 5,606,038 A | 2/1997 | Regen |
| 5,612,460 A | 3/1997 | Zalipsky |
| 5,631,347 A | 5/1997 | Baker et al. |
| 5,637,749 A | 6/1997 | Greenwald |
| 5,646,242 A | 7/1997 | Baker et al. |
| 5,650,388 A | 7/1997 | Shorr et al. |
| 5,658,878 A | 8/1997 | Backstrom et al. |
| 5,681,567 A | 10/1997 | Martinez et al. |
| 5,681,811 A | 10/1997 | Ekwuribe |
| 5,693,609 A | 12/1997 | Baker et al. |
| 5,693,769 A | 12/1997 | Kahne et al. |
| 5,700,904 A | 12/1997 | Baker et al. |
| 5,707,648 A | 1/1998 | Yiv |
| 5,738,846 A | 4/1998 | Greenwald et al. |
| 5,747,445 A | 5/1998 | Backstrom et al. |
| 5,747,642 A | 5/1998 | De Felippis |
| 5,750,497 A | 5/1998 | Havelund et al. |
| 5,766,620 A | 6/1998 | Heiber et al. |
| 5,824,638 A | 10/1998 | Burnside et al. |
| 5,830,853 A | 11/1998 | Backstrom et al. |
| 5,830,918 A | 11/1998 | Sportsman et al. |
| 5,849,860 A | 12/1998 | Hakimi et al. |
| 5,853,748 A | 12/1998 | New |
| 5,854,208 A | 12/1998 | Jones et al. |
| 5,856,451 A | 1/1999 | Olsen et al. |
| 5,866,538 A | 2/1999 | Norup et al. |
| 5,874,111 A | 2/1999 | Maitra et al. |
| 5,898,028 A | 4/1999 | Jensen et al. |
| 5,902,588 A | 5/1999 | Greenwald et al. |
| 5,905,140 A | 5/1999 | Hansen |
| 5,907,030 A | 5/1999 | Shen et al. |
| 5,922,675 A | 7/1999 | Baker et al. |
| 5,932,462 A | 8/1999 | Harris et al. |
| 5,942,248 A | 8/1999 | Barnwell |
| 5,948,751 A | 9/1999 | Kimer et al. |
| 5,952,008 A | 9/1999 | Backstrom et al. |
| 5,952,297 A | 9/1999 | De Felippis et al. |
| 5,962,267 A | 10/1999 | Shin et al. |
| 5,968,549 A | 10/1999 | New et al. |
| 5,969,040 A | 10/1999 | Hallahan et al. |
| 5,981,709 A | 11/1999 | Greenwald et al. |
| 5,985,263 A | 11/1999 | Lee et al. |
| 6,004,574 A | 12/1999 | Backstrom et al. |
| 6,025,325 A | 2/2000 | Campfield et al. |
| 6,034,054 A | 3/2000 | DeFelippis et al. |
| 6,043,214 A | 3/2000 | Jensen et al. |
| 6,051,551 A | 4/2000 | Hughes et al. |
| 6,063,761 A | 5/2000 | Jones et al. |
| 6,093,391 A | 7/2000 | Kabanov et al. |
| 6,113,906 A | 9/2000 | Greenwald et al. |
| 6,165,976 A | 12/2000 | Backstrom et al. |
| 6,177,087 B1 | 1/2001 | Greenwald et al. |
| 6,191,105 B1 | 2/2001 | Ekwuribe et al. |
| 6,200,602 B1 | 3/2001 | Watts et al. |
| 6,211,144 B1 | 4/2001 | Havelund |
| 6,248,363 B1 | 6/2001 | Patel et al. |
| 6,251,856 B1 | 6/2001 | Markussen et al. |
| 6,258,377 B1 | 7/2001 | New et al. |
| 6,268,335 B1 | 7/2001 | Brader |
| 6,306,440 B1 | 10/2001 | Backstrom et al. |
| 6,309,633 B1 | 10/2001 | Ekwuribe et al. |
| 6,310,038 B1 | 10/2001 | Havelund |
| 6,323,311 B1 | 11/2001 | Liu et al. |
| 6,335,316 B1 | 1/2002 | Hughes et al. |
| 6,828,297 B1 * | 12/2004 | Ekwuribe et al. ............ 514/3 |
| 6,858,580 B1 * | 2/2005 | Ekwuribe et al. ............ 514/3 |
| 2003/0228652 A1 * | 12/2003 | Radhakrishnan et al. .. 435/68.1 |
| 2003/0229009 A1 * | 12/2003 | Soltero et al. ............ 514/3 |
| 2005/0080001 A1 * | 4/2005 | Soltero et al. ............ 514/3 |
| 2005/0277580 A1 * | 12/2005 | Radhakrishnan et al. ...... 514/3 |

FOREIGN PATENT DOCUMENTS

| | | |
|---|---|---|
| EP | 0 483 465 | 8/1995 |
| EP | 0 597 007 | 10/1996 |
| EP | 0 621 777 | 11/1996 |
| EP | 0 797 615 | 1/1999 |
| GB | 1 492 997 | 11/1997 |
| JP | 1254699 | 10/1989 |
| WO | WO 93/01802 | 2/1993 |
| WO | WO 95/09831 | 4/1995 |
| WO | WO 95/30641 | 11/1995 |
| WO | WO 98/07745 | 2/1998 |
| WO | WO 99/32134 | 7/1999 |
| WO | WO 01/21197 A1 | 3/2001 |

OTHER PUBLICATIONS

Aoshima, M. et al., "N.sup.4 -Behenoyl-1-.beta.-D-Arabinofuranosylcytosine as a Potential New Antitumor Agent," Cancer Research, 1977, 37: pp. 2481-2486.

Baker, D. C. et al., "Prodrugs of 9-.beta.-D-Arabinofuranosyladenine. 1. Synthesis and Evaluation of Some 5'-(O-Acyl) Derivatives," J. Med. Chem., 1978, 21(12): pp. 1218-1221.

Banting et al., "Pancreatic Extracts in the Treatment of Diabetes Mellitus: Preliminary Report," *Can. Med. Assoc. J.*, 145(10): 1281-1286 (1991).

Banting, R. G., et al, "Pancreatic Extracts in the Treatment of Diabetes Mellitus," the Canadian Med. Assoc. J. 1992, 12: 141-146.

Baudys et al., "Stabilization and Intestinal Absorption of Human Calcitonin," J. Contr. Rel. vol. 39, pp. 145-151 (1996).

Baudys, M. et al, "Synthesis and Characterization of Different Glycosylated Derivatives of Insulin" Proceed. Intern. Symp. Cont. Rel. Bioactive. Mater., 1992, 19:210-211.

Boccu, E. et al., "Pharmacokinetic Properties of Polyethylene Glycol Derivatized Superoxide Dismutase," Pharm. Res. Comm., 1982 14: 113-120.

Brange, J. et al, "Chemical Stability of Insulin. 1. Hydrolytic Degradation During Storage of Pharmaceutical Preparations," Pharm. Res., 1992, 9 (6): 715-726.

Brange, J. et al, "Chemical Stability of Insulin. 2. Formation of Higher Molecule Weight Transformation Products During Storage of Pharmaceutical Preparations," Pharm. Res., 1992, 9(6) 727-734.

Chen et al., "Synthesis and Properties of AMA Amphiphiles," J. Org. Chem., 64: 6870-6873 (1999).

Chien, Y. W., Novel Drug Delivery Systems, pp. 678-679, Marcell Deffer, Inc., New York, N.Y., 1992.

Conradi, R.A., et al., "The Influence of Peptide Structure on Transport Across Caco-2 Cells," Pharm. Res., 1991, 8(12): 1453-1459.

Coombes, A.G.A. et al., "Biodegradable Polymeric Microparticles for Drug Delivery and Vaccine Formulation: the Surface Attachment of Hydrophilic Species Using the Concept of Poly(Ethylene Glycol) Anchoring Segments," Biomaterials, 18: 1153-1161 (1997).

Coudert et al., "A Novel, Unequivocal Synthesis of Polyethylene Glycols," Synthetic Communications, 16(1): 19-26 (1986).

D.G. Lindsay & S. Shall, "The Acetylation of Insulin," Biochem. J., 121: 737-745 (1971), Delgado et al.; "The Uses and Properties of PEG-Linked Proteins" Critical Reviews in Therapeutic Drug Carrier Systems 9:3,4 249-304 (1992).

Engel et al.; "Insulin: Intestinal Absorption as Water-in-Oil-in-Water Emulsions" NATURE 219 856-857 (1968).

Fasano, Alessio; "Innovative strategies for the oral delivery of drugs and peptides" TIBTECH 16 152-157 (1988).

Forst et al., "New Aspects on Biological Activity of C-peptide in IDDM Patients," Exp. Clin. Endocrinol. Diabetes, 106: 270-276 (1998).

Francis et al., "Polythelene Glycol Modification: Relevance of Improved Methodology to Tumour Targeting," J. Drug Targeting, 3: 321-340 (1996).

G. Sirokman & G.D. Fasman, "Refolding and proton pumping activity of a polyethylene glycol-bacteriorhodopsin water-soluble conjugate," Protein Science, 2: 1161-1170 (1993).

Gish, D. T. et al., "Nucleic Acids. 11. Synthesis of 5'-Esters of 1-.beta.-D-Arabinofuranosylcytosine Possessing Antileukemic and Immunosuppressive Activity," J. Med. Chem., 1971, 14(12): pp. 1159-1162.

Gombotz et al., "Biodegradable Polymers for Protein and Peptide Drug Delivery," Bioconjugate Chem., 6: 332-351 (1995).

Harris, J. Milton, "Laboratory Synthesis of Polyethylene Glycol Derivatives," J. Macromol. Science - Rev. Macromol. Chem. Phys., C25(3): 325-373 (1985).

Hashimoto et al., "Synthesis of Palmitoyl Derivatives of Insulin and Their Biological Activities," Pharmaceutical Research, 6(2): 171-176 (1989).

Hong, C. I. et al., "Nucleoside Conjugates. 7. Synthesis and Antitumor Activity of 1-.beta.-D-Arabinofuranosylcytosine Conjugates of Ether Lipids," J. Med. Chem., 1986, 29: pp. 2038-2044.

Hostetler, K. Y. et al., "Synthesis and Antiretroviral Activity of Phospholipid Analogs of Azidothymidine and Other Antiviral Nucleosides," The Journal of Biological Chemistry, 1990, 265(11): pp. 6112-6117.

Igarashi, R. et al, "Biologically Active Peptides Conjugated with Lecithin for DDS" Proceed. Intern. Symp. Cont. Rel. Bioactiv. Mater. 1990, 17 367-368.

J. Wei & G.D. Fasman, "A Poly(ethylene glycol) Water-soluble Conjugate of Porin: Refolding to the Native State," Biochemistry, 34:6408-6415 (1995).

Jens Brange, "Galenics of Insulin: The Physico-Chemical and Pharmaceutical Aspects of Insulin and Insulin Preparations," Novo Research Institute, Denmark, 18-100 (1987).

Kemmler et al., "On the Nature and Subcellular Localization of the Proinsulin Converting Enzymes," Federation Proceedings, 30(Abstract 924): 1210Abs (1971).

Kemmler et al., "Studies on the Conversion of Proinsulin to Insulin: I. Converison in Vitro with Trypsin and Carboxypeptidase B." The Journal of Biological Chemistry, 246(22) 6786-6791 (Nov. 25, 1971).

King et al.; "Preparation of Protein Conjugates with Alkoxypolyethylene Glycols" Int. J. Peptide Protein Res. 16 147-155 (1980).

M. Maislos et al, "The Source of the Circulating Aggregate of Insulin in Type I Diabetic Patients is Therapeutic Insulin" J. Clin. Invest., 1986, 77: 717-723.

Mesiha et al., "Hypoglycaemic effect of oral insulin preparations containing Brij 35, 52, 58 or 92 and stearic acid," J. Pharm. Pharmacol., 33: 733-734 (1981).

Neubauer et al., "Influence of Polyethylene Glycol Insulin on Lipid Tissues of Experimental Animals," Diabetes, 32: 953-958 (Oct. 1983).

Nucci, et al. "The Therapeutic Value of Poly(ethylen Glycol)—Modified Proteins" Ac. Drug. Del. Rev. 6: 133-151 1991.

Oka, K. et al, "Enhanced Intestinal Absorption of a Hydrophobic Polymer-conjugated Protein Drug, Smancs, in an Oily Formulation" Pharm. Res., 1990, 7 (8): 852-855.

Patel et al. "Oral Administration of Insulin By Encapsulation Within Liposomes" FEBS Lett. 62(1) 60-63 1976.

Price, JC, Polyethylene Glycol, 355-361.

Ratmer, R. E. et al, "Persistent Cutaneous Insulin Allergy Resulting from High-Molecular Weight Insulin Aggregates," Diabetes, 1990, 39: 728-733.

Robbins, D. C. et al, "Antibodies to Covalent Aggregates of Insulin in Blood of Insulin-Using Diabetic Patients" Diabetes, 1987, 36: 838-841.

Russell-Jones, G. J. "Vitamin B12 Drug Delivery", Proceed. Intern. Symp. Control. Rel. Bioactive. Mater., 1992, 19: 102-103.

Saffran et al. "A Model for the Study of the Oral Administration of Peptide Hormones" Can J Biochem 57 548-553 1979.

Saffran, M. et al, "A New Approach to the Oral Administration of Insulin and Other Peptide Drugs," Science, 1986, 233: 1081-1084.

Santiago, N. et al, "Oral Immunization of Rats with Influenza Virus M Protein (M1) Microspheres," Proceed. Intern. Symp. Cont. Rel. Bioactive. Mater., 1992, 19: 116-117.

Savva et al., "Effect of PEG Homopolymer and Grafted Amphiphilic PEG-Palmityl on the Thermotropic Phase Behavior of 1,2-Dipalmitoyl-SN-Glycero-3-Phosphocholine Bilayer," Journal of Liposome Research, 9(3): 357-365 (1999).

Shen et al., "(C) Means to Enhance Penetration, (3) Enhancement of polypeptide and protein absorption by macromolecular carriers via endocytosis and transcytosis," Advanced Drug Delivery Reviews, 8: 93-113 (1992).

Shichiri et al.; "Enteral Absorption of Water-in-Oil-in-Water Insulin Emulsions in Rabbits" Diabetologia 10 317-321 (1974).

Szleifer, I. et al., "Spontaneous Liposome Formation Induced by Grafted Poly(Ethylene Oxide) Layers: Theoretical Prediction and Experimental Verification," Proceedings of the National Academy of Sciences of the United States of America, 95(3): 1032-1037 (Feb. 3, 1998).

Taniguchi, T. et al, "Synthesis of Acyloyl Lysozyme and Improvement of its Lymphatic Transport Following Small Intestinal Administration in Rats" Proceed. Intern. Symp. Control. Rel. Bioactiv. Mater., 1992, 19: 104-105.

Tyle, Praveen, "Iontophoretic Devices for Drug Delivery," Pharma Research, 3:6 318-326 (1986).

V.P. Torchilin, "Immunoliposomes and PEGylated Immunoliposomes: Possible Use for Targeted Delivery of Imaging Agents," Immunomethods, 4: 244-258 (1994).

Wahren et al., "Role of C-peptide in Human Physiology," Am. J. Physiol. Endocrinol. Metab., 278: E759-E768 (2000).

Zalipsky et al., "Peptide Attachment to Extremities of Liposomal Surface Grafted PEG Chains: Preparation of the Long-Circulating Form of Laminim Pentapeptide, YIGSR," Bioconjugate Chem. 6: 705-708 (1995).

Zalipsky, S. et al., "Attachment of Drugs to Polyethylene Glycols," *Eur. Polym. J.*, 1983, 19(12): pp. 1177-1183.

Chang et al., "Human Insulin Production from a Novel Mini-Proinsulin which Has High Receptor-Binding Activity," *Biochem. J.*, 329 631-635 (1998).

Diers et al., "Yeast Fermentation Processes for Insulin Production," *Bioprocess Technology*, 130 166-176 (1991).

Johnson, Irving S., "Human Insulin from Recombinant DNA Technology," *Science*, 219 632-637 (Feb. 11, 1983).

Mackin, R. B., "Proinsulin: Recent Observations and Controversies," *Cell. Mol. Life Sci.*, 54 696-702 (1998).

Morihara, Kazuyuki, "Enzymatic Semisynthesis of Human Insulin: An Update," *Journal of Molecular Recognition*, 3(5/6) 181-186 (1990).

International Search Report for International Application No. PCT/US02/28428 dated Oct. 15, 2003.

Huang et al. "The Relationship Between the Connecting Peptide of Recombined Single Chain Insulin and its Biological Function" *Science in China* 44(6):593-600 (Dec. 2001).

\* cited by examiner

Primary Structure of Miniproinsulin

Alternative Miniproinsulin

Alternative Miniproinsulin

INSULIN POLYPEPTIDE-OLIGOMER CONJUGATES, PROINSULIN POLYPEPTIDE-OLIGOMER CONJUGATES AND METHODS OF SYNTHESIZING SAME

RELATED APPLICATIONS

This application is a continuation-in-part application of U.S. application Ser. No. 10/036,744, filed Dec. 21, 2001, now U.S. Pat. No. 6,913,903, and which claims the benefit of U.S. provisional application Ser. No. 60/318,197, filed Sep. 7, 2001, the disclosures of each of which are incorporated herein by reference in their entireties.

FIELD OF THE INVENTION

The present invention relates to insulin conjugates, methods of synthesizing such conjugates, and methods of treating diseases including diabetes therewith.

BACKGROUND OF THE INVENTION

The insulin polypeptide is the primary hormone responsible for controlling the transport, utilization and storage of glucose in the body. The β-cells of the pancreatic islets secrete a single chain precursor of insulin, known as proinsulin. Proteolysis of proinsulin results in removal of certain basic amino acids in the proinsulin chain along with the connecting peptide (C-peptide) to yield the biologically active polypeptide insulin.

The insulin molecule has been highly conserved in evolution and generally consists of two chains of amino acids linked by disulfide bonds. In the natural human, two-chain insulin molecule (mw 5,800 Daltons), the A-chain is composed of 21 amino acid residues and has glycine at the amino terminus and the B-chain has 30 amino acid residues and phenylalanine at the amino terminus.

Insulin can exist as a monomer or may aggregate into a dimer or a hexamer formed from three of the dimers. Biological activity, i.e., the ability to bind to receptors and stimulate the biological actions of insulin, resides in the monomer.

Diabetes is a biological disorder involving improper carbohydrate metabolism. Diabetes results from insufficient production of, or reduced sensitivity to, insulin. In persons with diabetes, the normal ability to use glucose is inhibited, leading to elevated blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness.

There are two varieties of diabetes. Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases, administration of insulin is required.

Untreated diabetes leads to ketosis, the accumulation of ketones, which are products of fat breakdown, in the blood. Ketosis is followed by the accumulation of acid in the blood (acidosis), nausea and vomiting. As the toxic products of disordered carbohydrate and fat metabolism continue to build up, the patient goes into a diabetic coma, which leads to death. Before the isolation of insulin in the 1920s, most patients died within a short time after onset.

The use of insulin as a treatment for diabetes dates to 1922, when Banting et al. ("Pancreatic Extracts in the Treatment of Diabetes Mellitus," *Can. Med. Assoc. J.*, 12:141–146 (1922)) showed that the active extract from the pancreas had therapeutic effects in diabetic dogs. In that same year, treatment of a diabetic patient with pancreatic extracts resulted in a dramatic, life-saving clinical improvement.

Until recently, bovine and porcine insulin were used almost exclusively to treat diabetes in humans. Today, however, numerous variations in insulin between species are known. Each variation differs from natural human insulin in having amino acid substitution(s) at one or more positions in the A- and/or B-chain. Despite these differences, most mammalian insulin has comparable biological activity. The advent of recombinant technology has enabled commercial scale manufacture of human insulin (e.g., Humulin™ insulin, commercially available from Eli Lilly and Company, Indianapolis, Ind.) or genetically engineered insulin having biological activity comparable to natural human insulin.

Treatment of diabetes typically requires regular injections of insulin. Due to the inconvenience of insulin injections, massive efforts to improve insulin administration and bioassimilation have been undertaken.

Attempts have been made to deliver insulin by oral administration. The problems associated with oral administration of insulin to achieve euglycemia in diabetic patients are well documented in pharmaceutical and medical literature. Digestive enzymes in the gastrointestinal tract rapidly degrade insulin, resulting in biologically inactive breakdown products. In the stomach, for example, orally administered insulin undergoes enzymatic proteolysis and acidic degradation. Comparable proteolytic breakdown of insulin occurs in the intestine. In the lumen, insulin is attacked by a variety of enzymes including gastric and pancreatic enzymes, exo- and endopeptidases, and brush border peptidases. Even if insulin survives this enzymatic attack, the biological barriers that must be traversed before insulin can reach its receptors in vivo can limit its bioavailability after oral administration of insulin. For example, insulin can possess low membrane permeability, limiting its ability to pass from the intestinal lumen into the bloodstream.

Some efforts to provide an oral form of insulin have focused on providing insulin-oligomer conjugates. Human insulin and many closely related insulins that are used therapeutically contain three amino acid residues bearing free primary amino groups. All three primary amino groups, namely the N-termini (alpha amino groups) of the A and B chains ($Gly^{A1}$ and $Phe^{B1}$) and the epsilon-amino group of $Lys^{B29}$, can be modified by conjugation with oligomers. Depending on the reaction conditions, N-acylation of an unprotected insulin leads to a complex mixture of mono-, di-, and tri-conjugates (e.g., insulin mono-conjugated at $Gly^{A1}$, insulin mono-conjugated at $Phe^{B1}$, insulin mono-conjugated at $Lys^{B29}$, insulin di-conjugated at $Gly^{A1}$ and $Phe^{B1}$, insulin di-conjugated at $Gly^{A1}$ and $Lys^{B29}$, insulin di-conjugated at $Phe^{B1}$ and $Lys^{B29}$, and insulin tri-conjugated at $Gly^{A1}$, $Phe^{B1}$, and $Lys^{B29}$). When a particular conjugate, for example insulin mono-conjugated at $Lys^{B29}$, is desired, it can be burdensome and/or expensive to separate (or purify) such a complex mixture of conjugates to obtain the desired conjugate.

As a result, various efforts have been undertaken to selectively synthesize the desired insulin conjugate. For example, Muranishi and Kiso, in Japanese Patent Application 1-254,699, propose a five-step synthesis for preparing fatty acid insulin derivatives. The A1- and B1-amino groups of insulin are protected (or blocked) with p-methoxybenzoxy carbonyl azide (pMZ). After acylation with a fatty acid ester, the protection (blocking) groups are removed to provide insulin mono-acylated at Lys(B29) with a fatty acid. As another example, U.S. Pat. No. 5,750,497 to Havelund et al. proposes treating human insulin with a Boc-reagent (e.g. di-tert-butyl dicarbonate) to form (A1,B1)-diBoc human insulin, i.e., human insulin in which the N-terminal end of both the A- and B-chains are protected by a Boc-group. After an optional purification, e.g., by HPLC, a lipophilic acyl group is introduced in the ε-amino group of $Lys^{B29}$ by allowing the product to react with a N-hydroxysuccinimide ester of the formula X-OSu wherein X is the lipophilic acyl group to be introduced. In the final step, trifluoroacetic acid is used to remove the Boc-groups and the product, $N^{\epsilon B29}$-X human insulin, is isolated.

Various other efforts have been undertaken to preferentially synthesize the desired insulin conjugate to provide a mixture of conjugates in which the desired insulin conjugate is the preferred product. For example, U.S. Pat. No. 5,646,242 to Baker et al. proposes a reaction that is performed without the use of amino-protecting groups. Baker proposes the reaction of an activated fatty ester with the ε-amino group of insulin under basic conditions in a polar solvent. The acylation of the ε-amino group is dependent on the basicity of the reaction. At a pH greater than 9.0, the reaction preferentially acylates the ε-amino group of B29-lysine over the α-amino groups. Examples 1 through 4 report reaction yields of the mono-conjugated insulin as a percentage of the initial amount of insulin between 67.1% and 75.5%. In Example 5, Baker also proposes acylation of human proinsulin with N-succinimidyl palmitate. The exact ratios of ε-amino acylated species to α-amino acylated species were not calculated. The sum of all ε-amino acylated species within the chromatogram accounted for 87–90% of the total area, while the sum of all related substances (which would presumably include any α-amino acylated species) accounted for <7% of the total area, for any given point in time.

The present invention overcomes previous limitations in the art by providing methods of site-specifically synthesizing particular insulin-oligomer conjugates that are less burdensome and/or more cost effective than conventional methods.

SUMMARY OF THE INVENTION

When compared to the conventional schemes described above, embodiments of the present invention provide a commercially less expensive and/or higher yielding manufacturing scheme for producing insulin-oligomer conjugates where site-specific conjugation is desirable (e.g., where it is desirable to provide an insulin mono-conjugate having the oligomer coupled to the B-29 Lys of the insulin molecule). Unlike conventional schemes, which propose selective conjugation of insulin by blocking the N-termini of the insulin with compounds such as p-methoxybenzoxy carbonyl azide (Muranishi and Kiso) or by attempting to control the reaction conditions to reduce but not eliminate conjugation at the N-termini of the insulin (Baker), embodiments of the present invention couple the oligomer to the B-29 Lys of proinsulin or of artificial proinsulin (e.g., proinsulin coupled at the N-terminus of its B-chain to a leader peptide) or of single chain insulin precursor (SCIP) in which the carboxy terminus of the B-chain is joined by an amide bond to the amino terminus of the A-chain. The C-peptide present and leader peptide (if present) is then cleaved from the proinsulin-oligomer conjugate to provide insulin mono-conjugated at B-29 Lys with the oligomer. Embodiments of the present invention can provide high site specificity for B-29 Lys modification. Methods according to embodiments of the present invention utilizing proinsulin polypeptides can provide high conversion B-29 modified product, for example with yields as high as 80% or greater, compared with that obtained via conventional insulin pathways.

According to certain embodiments, the invention provides a method of synthesizing an insulin polypeptide-oligomer conjugate that includes contacting a proinsulin polypeptide, comprising an insulin polypeptide coupled to one or more peptides by peptide bond(s) capable of being cleaved to yield the insulin polypeptide, with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate.

According to other embodiments, the invention provides a method of synthesizing an insulin polypeptide-acyl oligomer conjugate, comprising enzymatically cleaving one or more peptides from a proinsulin polypeptide-acyl oligomer conjugate to provide the insulin polypeptide-acyl oligomer conjugate.

According to other embodiments of the present invention, a method of synthesizing a proinsulin polypeptide-oligomer conjugate is provided that includes contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide the proinsulin polypeptide-oligomer conjugate.

According to still other embodiments, the invention provides, a proinsulin polypeptide-oligomer conjugate that includes a proinsulin polypeptide including an insulin polypeptide, and an oligomer coupled to the insulin polypeptide portion of the proinsulin polypeptide.

According to yet other embodiments, the invention provides a method of synthesizing a C-peptide polypeptide-oligomer conjugate. The method generally comprises contacting a pro-C-peptide polypeptide comprising a C-peptide polypeptide coupled to one or more peptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate, and cleaving the one or more peptides from the pro-C-peptide polypeptide-oligomer conjugate to provide the C-peptide polypeptide-oligomer conjugate.

DETAILED DESCRIPTION OF THE INVENTION

Figure 1:
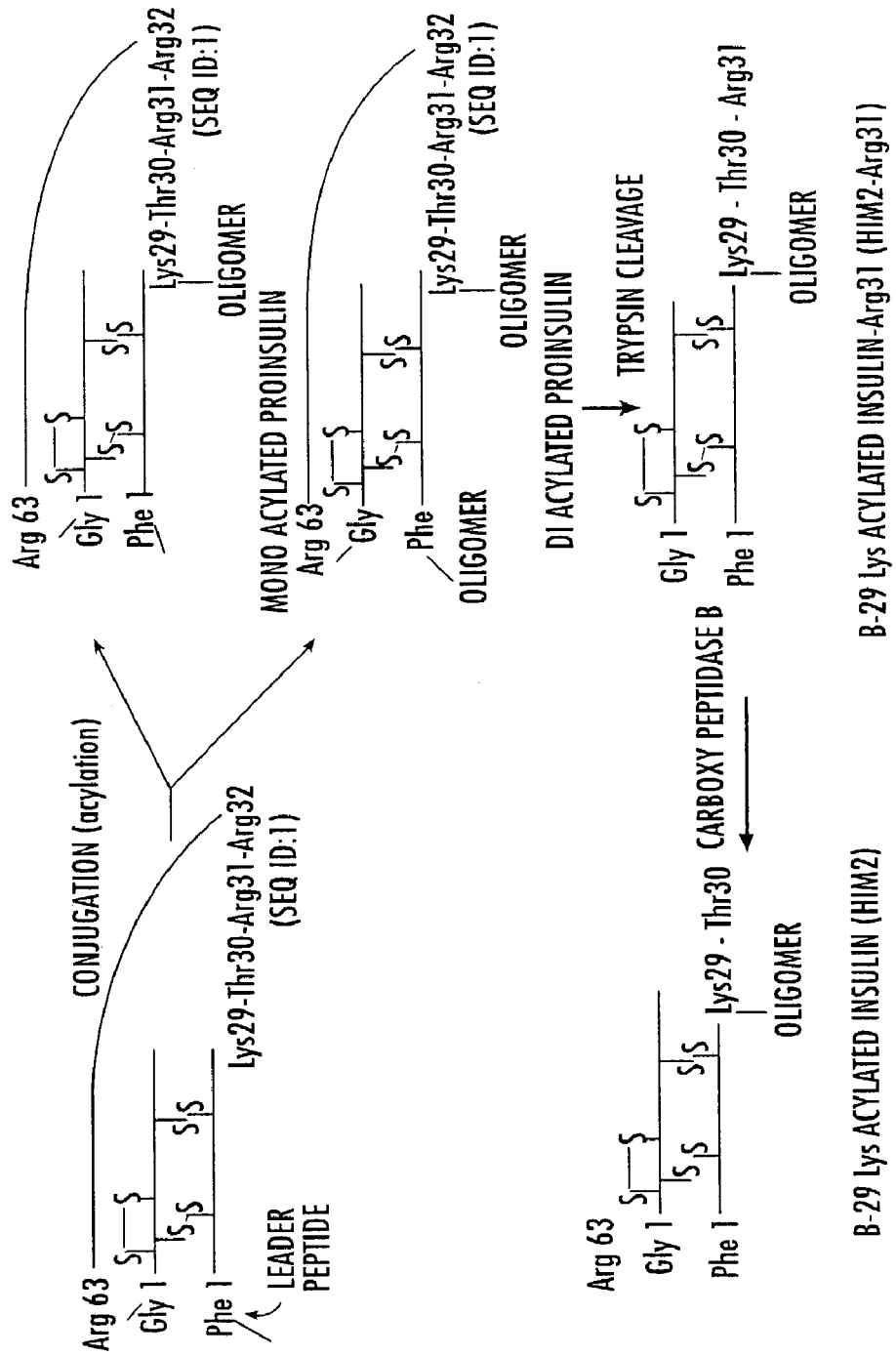
FIG. 1 illustrates embodiments of a synthesis route for preparation of B-29 Lys modified insulin using a proinsulin having a leader peptide.

The present invention now will be described more fully hereinafter with reference to the accompanying drawings, in which various embodiments of the invention are shown. This invention can, however, be embodied in many different forms and should not be construed as limited to the embodiments set forth herein; rather, these embodiments are provided so that this disclosure will be thorough and complete, and will fully convey the scope of the invention to those skilled in the art.

All amino acid abbreviations used in this disclosure are those accepted by the United States Patent and Trademark Office as set forth in 37 C.F.R. § 1.822(b).

As used herein, the term "between" when used to describe various ranges should be interpreted to include the endpoints of the described ranges.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "insulin polypeptide" means a polypeptide possessing at least some of the biological activity of insulin (e.g., ability to affect the body through insulin's primary mechanism of action). For example, an insulin polypeptide can be a polypeptide such as insulin having an A-chain polypeptide and a B-chain polypeptide coupled to the A-chain polypeptide by disulfide bonds. In various embodiments of the present invention, the insulin polypeptide can possess a majority of the biological activity of insulin, and can possess substantially all of the biological activity of insulin, and in some embodiments, possesses all of the biological activity of insulin. In certain embodiments of this invention, an insulin polypeptide can possess enhanced biological activity of insulin. Enhanced activity relative to insulin is present, for example, when administration produces a glucose lowering effect that is greater than the glucose lowering effect of a corresponding amount of insulin.

As used herein, the term "proinsulin polypeptide" means an insulin polypeptide that is coupled to one or more non-insulin polypeptides (e.g., leader peptides and/or connecting or C-peptides) by peptide bond(s) that are capable of cleavage in vitro or in vivo. For example, a proinsulin polypeptide can include an insulin polypeptide, such as insulin, having an A-chain polypeptide coupled to a B-chain polypeptide by bonds such as disulfide bonds, and a connecting peptide coupled to the C-terminus of the B-chain polypeptide and coupled to the N-terminus of the A-chain polypeptide by peptide bonds that are capable of cleavage in vitro and/or in vivo. As another example, a proinsulin polypeptide can include an insulin polypeptide, such as insulin, having an A-chain polypeptide coupled to a B-chain polypeptide by bonds such as disulfide bonds, a connecting peptide coupled to the C-terminus of the B-chain polypeptide and coupled to the N-terminus of the A-chain polypeptide by peptide bonds that are capable of cleavage in vitro and/or in vivo, and a leader peptide coupled to the N-terminus of the B-chain polypeptide. Exemplary proinsulin polypeptides include, but are not limited to, proinsulin, proinsulin analogs, proinsulin fragments, proinsulin analog fragments, or any of proinsulin, proinsulin analogs, proinsulin fragments, proinsulin analog fragments having a leader peptide; preproinsulin, preproinsulin analogs, preproinsulin fragments, preproinsulin fragment analogs, miniproinsulin, and fusion proteins.

As used herein, the term "insulin" includes, but is not limited to, the insulin of any one or more of the following species: human, cow, pig, sheep, horse, dog, chicken, duck or whale, as well as any other species now known or later identified to produce insulin. The insulin of this invention can be provided by natural, synthetic, or genetically engineered (e.g., recombinant) sources. In various embodiments of the present invention, insulin can be human insulin.

As used herein, "single chain insulin precursor" of "SCIP" includes an insulin polypeptide precursor that lacks a C-peptide. The SCIP can have an A-chain polypeptide and a B-chain polypeptide, where the N- or C-terminus of the A-chain is coupled to the C- or N-terminus of the B-chain by a connecting peptide having between a lower limit of −10, −9, −8, −7, −6, −5, −4, −3, −2, −1, 0, 1, 2, 3, 4, 5, 6, 7, 8, or 9 and an upper limit of 0, 1, 2, 3, 4, 5, 6, 7, 8, 9, or 10 amino acid residues. The SCIP can also include a leader sequence.

As used herein, the term "insulin analog" includes insulin wherein one or more of the amino acids have been replaced while retaining some or all of the activity of the insulin. The analog is described by noting the replacement amino acids with the position of the replacement as a superscript followed by a description of the insulin. For example, "Pro$^{B29}$ insulin, human" means that the lysine typically found at the B29 position of a human insulin molecule has been replaced with proline. An insulin analog of this invention can also include an insulin polypeptide having more amino acids than the number of amino acids present in native insulin. Examples of such analogs can include, but are not limited to, insulin-Arg$^{B31}$ (as produced as described in Example 14 herein, after trypsin cleavage of the C-peptide from the proinsulin, but before the carboxypeptidase cleavage), insulin-Arg$^{A0}$, which would result from undercleavage of a leader peptide from the A-chain, and insulin-Xaa$^{B0}$, wherein Xaa is any amino acid, which could result, for example, from the use of a non-native C-peptide that was under-cleaved. An insulin analog of this invention also includes an insulin polypeptide having fewer amino acids than the number of amino acids present in native insulin due to deletion of amino acids and/or an insulin polypeptide having more than the number of amino acids present in native insulin due to insertion of additional amino acids into the amino acid chain of the insulin polypeptide. Insulin analogs of this invention can also include any combination of the insulin analogs described for this invention Insulin analogs can be obtained by various means, as will be understood by those skilled in the art. For example, certain amino acids can be substituted for other amino acids in the insulin structure without appreciable loss of interactive binding capacity with structures such as, for example, antigen-binding regions of antibodies or binding sites on substrate molecules. As the interactive capacity and nature of insulin defines its biological functional activity, certain amino acid sequence substitutions can be made in the amino acid sequence and nevertheless remain a polypeptide with like properties.

In making such substitutions, the hydropathic index of amino acids can be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids can be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±11 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporated herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions/insertions are generally therefore based on the relative similarity of the amino acid side-chain substituents, for example, their hydrophobicity, hydrophilicity, charge, size, and the like. Exemplary substitutions (i.e., amino acids that can be interchanged without significantly altering the biological activity of the polypeptide) that take various of the foregoing characteristics into consideration are well known to those of skill in the art and include, for example arginine and lysine; glutamate and aspartate; serine and threonine; glutamine and asparagine; and valine, leucine and isoleucine.

As will be understood by those skilled in the art, insulin analogs can be prepared by a variety of recognized peptide synthesis techniques including, but not limited to, classical (solution) methods, solid phase methods, semi-synthetic methods, and recombinant DNA methods.

Examples of human insulin analogs include, but are not limited to, $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; $Ala^{B28}$ $Pro^{B29}$ insulin, human, as well as any other insulin analog now known or later identified. An insulin analog of this invention can also comprise an insulin molecule comprising a B-chain with additional lysines added As used herein, the term "insulin fragment" includes a segment of the amino acid sequence found in the insulin that retains some or all of the activity of the insulin. Insulin fragments are denoted by stating the position(s) in an amino acid sequence followed by a description of the amino acid. For example, a "B25–B30 human insulin" fragment would be the six amino acid sequence corresponding to the B25, B26, B27, B28, B29 and B30 positions in the human insulin amino acid sequence.

As used herein, the term "insulin fragment analog" includes a segment of the amino acid sequence found in the insulin molecule wherein one or more of the amino acids in the segment have been replaced, inserted and/or deleted, and/or one or more exogenous amino acids have been inserted, while retaining some or all of the activity of the insulin.

As used herein, the term "proinsulin" includes the proinsulin of any one or more of the following species: human, cow, pig, sheep, horse, dog, chicken, duck or whale, as well as any other species now known or later identified to produce proinsulin. The proinsulin of this invention can be provided by natural, synthetic, or genetically engineered sources. In general, proinsulin comprises insulin having a C-peptide connecting the N-terminus of the A chain of the insulin to the C-terminus of the B chain of the insulin. In various embodiments of the present invention described herein, the proinsulin can be human proinsulin.

As used herein, the term "proinsulin analog" includes proinsulin wherein one or more of the amino acids in proinsulin have been replaced, inserted and/or deleted and/or one or more exogenous amino acids have been inserted, as described above with respect to insulin analogs while retaining some or all of the activity of the insulin portion of the proinsulin. Proinsulin analogs with replacements are described by noting the replacement amino acids with the position of the replacement as a superscript followed by a description of the proinsulin. For example, "$Pro^{B29}$ proinsulin, human" means that the lysine typically found at the B29 position of a human proinsulin molecule has been replaced with proline.

As used herein, the term "proinsulin fragment" includes a segment of the amino acid sequence found in the proinsulin that retains some or all of the biological activity of the insulin, insulin analog or insulin fragment portion of the proinsulin fragment. Proinsulin fragments are denoted by stating the position(s) in an amino acid sequence followed by a description of the amino acid. For example, a "B25–B35 human proinsulin" fragment would be the eleven amino acid sequence corresponding to the B25, B26, B27, B28, B29, B30, B31, B32, B33, B34 and B35 positions in the human proinsulin amino acid sequence.

As used herein, the term "proinsulin fragment analog" includes a segment of the amino acid sequence found in a proinsulin molecule wherein one or more of the amino acids in the segment have been replaced, inserted and/or deleted, and/or one or more exogenous amino acids have been inserted, as described above with reference to insulin analogs while retaining some or all of the activity of the insulin, insulin analog, insulin fragment, or insulin fragment analog portion of the proinsulin fragment.

As used herein, the term "preproinsulin" includes the preproinsulin of any one or more of the following species: human, cow, pig, sheep, horse, dog, chicken, duck or whale, as well as any other species now known or later identified to produce preproinsulin. The preproinsulin of this invention can be provided by natural, synthetic, or genetically engineered sources. In general, preproinsulin is a single chain polypeptide (e.g., a polypeptide having a leader peptide coupled to the N-terminus of the B-chain of the insulin and having the C-terminus of the B-chain coupled to the N-terminus of the A-chain by a connecting peptide) in which the A-chain is coupled to the B-chain by, for example, disulfide bonds. In various embodiments of the present invention described herein, the preproinsulin can be human preproinsulin.

As used herein, the term "preproinsulin analog" includes preproinsulin wherein one or more of the amino acids in preproinsulin have been replaced, inserted and/or deleted, and/or one or more exogenous amino acids have been inserted, as described above with respect to insulin analogs while retaining some or all of the activity of the insulin or insulin analog portion of the preproinsulin analog. An analog with replacements is described by noting the replacement amino acids with the position of the replacement as a superscript followed by a description of the insulin.

As used herein, the term "preproinsulin fragment" includes a segment of the amino acid sequence found in preproinsulin that retains some or all of the biological activity of the insulin or insulin fragment portion of the preproinsulin fragment. Preproinsulin fragments are denoted by stating the position(s) in an amino acid sequence followed by a description of the amino acid.

As used herein, the term "preproinsulin fragment analog" includes a segment of the amino acid sequence found in preproinsulin molecule wherein one or more of the amino acids in the segment have been replaced, inserted and/or deleted, and/or one or more exogenous amino acids have been inserted, as described above with reference to insulin analogs while retaining some or all of the activity of the insulin, insulin analog, insulin fragment or insulin fragment analog portion of the preproinsulin fragment analog.

As used herein, the term "miniproinsulin" refers to a single-chain insulin propolypeptide having an A-chain polypeptide and a B-chain polypeptide, where the N- or C-terminus of the A-chain is coupled to the C- or N-terminus of the B-chain by a connecting peptide having between a lower limit of −10, −9, −8, −7, −6, −5, −4, −3, −2, −1, 0, 1, 2, 3, 4, 5, 6, 7, 8, or 9 and an upper limit of 0, 1, 2, 3, 4, 5, 6, 7, 8, 9, or 10 amino acid residues, and wherein the A-chain polypeptide is coupled to the B-chain polypeptide by bonds, such as disulfide bonds. Miniproinsulins can be various miniproinsulins as will be understood by those skilled in the art including, but not limited to, those described in U.S. Pat. No. 5,157,021 to Balschmidt et al. and U.S. Pat. No. 5,202,415 to Jonassen et al., the disclosures of each of which are incorporated by reference herein in their entireties.

As used herein, the term "C-peptide" means a peptide having the amino acid sequence of the C-peptide of the proinsulin of one of the following species: human, monkey, cow, pig, sheep, horse, dog, chicken, duck or whale, provided by natural, synthetic, or genetically engineered sources. In various embodiments of the present invention described herein, the C-peptide can be human C-peptide.

As used herein, the term "C-peptide analog" means a C-peptide wherein one or more of the amino acids in the C-peptide have been replaced, inserted and/or deleted, and/or one or more exogenous amino acids have been inserted, as described above with respect to insulin analogs while retaining some or all of the biological activity of the C-peptide. The C-peptide analog can comprise the pentapeptide segment at the C-terminus of a C-peptide and/or the nonapeptide segment found at positions 11–19 of a C-peptide. When the C-peptide analog comprises the pentapeptide segment, the pentapeptide segment can be at the C-terminus of the C-peptide analog. In some embodiments, the C-peptide analog comprises the tetrapeptide segment at the C-terminus of a C-peptide and/or the nonapeptide segment found at positions 11–19 of a C-peptide. When the C-peptide analog comprises the tetrapeptide segment, the tetrapeptide segment can be at the C-terminus of the C-peptide analog. The nonapeptide segment found at positions 11–19 of a C-peptide as described above can be the nonapeptide segment found at positions 11–19 of human C-peptide.

As used herein, the term "C-peptide fragment" means a segment of the amino acid sequence of C-peptide that retains some, substantially all, or all of the biological activity of the C-peptide. The C-peptide fragment can comprise the pentapeptide segment at the C-terminus of a C-peptide and/or the nonapeptide segment found at positions 11–19 of a C-peptide. When the C-peptide fragment comprises the pentapeptide segment, the pentapeptide segment can be at the C-terminus of the C-peptide fragment. The C-peptide fragment can also comprise the tetrapeptide segment at the C-terminus of a C-peptide and/or the nonapeptide segment found at positions 11–19 of a C-peptide. When the C-peptide fragment comprises the tetrapeptide segment, the tetrapeptide segment can be at the C-terminus of the C-peptide fragment. In certain embodiments, the C-peptide fragment consists of a peptide selected from the group consisting of the pentapeptide segment of the C-terminus of a C-peptide, the nonapeptide segment found at positions 11–19 of a C-peptide, and the tetrapeptide segment of the C-terminus of a C-peptide. The nonapeptide segment found at positions 11–19 of a C-peptide described above can be the nonapeptide segment found at positions 11–19 of human C-peptide.

As used herein, the term "C-peptide fragment analog" means a segment of the amino acid sequence of C-peptide wherein one or more of the amino acids in the segment have been replaced, inserted and/or deleted, and/or one or more exogenous amino acids have been inserted, as described above with reference to insulin analogs while retaining some, substantially all, or all of the biological activity of the insulin. The C-peptide fragment analog can comprise the pentapeptide segment at the C-terminus of a C-peptide and/or the nonapeptide segment found at positions 11–19 of a C-peptide. When the C-peptide fragment analog comprises the pentapeptide segment, the pentapeptide segment can be at the C-terminus of the C-peptide fragment analog. In some embodiments, the C-peptide fragment analog comprises the tetrapeptide segment at the C-terminus of a C-peptide and/or the nonapeptide segment found at positions 11–19 of a C-peptide. When the C-peptide fragment analog comprises the tetrapeptide segment, the tetrapeptide segment can be at the C-terminus of the C-peptide fragment analog. The nonapeptide segment found at positions 11–19 of a C-peptide described above can be the nonapeptide segment found at positions 11–19 of human C-peptide.

As used herein, the term "C-peptide polypeptide" means a polypeptide having a therapeutic utility and biological activity similar to the therapeutic utility and biological functionality for C-peptides and/or C-peptide fragments described in Wahren et al., "Role of C-peptide in Human Physiology," *Am. J. Physiol. Endocrinol. Metab.*, 278: E759–E768 (2000) and/or Forst et al., "New Aspects on Biological Activity of C-peptide in IDDM Patients," *Exp. Clin. Endocrinol. Diabetes*, 106: 270–276 (1998), the disclosures of which are incorporated herein by reference in their entireties. For example, C-peptide polypeptides have therapeutic utility that includes, but is not limited to, decreased glomerular hyperfiltration, augmented whole body and/or skeletal muscle glucose utilization, improved autonomic nerve function, and/or a redistribution of microvascular skin blood flow. C-peptide polypeptides have biological activity that includes, but is not limited to, the ability to stimulate $Na^+$-$K^+$-ATPase activity, the ability to stimulate endothelial nitric oxide synthase activity, and/or the ability to bind specifically to cell surfaces (e.g., at a G-protein-coupled surface receptor) with subsequent activation of $Ca^{2+}$-dependent intracellular signaling pathways. C-peptide polypeptides can have an association rate constant for binding to endothelial cells, renal tubular cells, and fibroblasts of $\sim 3 \times 10^9$ $M^{-1}$. C-peptide polypeptides can be C-peptides, C-peptide analogs, C-peptide fragments, or C-peptide fragment analogs.

As used herein, the term "pro-C-peptide polypeptide" means a C-peptide polypeptide coupled to one or more peptides that are cleavable to provide the C-peptide polypeptide.

As used herein, the term "A-chain polypeptide" means a polypeptide that is substantially biologically equivalent to the A-chain of an insulin molecule. For example, A-chain polypeptides can be A-chain analogs, as described above with respect to insulin analogs, A-chain fragments, or A-chain analog fragments.

As used herein, the term "B-chain polypeptide" means a polypeptide that is substantially biologically equivalent to the B-chain of an insulin molecule. For example, B-chain polypeptides can be B-chain analogs, as described above with respect to insulin analogs, B-chain fragments, or B-chain analog fragments.

As used herein, the term "peptide or polypeptide" means an amino acid sequence of at least amino acid residues.

As used herein, the term "amphiphilically balanced" means capable of substantially dissolving in water and capable of penetrating biological membranes.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—CH$_2$—CH$_2$—O—.

As used herein, the term "lipophilic" means the ability to dissolve in lipids and/or the ability to penetrate, interact with and/or traverse biological membranes, and the term "lipophilic moiety" or "lipophilic" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

The present invention also provides methods of synthesizing an insulin polypeptide-oligomer conjugate that include contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate. For example, insulin-oligomer conjugates can be synthesized as described in the Examples provided below. An embodiment of a synthesis route is provided in FIG. 1.

The proinsulin polypeptide can be various proinsulin polypeptides comprising an insulin polypeptide coupled to one or more peptides by peptide bond(s) capable of being cleaved to yield the insulin polypeptide as will be understood by those skilled in the art including, but not limited to, proinsulin, proinsulin analogs, proinsulin fragments, proinsulin fragment analogs, miniproinsulin, SCIP, or fusion proteins. In some embodiments, the proinsulin polypeptide is a proinsulin analog having a leader peptide. The proinsulin analog having a leader peptide is available, for example, from Itoham Foods, Inc. of Ibaraki Pref, Japan. The leader peptide and the C-peptide of the proinsulin analog are each devoid of lysine residues. In other embodiments, the proinsulin polypeptide is a proinsulin polypeptide that is available for example, from Biobras of Belo Horizonte, Brazil. The proinsulin polypeptide has a leader peptide coupled to the N-terminus of the B-chain of the proinsulin. The leader peptide is devoid of lysine residues.

The insulin polypeptide can have an A-chain polypeptide and a B-chain polypeptide. The A-chain polypeptide can be devoid of lysine residues. The B-chain polypeptide can comprise a single lysine residue. The A-chain polypeptide and the B-chain polypeptide can be cross-linked, and can be cross-linked using one or more disulfide bonds. In some embodiments, the A-chain polypeptide and the B-chain polypeptide each comprise cysteine residues, one or more of which are coupled using one or more disulfide bonds to cross-link the A-chain polypeptide with the B-chain polypeptide. The insulin polypeptide can be insulin, an insulin analog, an insulin fragment, or an insulin analog fragment.

In some embodiments, the one or more peptides coupled to the insulin polypeptide comprise a connecting peptide coupled at a first end to the C-terminus of the B-chain polypeptide and at a second end to the N-terminus of the A-chain polypeptide. In general, the amino acid sequence of the connecting peptide is not critical and the connecting peptide can be various connecting peptides as will be understood by those skilled in the art including, but not limited to, C-peptide polypeptides, C-peptides, and the connecting peptides in miniproinsulins. In some embodiments, the connecting peptide is devoid of lysine residues. These embodiments can utilize less oligomeric reagents by reducing the number of possible conjugation sites on the proinsulin polypeptide molecule.

In other embodiments, the one or more peptides coupled to the insulin polypeptide comprise a leader peptide that is coupled to the N-terminus of the B-chain polypeptide. In general, the amino acid sequence of the leader peptide is not critical. In some embodiments, the leader peptide is devoid of lysine residues. These embodiments can reduce the amount of oligomeric reagent used by limiting the number of conjugation sites on the proinsulin polypeptide molecule.

In still other embodiments, the one or more peptides coupled to the insulin polypeptide comprise both a connecting peptide as described above and a leader peptide as described above. The one or more peptides can consist essentially of a connecting peptide and a leader peptide, or can consist of a connecting peptide and a leader peptide.

The peptide bonds are bonds that can be cleaved in various ways as will be understood by those skilled in the art. The peptide bonds can be bonds that can be enzymatically cleaved by enzymes including, but not limited to, trypsin, carboxy peptidase B, thrombin, pepsin, and chymotrypsin. Peptide bonds that can be enzymatically cleaved will be understood by those skilled in the art and include, but are not limited to, Arg—Arg, Thr-Arg, Ala-Arg, Thr-Arg-Arg, Thr-Lys, Arg-Gly, and Arg-Phe.

The oligomer can be various oligomers as will be understood by those skilled in the art. In general, the oligomer can be any oligomer capable of being coupled to a polypeptide as will be understood by those skilled in the art. For example, the oligomer can be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al., the disclosures of each of which are incorporated herein by reference in their entireties. As another example, the oligomer can be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same," the disclosures of each of which are incorporated herein in their entireties.

In some embodiments, the oligomer comprises, consists essentially of, or consists of, a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety can be a polyalkylene glycol moiety. The polyalkylene glycol moiety has at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits, and/or between a lower limit of 3, 4, 5, or 6 and an upper limit of 5, 6, 7, 8, 9, 10, 11, or 12 polyalkylene glycol subunits. In some embodiments, the polyalkylene glycol moiety can have between a lower limit of 4, 5, or 6 and an upper limit of 6, 7, or 8 polyalkylene glycol subunits and in certain embodiments, the polyalkylene glycol moiety has 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

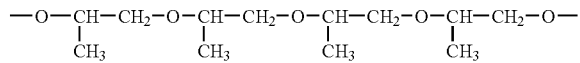

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

The oligomer can comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer can further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

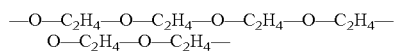

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

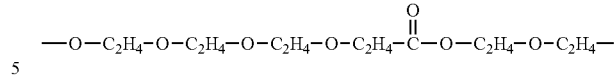

is a polyethylene glycol moiety having four polyethylene glycol subunits and an additional hydrophilic moiety having two polyethylene glycol subunits. Oligomers according to some embodiments of the present invention can comprise a polyalkylene glycol moiety and no additional hydrophilic moieties.

The oligomer can further comprise one or more lipophilic moieties as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms and/or between a lower limit of 3, 4, 5, 6, 7, 8, or 9 and an upper limit of 4, 5, 6, 7, 8, 9, 10, 11, 12, 13, or 14 carbon atoms. In some embodiments, the lipophilic moiety can have between a lower limit of 3, 4, 5, 6, or 7 and an upper limit of 6, 7, 8, 9, or 10 carbon atoms and in certain embodiments, the lipophilic moiety has 6 carbon atoms. The lipophilic moiety can be, but is not limited to, saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaenoate, and docosahexaenoate; and saturated fatty acid moieties such as acetate, caproate, caprylate, caprate, laurate, arachidate, behenate, lignocerate, and cerotate.

The oligomer can further comprise one or more spacer moieties as will be understood by those skilled in the art. Spacer moieties can, for example, be used to separate a hydrophilic moiety from a lipophilic moiety, to separate a lipophilic moiety or hydrophilic moiety from the proinsulin polypeptide, to separate a first hydrophilic or lipophilic moiety from a second hydrophilic or lipophilic moiety, or to separate a hydrophilic moiety or lipophilic moiety from a linker moiety. Spacer moieties can be, but are not limited to, sugar, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms.

The oligomer can further comprise one or more linker moieties that are used to couple the oligomer with the proinsulin polypeptide as will be understood by those skilled in the art. Linker moieties can be, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaenoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can also have between 1, 2, 3, 4, or 5 and 8, 10, 12, 14 or 16 carbon atoms.

The oligomer can further comprise one or more terminating moieties at the one or more ends of the oligomer, which are not coupled to the insulin polypeptide. The terminating moiety can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms, and/or between a lower limit of 1, 2, 3, 4, or 5 and an upper limit of 5, 6, 7, 8, 9, or 10 carbon atoms. In some embodiments, the alkyl or alkoxy moiety can have between a lower limit of 1, 2, 3, or 4 and an upper limit of 5, 6, or 7 carbon atoms. The alkyl moiety can be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In certain embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugars, cholesterol, alcohols, fatty acids and mPEG moieties.

According to other embodiments of the present invention, the oligomer comprises the structure of Formula I:

$$A\text{-}L_j\text{-}G_k\text{-}R\text{-}G'_m\text{-}R'\text{-}G''_n\text{-}T \qquad (I)$$

wherein:

A is an activatable moiety;

L is a linker moiety;

G, G' and G'' are individually selected spacer moieties;

R is a lipophilic moiety and R' is a polyalkylene glycol moiety, or R' is the lipophilic moiety and R is the polyalkylene glycol moiety (only one of R or R' must be present and typically, when R' is absent, G'' will also be absent and R is absent, G is also absent);

T is a terminating moiety; and j, k, m and n are individually 0 or 1.

According to various embodiments of the present invention, the polyalkylene glycol moiety can have at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits, and/or between a lower limit of 3, 4, 5, or 6 and an upper limit of 5, 6, 7, 8, 9, 10, 11, or 12 polyalkylene glycol subunits. In certain embodiments, the polyalkylene glycol moiety has between a lower limit of 4, 5, or 6 and an upper limit of 6, 7, or 8 polyalkylene glycol subunits and the polyalkylene glycol moiety can have 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

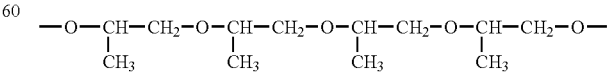

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms and/or can have between a lower limit of 3, 4, 5, 6, 7, 8, or 9 and an upper limit of 4, 5, 6, 7, 8, 9, 10, 11, 12, 13, or 14 carbon atoms. In certain embodiments, the lipophilic moiety has between a lower limit of 3, 4, 5, 6, or 7 and an upper limit of 6, 7, 8, 9, or 10 carbon atoms and the lipophilic moiety can have 6 carbon atoms. The lipophilic moiety is can be, but is not limited to, saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties can be, but are not limited to, sugar moieties, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms. Oligomers of certain embodiments do not include spacer moieties (i.e., k, m and n are 0).

According to these embodiments of the present invention, the linker moiety, L, can be used to couple the oligomer with the drug (e.g., an insulin drug) as will be understood by those skilled in the art. Linker moieties can be, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can have between 1, 2, 3, 4, or 5 and 8, 10, 12, 14 or 16 carbon atoms.

According to various embodiments of the present invention, the terminating moiety, T, can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms, and/or between a lower limit of 1, 2, 3, 4, or 5 and an upper limit of 5, 6, 7, 8, 9, or 10 carbon atoms. In certain embodiments, the alkyl or alkoxy moiety can have between a lower limit of 1, 2, 3, or 4 and an upper limit of 5, 6, or 7 carbon atoms. The alkyl moiety can be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In some embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugar moieties, cholesterol, alcohols, fatty acid moieties and mPEG moieties.

According to these embodiments of the present invention, the activatable moiety, A, is a moiety that allows for the coupling of the oligomer to an activating agent to form an activated oligomer capable of coupling with the proinsulin polypeptide. The activatable moiety can be various activatable moieties as will be understood by those skilled in the art including, but not limited to, —C(O)—OH, C(S)—OH, —C(S)—SH, —OH, —SH, and $NH_2$.

In still other embodiments, the oligomer comprises the structure of Formula II:

$$A\text{-}X(CH_2)_m Y(C_2H_4O)_n R \quad\quad\quad (II)$$

wherein:

A is —C(O)—OH, C(S)—OH, —C(S)—SH, —OH, —SH, or $NH_2$;

X is an oxygen atom or a covalent bond, with the proviso X is not an oxygen atom when A is —OH;

Y is an ester, an ether, a carbamate, a carbonate, or an amide bonding moiety, and can be an ether bonding moiety;

m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits, and in certain embodiments, is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. The alkyl moiety in certain embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula III:

$$A\text{-}(CH_2)_m(OC_2H_4)_n OR \quad\quad\quad (III)$$

wherein:

A is —C(O)—OH, C(S)—OH, —C(S)—SH, —OH, —SH, or $NH_2$;

m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits, and in certain embodiments is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. The alkyl moiety in certain embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula IV:

(IV)

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits, and/or between a lower limit of 4, 5, or 6 and an upper limit of 6, 7, or 8 polyalkylene glycol subunits, and in certain embodiments, is 7; and R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. The alkyl moiety in certain embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula V:

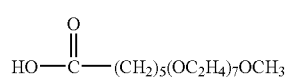

(V)

In various embodiments described above, the oligomer is covalently coupled to the insulin polypeptide as an insulin drug. For example, an oligomer of the present invention can comprise the structure Va:

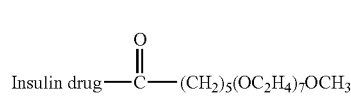

(Va)

wherein the insulin drug is an insulin polypeptide as described herein. When the insulin drug is a human insulin and the conjugate of Formula Va consists of the single oligomer coupled to the Lysine at the B29 position of the human insulin, the insulin-oligomer conjugate is referred to as HIM2.

In some embodiments, the oligomer can be coupled to the insulin polypeptide utilizing a hydrolyzable bond (e.g., an ester or carbonate bond). A hydrolyzable coupling can provide an insulin polypeptide-oligomer conjugate that acts as a prodrug. In certain instances, for example where the insulin polypeptide-oligomer conjugate is biologically inactive (i.e., the conjugate lacks the ability to affect the body through the insulin polypeptide's primary mechanism of action), a hydrolyzable coupling can provide for a time-release or controlled-release effect, providing the biologically active insulin polypeptide over a given time period as one or more oligomers are cleaved from their respective biologically inactive insulin polypeptide-oligomer conjugates to provide the biologically active insulin polypeptide. In some embodiments, the oligomer can be cleaved from a proinsulin polypeptide or an insulin polypeptide to yield insulin. A hydrolyzable bond can be included within the oligomer to yield a prodrug that yields a conjugated active moiety.

In other embodiments, the oligomer is coupled to the insulin polypeptide utilizing a non-hydrolyzable bond (e.g., a carbamate, amide, or ether bond). Use of a non-hydrolyzable bond can be preferable when it is desirable to allow the biologically inactive insulin polypeptide-oligomer conjugate to circulate in the bloodstream for an extended period of time, preferably at least 2 hours. When the oligomer is coupled to the insulin polypeptide utilizing a bonding moiety that comprises a carbonyl moiety, such as an ester, a carbamate, a carbonate, or an amide bonding moiety, the resulting insulin polypeptide-oligomer conjugate is an insulin polypeptide-acyl oligomer conjugate.

Oligomers employed in the various embodiments described above are commercially available or can be synthesized by various methods as will be understood by those skilled in the art. For example, polydispersed oligomers can be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers can be synthesized by methods provided in one or more of the following references, the disclosures of which are incorporated by reference herein in their entireties: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention can be substantially monodispersed and can also be monodispersed. Exemplary methods for synthesizing monodispersed oligomers are provided in the Examples provided herein.

The contacting of the proinsulin polypeptide with the oligomer under conditions sufficient to provide a proinsulin polypeptide-oligomer conjugate can be performed utilizing various conditions as will be understood by those skilled in the the art. The contacting of the proinsulin polypeptide with the oligomer under conditions sufficient to provide a proinsulin polypeptide-oligomer conjugate comprises contacting the oligomer with an activating agent under conditions sufficient to provide an activated oligomer; and contacting the activated oligomer with the proinsulin polypeptide under conditions sufficient to provide the proinsulin polypeptide conjugate. The activated oligomer can be formed ex situ or in situ.

The activating agent can be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999), the disclosure of which is incorporated by reference herein in its entirety for the teachings of coupling an activating agent to an oligomer.

The conditions sufficient to couple the activated oligomer to the proinsulin polypeptide will be understood to one of skill in the art. For example, the proinsulin polypeptide can be dissolved in a dipolar aprotic solvent, such as dimethylsulfoxide, to provide a proinsulin polypeptide solution. A buffering agent, such as triethylamine, can be added to the proinsulin polypeptide solution. The activated oligomer dissolved in an anhydrous solvent such as acetonitrile can then be added to the proinsulin polypeptide solution. One skilled in the art can also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to proinsulin polypeptide can be greater than about 1:1, greater than about 2:1, greater than about 3:1, greater than about 4:1, and/or greater than about 5:1.

In the various embodiments described above, more than one oligomer (i.e., a plurality of oligomers) can be coupled to the insulin polypeptide portion of the proinsulin polypeptide. Alternatively, the oligomer(s) can be coupled to a non-insulin polypeptide portion of a proinsulin polypeptide, for example, to facilitate purification of the conjugated insulin. The oligomers in the plurality can be the same. However, it is to be understood that the oligomers in the plurality can be different from one another, or, alternatively, some of the oligomers in the plurality can be the same and some can be different. When a plurality of oligomers is coupled to the insulin polypeptide portion of the proinsulin polypeptide, one or more of the oligomers can be coupled to the insulin polypeptide portion of the proinsulin polypeptide with hydrolyzable bonds and one or more of the oligomers can be coupled to the insulin polypeptide portion of the proinsulin polypeptide with non-hydrolyzable bonds. Alternatively, all of the bonds coupling the plurality of oligomers to the insulin polypeptide portion of the proinsulin polypeptide can be hydrolyzable, but have varying degrees of hydrolyzability such that, for example, one or more of the oligomers is rapidly removed from the insulin polypeptide or insulin polypeptide portion of the proinsulin polypeptide by hydrolysis in the body and one or more of the oligomers is slowly removed from the insulin polypeptide or insulin polypeptide portion by hydrolysis in the body.

In various embodiments described above, the oligomer can be coupled to the insulin polypeptide portion of the proinsulin polypeptide and optionally to the non-insulin polypeptide portion of the proinsulin polypeptide at various nucleophilic residues of the insulin polypeptide portion and/or the non-insulin polypeptide portion including, but not limited to, nucleophilic hydroxyl functions and/or amino functions. A nucleophilic hydroxyl function can be found, for example, at serine and/or tyrosine residues, and a nucleophilic amino function can be found, for example, at histidine and/or lysine residues, and/or at the one or more N-termini of the polypeptide. When an oligomer is coupled to the one or more N-termini of the proinsulin polypeptide, the coupling can form a secondary amine. When the proinsulin polypeptide has a leader peptide coupled to the N-terminus of the B-chain polypeptide, the N-termini of the insulin molecule can be protected from conjugation (e.g., acylation). When the proinsulin polypeptide is human proinsulin having a leader peptide coupled to the N-terminus of the B-chain, for example, the oligomer can be coupled to the three amino functionalities of the proinsulin: the N-terminus of the leader peptide, the amino functionality of the Lys residue in the C-peptide, and the amino functionality of $Lys^{B29}$. Upon cleavage of the leader peptide and the C-peptide, one finds that the oligomer has been site specifically coupled to the $Lys^{B29}$ of the insulin to provide a single insulin conjugate, insulin mono-conjugated with an oligomer at $Lys^{B29}$.

The cleaving of the one or more peptides from the proinsulin polypeptide-oligomer conjugate to provide the insulin polypeptide-oligomer conjugate can be performed by various processes as will be understood by those skilled in the art. In some embodiments, the cleaving of the one or more peptides from the proinsulin polypeptide-oligomer conjugate comprises contacting the proinsulin polypeptide-oligomer conjugate with one or more enzymes that are capable of cleaving the bond(s) between the one or more peptides and the insulin polypeptide under conditions sufficient to cleave the one or more peptides from the proinsulin polypeptide-oligomer conjugate. As described in various references, for example, Kemmler et al. "Studies on the Conversion of Proinsulin to Insulin," J. Biol. Chem., 246: 6786–6791 (1971), the disclosure of which is incorporated herein by reference in its entirety, one skilled in the art will understand how to select appropriate enzymes in view of the particular peptide bond(s) to be cleaved and how to provide conditions sufficient to cleave the one or more peptides from the proinsulin polypeptide-oligomer conjugate. The one or more enzymes can, for example, comprise various enzymes including, but not limited to, trypsin, chymotrypsin, carboxy peptidase B, and mixtures thereof. In certain embodiments, the one or more enzymes are trypsin, carboxy peptidase B, and mixtures thereof.

In some embodiments such as those described above having a connecting peptide, the connecting peptide has a terminal amino acid residue at the first end. In some of these embodiments, the cleaving of the connecting peptide from the proinsulin polypeptide-oligomer conjugate comprises contacting the proinsulin polypeptide-oligomer conjugate with a first enzyme under conditions sufficient to provide a terminal amino acid residue-insulin polypeptide-oligomer conjugate, and contacting the terminal amino acid residue-insulin polypeptide-oligomer conjugate with a second enzyme under conditions sufficient to provide the insulin polypeptide-oligomer conjugate. The contacting of the proinsulin polypeptide-oligomer conjugate with a first enzyme and the contacting of the terminal amino acid residue-insulin polypeptide-oligomer conjugate with a second enzyme can occur substantially concurrently, for example when the first enzyme and the second enzyme are provided as a mixture or cocktail. In certain embodiments, the first enzyme can be trypsin and the second enzyme can be carboxy peptidase B. The terminal amino acid residue can be any of various residues, such as an arginine residue or a glu residue, the latter of which can be cleaved with glu-C-peptidase. For example, the terminal amino acid residue can be an arginine residue when the insulin polypeptide is insulin and the connecting peptide is human C-peptide.

The cleaving of the one or more peptides from the proinsulin polypeptide-oligomer conjugate provides an insulin polypeptide-oligomer conjugate product that consists of a single insulin polypeptide-oligomer conjugate (i.e., is substantially devoid of additional insulin polypeptide-oligomer conjugates). The insulin polypeptide-oligomer conjugate product can also consist of a single insulin polypeptide-oligomer monoconjugate. For example, in embodiments described above in which the proinsulin polypeptide comprises an insulin polypeptide having an A-chain polypeptide devoid of lysine residues and a B-chain polypeptide comprising a single lysine residue, the insulin polypeptide-oligomer conjugate product can consist of a single insulin polypeptide-oligomer monoconjugate where the oligomer is coupled to the lysine residue of the B-chain polypeptide. As another example, when the proinsulin polypeptide is proinsulin with a leader peptide, the cleaving of the C-peptide and the leader peptide from the proinsulin-oligomer conjugate provides an insulin-oligomer monoconjugate, wherein the insulin is monoconjugated at $Lys^{B29}$.

The embodiments of the methods for synthesizing insulin polypeptide-oligomer conjugates described above can result in a yield of insulin polypeptide-oligomer conjugates and/or diconjugates that is greater than 75, 76, 77, 78, or 79 percent. In certain embodiments, the yield is greater than 80, 81, 82, 83, 84, or 85 percent. In certain other embodiments, the yield is greater than 86, 87, 88, 89, or 90 percent. In yet other embodiments, the yield is greater than 91, 92, 93, 94, or 95 percent. When the proinsulin polypeptide-oligomer conjugate is provided by contacting an activated oligomer with the proinsulin polypeptide-oligomer conjugate, an excess of activated oligomers can be used in achieving higher yields. For example, yields described herein can be obtained in various embodiments by using a molar ratio of activated oligomer to proinsulin polypeptide of greater than about 2:1, greater than about 3:1, greater than about 4:1, and/or greater than about 5:1. In some embodiments, yields greater than 91, 92, 93, 94, or 95 percent are obtained using a molar ratio of activated oligomer to proinsulin polypeptide of greater than about 4:1, and some embodiments, greater than about 5:1.

According to other embodiments of the present invention, methods of synthesizing a proinsulin polypeptide-oligomer conjugate are provided that include contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate. For example, proinsulin-oligomer conjugates can be synthesized as described in the Examples provided below. An embodiment of a synthesis route is provided in FIG. 1.

The proinsulin polypeptide can be various proinsulin polypeptides comprising an insulin polypeptide coupled to one or more peptides by peptide bond(s) capable of being cleaved to yield the insulin polypeptide as will be understood by those skilled in the art including, but not limited to, proinsulin, proinsulin analogs, proinsulin fragments, proinsulin fragment analogs, miniproinsulin, SCIP, or fusion proteins. In some embodiments, the proinsulin polypeptide is a proinsulin analog having a leader peptide. The proinsulin analog having a leader peptide can be obtained, for example, from Itoham Foods, Inc. of Ibaraki Pref, Japan. The leader peptide and the C-peptide of the proinsulin analog are each devoid of lysine residues. In other embodiments, the proinsulin polypeptide is a proinsulin polypeptide that can be obtained, for example, from Biobras of Belo Horizonte, Brazil. The proinsulin polypeptide has a leader peptide coupled to the N-terminus of the B-chain of the proinsulin. The leader peptide is devoid of lysine residues.

The insulin polypeptide can have an A-chain polypeptide and a B-chain polypeptide. The A-chain polypeptide can be devoid of lysine residues. The B-chain polypeptide can comprise a single lysine residue. The A-chain polypeptide and the B-chain polypeptide can be cross-linked, and can be cross-linked using one or more disulfide bonds. In certain embodiments, the A-chain polypeptide and the B-chain polypeptide each comprise cysteine residues, one or more of which are coupled using one or more disulfide bonds to cross-link the A-chain polypeptide with the B-chain polypeptide. The insulin polypeptide can be insulin, an insulin analog, an insulin fragment, or an insulin analog fragment.

In some embodiments, the one or more peptides coupled to the insulin polypeptide comprise a connecting peptide coupled at a first end to the C-terminus of the B-chain polypeptide and at a second end to the N-terminus of the A-chain polypeptide. In general, the amino acid sequence of the connecting peptide is not critical and the connecting peptide can be various connecting peptides as will be understood by those skilled in the art including, but not limited to, C-peptide polypeptides, C-peptides, and the connecting peptides in miniproinsulins. In some embodiments, the connecting peptide is devoid of lysine residues. These embodiments can utilize less oligomeric reagents by reducing the number of possible conjugation sites on the proinsulin polypeptide molecule.

In other embodiments, the one or more peptides coupled to the insulin polypeptide comprise a leader peptide that is coupled to the N-terminus of the B-chain polypeptide. In general, the amino acid sequence of the leader peptide is not critical. In some embodiments, the leader peptide is devoid of lysine residues. These embodiments can reduce the amount of oligomeric reagent used by limiting the number of conjugation sites on the proinsulin polypeptide molecule.

In still other embodiments, the one or more peptides coupled to the insulin polypeptide comprise both a connecting peptide as described above and a leader peptide as described above. The one or more peptides can consist essentially of a connecting peptide and a leader peptide, or can consist of a connecting peptide and a leader peptide.

The peptide bonds are bonds that can be cleaved in various ways as will be understood by those skilled in the art. The peptide bonds are bonds that can be enzymatically cleaved by enzymes including, but not limited to, trypsin, carboxy peptidase B, thrombin, pepsin, and chymotrypsin. Peptide bonds that can be enzymatically cleaved will be understood by those skilled in the art and include, but are not limited to, Arg—-Arg, Thr-Arg, Ala-Arg, Thr-Arg-Arg, Thr-Lys, Arg-Gly, and Arg-Phe.

The oligomer can be various oligomers as will be understood by those skilled in the art. In general, the oligomer can be any oligomer capable of being coupled to a polypeptide as will be understood by those skilled in the art. For example, the oligomer can be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al. As another example, the oligomer can be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same." In alternative embodiments, only the polyalkene glycol of the oligomer is substantially non-dispersed.

The oligomer can comprise a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety can be a polyalkylene glycol moiety. The polyalkylene glycol moiety can have at least 1, 2, 3, 4, 5, 6 or 7 polyalkylene glycol subunits. The polyalkylene glycol moiety can also have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. In some embodiments, the polyalkylene glycol moiety can have between a lower limit of 3, 4, 5, or 6 and an upper limit of 5, 6, 7, 8, 9, 10, 11, or 12 polyalkylene glycol subunits. The polyalkylene glycol moiety can also have between a lower limit of 4, 5, or 6 and an upper limit of 6, 7, or 8 polyalkylene glycol subunits and in certain embodiments, has 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

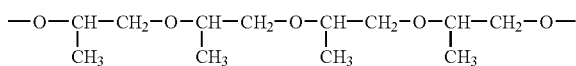

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

The oligomer can comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer can further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties are considered to be the same moiety if they are coupled by ether bonds. For example, the moiety

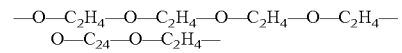

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

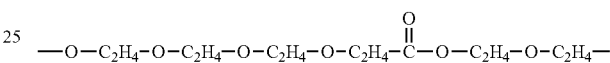

is a polyethylene glycol moiety having four polyethylene glycol subunits and an additional hydrophilic moiety having two polyethylene glycol subunits. Oligomers according to some embodiments of the present invention can comprise a polyalkylene glycol moiety and no additional hydrophilic moieties.

The oligomer can further comprise one or more lipophilic moieties as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms and/or between a lower limit of 3, 4, 5, 6, 7, 8, or 9 and an upper limit of 4, 5, 6, 7, 8, 9, 10, 11, 12, 13, or 14 carbon atoms. In some embodiments, the lipophilic moiety can have between a lower limit of 3, 4, 5, 6, or 7 and an upper limit of 6, 7, 8, 9, or 10 carbon atoms and in certain embodiments, has 6 carbon atoms. The lipophilic moiety can be saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

The oligomer can further comprise one or more spacer moieties as will be understood by those skilled in the art. Spacer moieties can, for example, be used to separate a hydrophilic moiety from a lipophilic moiety, to separate a lipophilic moiety or hydrophilic moiety from the proinsulin polypeptide, to separate a first hydrophilic or lipophilic moiety from a second hydrophilic or lipophilic moiety, or to separate a hydrophilic moiety or lipophilic moiety from a linker moiety. Spacer moieties can be, but are not limited to, sugar, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms.

The oligomer can further comprise one or more linker moieties that are used to couple the oligomer with the proinsulin polypeptide as will be understood by those skilled in the art. Linker moieties can be, for example, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can have between 1, 2, 3, 4, or 5 and 8, 10, 12, 14 or 16 carbon atoms.

The oligomer can further comprise one or more terminating moieties at the one or more ends of the oligomer, which are not coupled to the insulin polypeptide. The terminating moiety can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms and/or between a lower limit of 1, 2, 3, 4, or 5 and an upper limit of 5, 6, 7, 8, 9, or 10 carbon atoms. In some embodiments, the alkyl or alkoxy moiety can have between a lower limit of 1, 2, 3, or 4 and an upper limit of 5, 6, or 7 carbon atoms. The alkyl moiety can be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In some embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugars, cholesterol, alcohols, and fatty acids.

According to other embodiments of the present invention, the oligomer comprises the structure of Formula VI:

A-L$_j$-G$_k$-R-G'$_m$-R'-G''$_n$-T     (VI)

wherein:

A is an activatable moiety;

L is a linker moiety;

G, G' and G'' are individually selected spacer moieties;

R is a lipophilic moiety and R' is a polyalkylene glycol moiety, or R' is the lipophilic moiety and R is the polyalkylene glycol moiety and only one of R or R' is required;

T is a terminating moiety; and j, k, m and n are individually 0 or 1.

According to these embodiments of the present invention, the polyalkylene glycol moiety can have at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits and/or between a lower limit of 3, 4, 5, or 6 and an upper limit of 5, 6, 7, 8, 9, 10, 11, or 12 polyalkylene glycol subunits. In some embodiments, the polyalkylene glycol moiety can have between a lower limit of 4, 5, or 6 and an upper limit of 6, 7, or 8 polyalkylene glycol subunits and in certain embodiments, the polyalkylene glycol moiety has 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

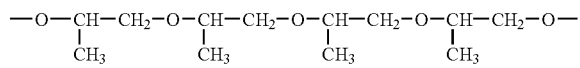

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms and/or between a lower limit of 3, 4, 5, 6, 7, 8, or 9 and an upper limit of 4, 5, 6, 7, 8, 9, 10, 11, 12, 13, or 14 carbon atoms. In some embodiments, the lipophilic moiety can have between a lower limit of 3, 4, 5, 6, or 7 and an upper limit of 6, 7, 8, 9, or 10 carbon atoms and in certain embodiments, the lipophilic moiety has 6 carbon atoms. The lipophilic moiety can be, but is not limited to, saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties can be sugar moieties, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms. In certain embodiments, oligomers of these embodiments do not include spacer moieties (i.e., k, m and n are preferably 0).

According to these embodiments of the present invention, the linker moiety, L, can be used to couple the oligomer with the drug as will be understood by those skilled in the art. Linker moieties can be alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can have between 1, 2, 3, 4, or 5 and 8, 10, 12, 14 or 16 carbon atoms.

According to various embodiments of the present invention, the terminating moiety, T, can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms. The alkyl or alkoxy moiety can also have a lower limit of 1, 2, 3, 4, or 5 and an upper limit of 5, 6, 7, 8, 9, or 10 carbon atoms, and/or between a lower limit of 1, 2, 3, or 4 and an upper limit of 5, 6, or 7 carbon atoms. The alkyl moiety can be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In certain embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugar moieties, cholesterol, alcohols, and fatty acid moieties.

According to these embodiments of the present invention, the activatable moiety, A, is a moiety that allows for the coupling of the oligomer to an activating agent to form an activated oligomer capable of coupling with the proinsulin polypeptide. The activatable moiety can be various activatable moieties as will be understood by those skilled in the art including, but not limited to, —C(O)—OH, C(S)—OH, —C(S)—SH, —OH, —SH, and NH$_2$.

In still other embodiments, the oligomer comprises the structure of Formula VII:

A-X(CH$_2$)$_m$Y(C$_2$H$_4$O)$_n$R  (VII)

wherein:

A is —C(O)—OH, C(S)—OH, —C(S)—SH, —OH, —SH, or NH$_2$;

X is an oxygen atom or a covalent bond, with the proviso X is not an oxygen atom when A is —OH;

Y is an ester, an ether, a carbamate, a carbonate, or an amide bonding moiety, and can be an ether bonding moiety;

m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, n is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a C$_1$ to C$_3$ alkyl. The alkyl moiety in certain embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula VIII:

A-(CH$_2$)$_m$(OC$_2$H$_4$)$_n$OR  (VIII)

wherein:

A is —C(O)—OH, C(S)—OH, —C(S)—SH, —OH, —SH, or NH$_2$;

m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and in some embodiments, can be between a lower limit of 3, 4, 5, 6, or 7 and an upper limit of 6, 7, 8, 9, or 10;

n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can be a C$_1$ to C$_3$ alkyl. The alkyl moiety in some embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula IX:

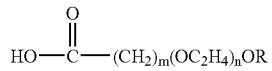 (IX)

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, n is 7; and R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. The alkyl moiety in some embodiments is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula X:

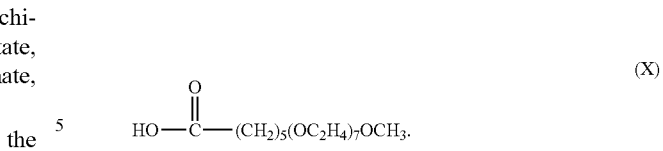

In the various embodiments of methods for synthesizing proinsulin polypeptide-oligomer conjugates described above, the oligomer is covalently coupled to the insulin polypeptide. In some embodiments, the oligomer is coupled to the insulin polypeptide utilizing a hydrolyzable bond (e.g., an ester or carbonate bond). A hydrolyzable coupling can provide an insulin polypeptide-oligomer conjugate that acts as a prodrug. In certain instances, for example where the insulin polypeptide-oligomer conjugate is biologically inactive (i.e., the conjugate lacks the ability to affect the body through the insulin polypeptide's primary mechanism of action), a hydrolyzable coupling can provide for a time-release or controlled-release effect, providing the biologically active insulin polypeptide over a given time period as one or more oligomers are cleaved from their respective biologically inactive insulin polypeptide-oligomer conjugates to provide the biologically active insulin polypeptide. In other embodiments, the oligomer is coupled to the insulin polypeptide utilizing a non-hydrolyzable bond (e.g., a carbamate, amide, or ether bond). Use of a non-hydrolyzable bond can be preferable when it is desirable to allow the biologically inactive insulin polypeptide-oligomer conjugate to circulate in the bloodstream for an extended period of time, preferably at least 2 hours. When the oligomer is coupled to the insulin polypeptide utilizing a bonding moiety that comprises a carbonyl moiety, such as an ester, a carbamate, a carbonate, or an amide bonding moiety, the resulting insulin polypeptide-oligomer conjugate is an insulin polypeptide-acyl oligomer conjugate.

Oligomers employed in the embodiments of methods for synthesizing proinsulin polypeptide oligomer conjugates described above are commercially available or can be synthesized by various methods as will be understood by those skilled in the art. For example, polydispersed oligomers can be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers can be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention can be substantially monodispersed and can be monodispersed. Exemplary methods for synthesizing monodispersed oligomers are provided in the Examples section provided herein.

The contacting of the proinsulin polypeptide with the oligomer under conditions sufficient to provide a proinsulin polypeptide-oligomer conjugate can be performed utilizing various conditions as will be understood by those skilled in the art. The contacting of the proinsulin polypeptide with the oligomer under conditions sufficient to provide a proinsulin polypeptide-oligomer conjugate comprises contacting the oligomer with an activating agent under conditions sufficient to provide an activated oligomer; and contacting the activated oligomer with the proinsulin polypeptide under conditions sufficient to provide the proinsulin polypeptide conjugate. The activated oligomer can be formed ex situ or in situ.

The activating agent can be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999).

The conditions sufficient to couple the activated oligomer to the proinsulin polypeptide will be understood to one of skill in the art. For example, the proinsulin polypeptide can be dissolved in a dipolar aprotic solvent, such as dimethylsulfoxide, to provide a proinsulin polypeptide solution. A buffering agent, such as triethylamine, can be added to the proinsulin polypeptide solution. The activated oligomer dissolved in an anhydrous solvent such as acetonitrile can then be added to the proinsulin polypeptide solution. One skilled in the art can also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to proinsulin polypeptide can be greater than about 1:1, can be greater than about 2:1, can be greater than about 3:1, can be greater than about 4:1, and can also be greater than about 5:1.

In the various embodiments of methods for synthesizing proinsulin polypeptide-oligomer conjugates described above, more than one oligomer (i.e., a plurality of oligomers) can be coupled to the insulin polypeptide portion of the proinsulin polypeptide. The oligomers in the plurality can be the same. However, it is to be understood that the oligomers in the plurality can be different from one another, or, alternatively, some of the oligomers in the plurality can be the same and some can be different. When a plurality of oligomers is coupled to the insulin polypeptide portion of the proinsulin polypeptide, it may be preferable to couple one or more of the oligomers to the insulin polypeptide portion of the proinsulin polypeptide with hydrolyzable bonds and couple one or more of the oligomers to the insulin polypeptide portion of the proinsulin polypeptide with non-hydrolyzable bonds. Alternatively, all of the bonds coupling the plurality of oligomers to the insulin polypeptide portion of the proinsulin polypeptide may be hydrolyzable, but have varying degrees of hydrolyzability such that, for example, one or more of the oligomers is rapidly removed from the insulin polypeptide or insulin polypeptide portion of the proinsulin polypeptide by hydrolysis in the body and one or more of the oligomers is slowly removed from the insulin polypeptide or insulin polypeptide portion by hydrolysis in the body.

In the various embodiments of methods for synthesizing proinsulin polypeptide-oligomer conjugates described above, the oligomer can be coupled to the insulin polypeptide portion of the proinsulin polypeptide at various nucleophilic residues of the insulin polypeptide portion including, but not limited to, nucleophilic hydroxyl functions and/or amino functions. A nucleophilic hydroxyl function can be found, for example, at serine and/or tyrosine residues, and a nucleophilic amino function can be found, for example, at histidine and/or lysine residues, and/or at the one or more N-termini of the polypeptide. When an oligomer is coupled to the one or more N-termini of the proinsulin polypeptide, the coupling can form a secondary amine. When the proinsulin polypeptide has a leader peptide coupled to the N-terminus of the B-chain polypeptide, the N-termini of the insulin molecule can be protected from conjugation (e.g., acylation). When the proinsulin polypeptide is human proinsulin having a leader peptide coupled to the N-terminus of the B-chain, for example, the oligomer can be coupled to the three amino functionalities of the proinsulin: the N-terminus of the leader peptide, the amino functionality of the Lys residue in the C-peptide, and the amino functionality of $Lys^{B29}$. Upon cleavage of the leader peptide and the C-peptide, one finds that the oligomer has been site specifically coupled to the $Lys^{B29}$ of the insulin to provide a single insulin conjugate, insulin mono-conjugated with an oligomer at $Lys^{B29}$.

According to still other embodiments of the present invention, a proinsulin polypeptide-oligomer conjugate includes a proinsulin polypeptide comprising an insulin polypeptide coupled to one or more peptides by peptide bond(s) that are cleavable to yield the insulin polypeptide, and an oligomer coupled to the insulin polypeptide portion of the proinsulin polypeptide.

The proinsulin polypeptide comprising an insulin polypeptide coupled to one or more peptides by peptide bond(s) that are cleavable to yield the insulin polypeptide can be various proinsulin polypeptides including, but not limited to, the proinsulin polypeptides described above with reference to the methods of synthesizing proinsulin polypeptide-oligomer conjugates. The oligomer can be various oligomers including, but not limited to, the oligomers described above with reference to the methods of synthesizing proinsulin polypeptide-oligomer conjugates. The oligomer can comprise a hydrophilic moiety and a lipophilic moiety. Proinsulin polypeptide-oligomer conjugates according to the present invention can be synthesized by various methods as will be understood by those skilled in the art including, but not limited to, the methods of synthesizing proinsulin polypeptide-oligomer conjugates described herein.

According to yet other embodiments, a method of synthesizing a C-peptide polypeptide-oligomer conjugate is provided, that includes contacting a pro-C-peptide polypeptide comprising a C-peptide polypeptide coupled to one or more peptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate, and cleaving the one or more peptides from the pro-C-peptide polypeptide-oligomer conjugate to provide the C-peptide polypeptide-oligomer conjugate.

The pro-C-peptide polypeptide can be various pro-C-peptide polypeptides as will be understood by those skilled in the art. The pro-C-peptide polypeptide can be a proinsulin polypeptide, and in some embodiments, the pro-C-peptide polypeptide is proinsulin.

The C-peptide polypeptide can be various C-peptide polypeptides as will be understood by those skilled in the art. In some embodiments, the C-peptide polypeptide is C-peptide.

The one or more peptides coupled to the C-peptide polypeptide can be various peptides as will be understood by those skilled in the art. The one or more peptides can comprise an insulin polypeptide and/or the one or more polypeptides can be an insulin polypeptide. The insulin polypeptide can be devoid of lysine residues, which can reduce the amount of oligomeric reagents utilized to conjugate the pro-C-peptide polypeptide. The one or more peptides can also be insulin or insulin coupled at the N-terminus of the B-chain to a leader peptide.

The peptide bonds are bonds that can be cleaved in various ways as will be understood by those skilled in the art. The peptide bonds can be bonds that can be enzymatically cleaved by enzymes including, but not limited to, trypsin, carboxy peptidase B, thrombin, pepsin, and chymotrypsin. Peptide bonds that can be enzymatically cleaved will be understood by those skilled in the art and include, but are not limited to, Arg-Arg, Thr-Arg, Ala-Arg, Thr-Arg-Arg, Thr-Lys, Arg-Gly, and Arg-Phe.

The oligomer can be various oligomers as will be understood by those skilled in the art. In general, the oligomer can be any oligomer capable of being coupled to a polypeptide as will be understood by those skilled in the art. For example, the oligomer can be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al. As another example, the oligomer can be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same."

The oligomer can comprise, consist essentially of, or consist of, a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety can be a polyalkylene glycol moiety. The polyalkylene glycol moiety can have at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits, and/or between a lower limit of 3, 4, 5, or 6 and an upper limit of 5, 6, 7, 8, 9, 10, 11, or 12 polyalkylene glycol subunits. The polyalkylene glycol moiety can also have between a lower limit of 4, 5, or 6 and an upper limit of 6, 7, or 8 polyalkylene glycol subunits and in some embodiments, the polyalkylene glycol moiety has 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

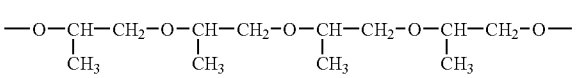

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

The oligomer can comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer can further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

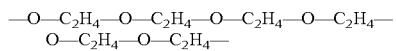

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties are considered to be different moieties if they are coupled by a bond other than an ether bond. For example, the moiety

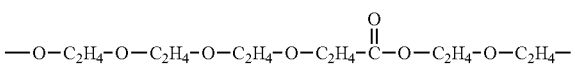

is a polyethylene glycol moiety having four polyethylene glycol subunits and an additional hydrophilic moiety having two polyethylene glycol subunits. Oligomers according to various embodiments of the present invention comprise a polyalkylene glycol moiety and no additional hydrophilic moieties.

The oligomer can further comprise one or more lipophilic moieties as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms, and/or between a lower limit of 3, 4, 5, 6, 7, 8, or 9 and an upper limit of 4, 5, 6, 7, 8, 9, 10, 11, 12, 13, or 14 carbon atoms. The lipophilic moiety can also have between a lower limit of 3, 4, 5, 6, or 7 and an upper limit of 6, 7, 8, 9, or 10 carbon atoms and in certain embodiments, the lipophilic moiety has 6 carbon atoms. The lipophilic moiety can be, but is not limited to saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

The oligomer can further comprise one or more spacer moieties as will be understood by those skilled in the art. Spacer moieties can, for example, be used to separate a hydrophilic moiety from a lipophilic moiety, to separate a lipophilic moiety or hydrophilic moiety from the C-peptide polypeptide, to separate a first hydrophilic or lipophilic moiety from a second hydrophilic or lipophilic moiety, or to separate a hydrophilic moiety or lipophilic moiety from a linker moiety. Spacer moieties can be, but are not limited to, sugar, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms.

The oligomer can further comprise one or more linker moieties that are used to couple the oligomer with the C-peptide polypeptide as will be understood by those skilled in the art. Linker moieties can be, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can also have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can also have between 1, 2, 3, 4, or 5 and 8, 10, 12, 14 or 16 carbon atoms.

The oligomer can further comprise one or more terminating moieties at the one or more ends of the oligomer, which are not coupled to the C-peptide polypeptide. The terminating moiety can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms, and/or between a lower limit of 1, 2, 3, or 4 and an upper limit of 5, 6, 7, 8, 9, or 10 carbon atoms. In certain embodiments, the alkyl or alkoxy moiety can have between a lower limit of 1, 2, 3, or 4 and an upper limit of 5, 6, or 7 carbon atoms. The alkyl moiety can be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In certain embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugars, cholesterol, alcohols, fatty acids and PEG moieties.

According to other embodiments of the present invention, the oligomer comprises the structure of Formula XI:

wherein:
A is an activatable moiety;
L is a linker moiety;
G, G' and G" are individually selected spacer moieties;
R is a lipophilic moiety and R' is a polyalkylene glycol moiety, or R' is the lipophilic moiety and R is the polyalkylene glycol moiety and only one of R and R' must be present;
T is a terminating moiety; and
j, k, m and n are individually 0 or 1.

According to these embodiments of the present invention, the polyalkylene glycol moiety can have at least 1, 2, 3, 4, 5, 6 or 7 polyalkylene glycol subunits. The polyalkylene glycol moiety can have between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety can also have between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits, and/or between a lower limit of 3, 4, 5, or 6 and an upper limit of 5, 6, 7, 8, 9, 10, 11, or 12 polyalkylene glycol subunits. In some embodiments, the polyalkylene glycol moiety can have between a lower limit of 4, 5, or 6 and an upper limit of 6, 7, or 8 polyalkylene glycol subunits and in certain embodiments, the polyalkylene glycol moiety has 7 polyalkylene glycol subunits. The polyalkylene glycol moiety of the oligomer can be a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety can have a uniform (i.e., not random) structure. An exemplary polypropylene glycol moiety having a uniform structure is as follows:

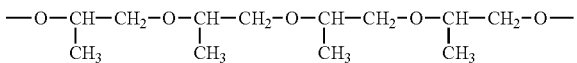

This uniform polypropylene glycol structure can be described as having only one methyl substituted carbon atom adjacent each oxygen atom in the polypropylene glycol chain. Such uniform polypropylene glycol moieties can exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety can have between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety can also have between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms, and/or between a lower limit of 3, 4, 5, 6, 7, 8, or 9 and an upper limit of 4, 5, 6, 7, 8, 9, 10, 11, 12, 13, or 14 carbon atoms. In some embodiments, the lipophilic moiety can have between a lower limit of 3, 4, 5, 6, or 7 and an upper limit of 6, 7, 8, 9, or 10 carbon atoms and in certain embodiments, the lipophilic moiety has 6 carbon atoms. The lipophilic moiety can be, but is not limited to, saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties can be, but are not limited to, sugar moieties, cholesterol and glycerine moieties. Sugar moieties can be various sugar moieties as will be understood by those skilled in the art including, but not limited to, monosaccharide moieties and disaccharide moieties. Monosaccharide moieties can have between 4 and 6 carbon atoms. Oligomers of certain embodiments do not include spacer moieties (i.e., k, m and n are 0).

According to various embodiments of the present invention, the linker moiety, L, can be used to couple the oligomer with the C-peptide polypeptide as will be understood by those skilled in the art. Linker moieties can be, but are not limited to, alkyl and fatty acid moieties. The alkyl linker moiety can be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and can also have between 1, 2, 3, 4, or 5 and 8, 9, 10, 11, or 12 carbon atoms. The fatty acid linker moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and can have between 1, 2, 3, 4, or 5 and 8, 10, 12, 14 or 16 carbon atoms.

According to these embodiments of the present invention, the terminating moiety, T, can be an alkyl or alkoxy moiety. The alkyl or alkoxy moiety can have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety can also have between a lower limit of 1, 2, 3, 4, 5, 6, or 7 and an upper limit of 5, 6, 7, 8, 9, 10, 11, 12, 13, or 14 carbon atoms, and/or between a lower limit of 1, 2, 3, 4, or 5 and an upper limit of 5, 6, 7, 8, 9, or 10 carbon atoms. In some embodiments, the alkyl or alkoxy moiety can have between a lower limit of 1, 2, 3, or 4 and an upper limit of 5, 6, or 7 carbon atoms. The alkyl moiety can be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methylpentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties can be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety can be a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. In certain embodiments, the terminating moiety is methyl or methoxy. While the terminating moiety can be an alkyl or alkoxy moiety, it is to be understood that the terminating moiety can be various moieties as will be understood by those skilled in the art including, but not limited to, sugar moieties, cholesterol, alcohols, fatty acid moieties and mPEG moieties.

According to these embodiments of the present invention, the activatable moiety, A, is a moiety that allows for the coupling of the oligomer to an activating agent to form an activated oligomer capable of coupling with the proinsulin polypeptide. The activatable moiety can be various activatable moieties as will be understood by those skilled in the art including, but not limited to, —C(O)—OH, C(S)—OH, —C(S)—SH, —OH, —SH, and NH$_2$.

In still other embodiments, the oligomer comprises the structure of Formula XII:

A-X(CH$_2$)$_m$Y(C$_2$H$_4$O)$_n$R    (XII)

wherein:

A is —C(O)—OH, C(S)—OH, —C(S)—SH, —OH, —SH, or NH$_2$;

X is an oxygen atom or a covalent bond, with the proviso X is not an oxygen atom when A is —OH;

Y is an ester, an ether, a carbamate, a carbonate, or an amide bonding moiety, and can be an ether bonding moiety;

m is between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n is between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, n is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. In certain embodiments, the alkyl moiety is methyl. The fatty acid moiety can be a saturated or unsaturated, linear or branched fatty acid moiety as will be understood by those skilled in the art, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula XIII:

A-(CH$_2$)$_m$(OC$_2$H$_4$)$_n$OR    (XIII)

wherein:

A is —C(O)—OH, C(S)—OH, —C(S)—SH, —OH, —SH, or NH$_2$;

m can be between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n can be between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, n is 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. In some embodiments, the alkyl moiety is methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula XIV:

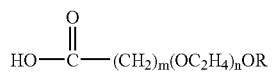

(XIV)

wherein:

m can be between a lower limit of 0, 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, and can be between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, and can also be between a lower limit of 3, 4, 5, 6, 7, 8, or 9 and an upper limit of 4, 5, 6, 7, 8, 9, 10, 11, 12, 13, or 14, and/or between a lower limit of 3, 4, 5, 6, or 7 and an upper limit of 6, 7, 8, 9, or 10;

n can be between a lower limit of 0, 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and can be between a lower limit of 2, 3, 4, 5, or 6 and an upper limit of 5, 6, 7, 8, 9, 10, 11, 12, 13, 14, 15, 16, 17, 18, 19, or 20, and can also be between a lower limit of 3, 4, 5, or 6 and an upper limit of 5, 6, 7, 8, 9, 10, 11, or 12 polyalkylene glycol subunits. In some embodiments, n can be between a lower limit of 4, 5, or 6 and an upper limit of 6, 7, or 8 polyalkylene glycol subunits, and in certain embodiments, n can be 7;

m and n are not both 0; and

R is an alkyl moiety, a sugar moiety, cholesterol, adamantane, an alcohol moiety, or a fatty acid moiety. The alkyl moiety can be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety can be a lower alkyl moiety such as methyl, ethyl, propyl, isopropyl, butyl, sec-butyl, tert-butyl, pentyl, or tert-pentyl. The alkyl moiety can also be a $C_1$ to $C_3$ alkyl. In certain embodiments, the alkyl moiety can be methyl. The fatty acid moiety can be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In the various embodiments of method for synthesizing C-peptide polypeptide oligomer conjugates described above, the oligomer is covalently coupled to the C-peptide polypeptide. In some embodiments, the oligomer is coupled to the C-peptide polypeptide utilizing a hydrolyzable bond (e.g., an ester or carbonate bond). A hydrolyzable coupling can provide a C-peptide polypeptide-oligomer conjugate that acts as a prodrug. In certain instances, for example where the C-peptide polypeptide-oligomer conjugate is biologically inactive (i.e., the conjugate lacks the ability to affect the body through the C-peptide polypeptide's primary mechanism of action), a hydrolyzable coupling may provide for a time-release or controlled-release effect, providing the biologically active C-peptide polypeptide over a given time period as one or more oligomers are cleaved from their respective biologically inactive C-peptide polypeptide-oligomer conjugates to provide the biologically active C-peptide polypeptide. In alternative embodiments, the oligomer is cleaved to yield C-peptide. In other embodiments, the oligomer is coupled to the C-peptide polypeptide utilizing a non-hydrolyzable bond (e.g., a carbamate, amide, or ether bond). Use of a non-hydrolyzable bond may be preferable when it is desirable to allow the biologically inactive C-peptide polypeptide-oligomer conjugate to circulate in the bloodstream for an extended period of time, preferably at least 2 hours. When the oligomer is coupled to the C-peptide polypeptide utilizing a bonding moiety that comprises a carbonyl moiety, such as an ester, a carbamate, a carbonate, or an amide bonding moiety, the resulting C-peptide polypeptide-oligomer conjugate is a C-peptide polypeptide-acyl oligomer conjugate.

Oligomers employed in the various methods of synthesizing C-peptide polypeptide-oligomer conjugates described above are commercially available or can be synthesized by various methods as will be understood by those skilled in the art. For example, polydispersed oligomers can be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S.

Pat. No. 5,681,811 to Ekwuribe, U.S. Pat. No. 6,309,633 to Ekwuribe et al. Non-polydispersed (e.g., substantially monodispersed and monodispersed) oligomers can be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention can be substantially monodispersed and can also be monodispersed. Exemplary methods for synthesizing monodispersed oligomers are provided in the Examples provided herein.

The contacting of the pro-C-peptide polypeptide with the oligomer under conditions sufficient to provide a pro-C-peptide polypeptide-oligomer conjugate can be performed utilizing various conditions as will be understood by those skilled in the art. The contacting of the pro-C-peptide polypeptide with the oligomer under conditions sufficient to provide a pro-C-peptide polypeptide-oligomer conjugate comprises contacting the oligomer with an activating agent under conditions sufficient to provide an activated oligomer; and contacting the activated oligomer with the pro-C-peptide polypeptide under conditions sufficient to provide the pro-C-peptide polypeptide conjugate. The activated oligomer can be formed ex situ or in situ.

The activating agent can be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999).

The conditions sufficient to couple the activated oligomer to the pro-C-peptide polypeptide will be understood to one of skill in the art. For example, the pro-C-peptide polypeptide can be dissolved in a dipolar aprotic solvent, such as dimethylsulfoxide, to provide a pro-C-peptide polypeptide solution. A buffering agent, such as triethylamine, can be added to the pro-C-peptide polypeptide solution. The activated oligomer dissolved in an anhydrous solvent such as acetonitrile can then be added to the pro-C-peptide polypeptide solution. One skilled in the art can also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to pro-C-peptide polypeptide can be greater than about 1:1, greater than about 2:1, greater than about 3:1, greater than about 4:1, and/or greater than about 5:1.

In the various embodiments of methods for synthesizing C-peptide polypeptide-oligomer conjugates described above, more than one oligomer (i.e., a plurality of oligomers) can be coupled to the C-peptide polypeptide portion of the pro-C-peptide polypeptide. In other embodiments, the oligomer(s) can be conjugated to the C-peptide and insulin polypeptide portions of the pro-C-peptide polypeptide, for example, to facilitate separation. The oligomers in the plurality can be the same. However, it is to be understood that the oligomers in the plurality can be different from one another, or, alternatively, some of the oligomers in the plurality can be the same and some can be different. When a plurality of oligomers is coupled to the C-peptide polypeptide portion of the pro-C-peptide polypeptide, one or more of the oligomers can be coupled to the C-peptide polypeptide portion of the pro-C-peptide polypeptide with hydrolyzable bonds and one or more of the oligomers can be coupled to the C-peptide polypeptide portion of the pro-C-peptide polypeptide with non-hydrolyzable bonds. Alternatively, all of the bonds coupling the plurality of oligomers to the C-peptide polypeptide portion of the pro-C-peptide polypeptide may be hydrolyzable, but have varying degrees of hydrolyzability such that, for example, one or more of the oligomers is rapidly removed from the C-peptide polypeptide or C-peptide polypeptide portion of the pro-C-peptide polypeptide by hydrolysis in the body and one or more of the oligomers is slowly removed from the C-peptide polypeptide or C-peptide polypeptide portion by hydrolysis in the body.

In the various embodiments of methods for synthesizing C-peptide polypeptide-oligomer conjugates described above, the oligomer can be coupled to the C-peptide polypeptide portion of the pro-C-peptide polypeptide (and optionally to the insulin polypeptide portion and/or the leader polypeptide portion when present) at various nucleophilic residues of the C-peptide polypeptide portion including, but not limited to, nucleophilic hydroxyl functions and/or amino functions. A nucleophilic hydroxyl function can be found, for example, at serine and/or tyrosine residues, and a nucleophilic amino function can be found, for example, at histidine and/or lysine residues, and/or at the one or more N-termini of the polypeptide. When an oligomer is coupled to the one or more N-termini of the proinsulin polypeptide, the coupling can form a secondary amine.

The cleaving of the one or more peptides from the pro-C-peptide polypeptide-oligomer conjugate to provide the C-peptide polypeptide-oligomer conjugate can be performed by various processes as will be understood by those skilled in the art. The cleaving of the one or more peptides from the pro-C-peptide polypeptide-oligomer conjugate comprises contacting the pro-C-peptide polypeptide-oligomer conjugate with one or more enzymes that are capable of cleaving the bond(s) between the one or more peptides and the C-peptide polypeptide under conditions sufficient to cleave the one or more peptides from the pro-C-peptide polypeptide-oligomer conjugate. As described in various references, for example, Kemmler et al. "Studies on the Conversion of Proinsulin to Insulin," *J. Biol. Chem.*, 246: 6786–6791 (1971), one skilled in the art will understand how to select appropriate enzymes in view of the particular peptide bond(s) to be cleaved and how to provide conditions sufficient to cleave the one or more peptides from the pro-C-peptide polypeptide-oligomer conjugate. The one or more enzymes can comprise various enzymes including, but not limited to, trypsin, chymotrypsin, carboxy peptidase B, and mixtures thereof. In some embodiments, the one or more enzymes can be trypsin, carboxy peptidase B, and mixtures thereof.

In one embodiment, the present invention provides a method of synthesizing an insulin polypeptide-oligomer conjugate comprising:

(a) contacting a proinsulin polypeptide with an oligomer comprising a hydrophilic moiety and/or a lipophilic moiety under conditions sufficient to couple the oligomer to the proinsulin polypeptide and provide a proinsulin polypeptide-oligomer conjugate, wherein the proinsulin polypeptide comprises:
  (i) an insulin polypeptide; and
  (ii) one or more non-insulin polypeptides coupled to the insulin polypeptide by peptide bond(s) capable of being cleaved to yield the insulin polypeptide; and
(b) cleaving the one or more non-insulin polypeptides from the proinsulin polypeptide-oligomer conjugate to provide the insulin polypeptide-oligomer conjugate. Enhanced activity relative to insulin is present, for example, when administration produces a glucose lowering effect that is greater than the glucose lowering effect of a corresponding amount of insulin.

In the methods of this invention, the proinsulin polypeptide can comprise multiple conjugation sites; and a proinsulin polypeptide-oligomer comprising multiple oligomers can be produced and/or the proinsulin polypeptide can comprise one or more conjugation sites on the insulin polypeptide portion thereof, and a proinsulin polypeptide-oligomer comprising one or more oligomers on the insulin polypeptide portion thereof can be produced. In another embodiment, the methods of this invention can comprise a proinsulin polypeptide-oligomer conjugate wherein one or more of the non-insulin polypeptide(s) are unconjugated.

A proinsulin polypeptide of the methods of this invention can comprise at least one conjugation site on the insulin polypeptide portion thereof; and at least one conjugation site on one or more non-insulin polypeptide portions thereof; and a proinsulin polypeptide-oligomer can be produced that can comprise at least one oligomer coupled to the insulin polypeptide portion thereof; and at least one oligomer coupled to one or more of the non-insulin polypeptide portion(s) thereof.

The methods of this invention can further comprise contacting the oligomer with an activating agent under conditions sufficient to provide an activated oligomer capable of coupling to a nucleophilic functionality on the proinsulin polypeptide; and contacting the activated oligomer with the proinsulin polypeptide under conditions sufficient to provide the proinsulin polypeptide-oligomer conjugate. In certain embodiments, the methods of this invention can be performed in situ.

In some embodiments of the methods of this invention, the molar ratio of activated oligomer to proinsulin polypeptide can be greater than about 1:1, greater than about 3:1, and/or greater than about 4:1.

The oligomer in the methods of this invention can comprise a polyethylene glycol moiety and in some embodiments, the oligomer can consist essentially of a polyethylene glycol moiety.

In the methods of this invention, the insulin polypeptide can comprise an A-chain polypeptide and a B-chain polypeptide, and can comprise one or more non-insulin polypeptides that comprise a connecting peptide coupled at a first end to the C-terminus of the B-chain polypeptide and coupled at a second end to the N-terminus of the A-chain polypeptide. In some embodiments, the B-chain can comprise a conjugation site at B29, and the insulin polypeptide-oligomer conjugate can be conjugated at the B29 conjugation site. IN other embodiments, the proinsulin polypeptide can have a single lysine at B29, and the insulin polypeptide-oligomer conjugate can be a B29 monoconjugate. In still additional embodiments, the connecting peptide can be a C-peptide polypeptide, which can comprise a lysine, and the methods of this invention can produce a proinsulin polypeptide-oligomer in which the lysine(s) of the C-peptide polypeptide are coupled to oligomer(s). In other embodiments, the connecting peptide can be devoid of lysine residues.

Also in the methods of this invention, the proinsulin polypeptide can comprise a leader peptide coupled to the N-terminus of the B-chain polypeptide and the leader peptide can comprise a lysine, and a proinsulin polypeptide-oligomer in which the lysine(s) of the leader peptide are coupled to oligomer(s) can be produced. In some embodiments, the leader peptide can be devoid of lysine residues.

In some embodiments of the methods of this invention, a proinsulin polypeptide-oligomer comprising an oligomer coupled at an N-terminus of the leader peptide can be produced and in some embodiments, the one or more or more non-insulin polypeptides can comprise a leader peptide coupled to the N-terminus of the B-chain polypeptide. The leader peptide can comprise a lysine and a proinsulin polypeptide-oligomer in which the lysine(s) of the C-peptide are coupled to oligomer(s) can be produced. In other embodiments, the leader peptide can be devoid of lysine residues.

In other embodiments of the methods of this invention, the proinsulin polypeptide can comprise an A-chain polypeptide and a B-chain polypeptide, and the C-terminus of the B-chain polypeptide can be coupled to the N-terminus of the A-chain polypeptide.

In some embodiments of the methods of this invention, the proinsulin polypeptide can be coupled at the N-terminus of the B-chain to a leader peptide by a cleavable peptide bond. In other embodiments, the insulin polypeptide can be insulin and the oligomer can be coupled to the lysine at the B29 position of the insulin.

In yet other embodiments of the methods of this invention, the insulin polypeptide can be an insulin analog which can be, but is not limited to, $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; $Ala^{B28}$ $Pro^{B29}$ insulin, human.

In various embodiments of the methods of this invention, the insulin polypeptide-oligomer conjugate can be amphiphilically balanced and/or the oligomer can be present as a substantially monodispersed mixture and/or the oligomer can be present as a monodispersed mixture.

In some embodiments of the methods of this invention, the hydrophilic moiety of the oligomer can be a polyalkylene glycol moiety and/or the polyalkylene glycol moiety can be a polyethylene glycol moiety. The polyalkylene glycol moiety can have between 1 and 50 polyalkylene glycol subunits, between 3 and 50 polyalkylene glycol subunits, between 2 and 10 polyalkylene glycol subunits, between 4 and 10 polyalkylene glycol subunits, and/or least 2 polyalkylene glycol subunits.

In some embodiments of the methods of this invention, the lipophilic moiety can be an alkyl or fatty acid moiety and the lipophilic moiety can have between 1 and 28 carbon atoms, between 2 and 24 carbon atoms, between 3 and 18 carbon atoms, between 4 and 12 carbon atoms, between 5 and 7 carbon atoms, and/or between 4 and 14 carbon atoms.

In various embodiments of the methods of this invention, cleavage of one or more non-insulin polypeptides from the proinsulin polypeptide-oligomer conjugate can comprise contacting the proinsulin polypeptide-oligomer conjugate with one or more enzymes that are capable of cleaving the bond(s) between the one or more non-insulin polypeptides and the insulin polypeptide under conditions sufficient to cleave the one or more non-insulin polypeptides from the proinsulin polypeptide-oligomer conjugate. The one or more enzymes can be, for example, trypsin, carboxy peptidase B, and/or mixtures thereof.

In some embodiments of the methods provided herein, the connecting peptide can have a terminal amino acid residue at the first end, and cleavage of the connecting peptide from the proinsulin polypeptide-oligomer conjugate can comprise contacting the proinsulin polypeptide-oligomer conjugate with a first enzyme under conditions sufficient to provide a terminal amino acid residue-insulin polypeptide-oligomer conjugate; and contacting the terminal amino acid residue-insulin polypeptide-oligomer conjugate with a second enzyme under conditions sufficient to provide the insulin polypeptide-oligomer conjugate. The terminal amino acid residue can be an arginine residue, the insulin polypeptide can be insulin, and the connecting peptide can be human C-peptide. In these embodiments, the contacting of the proinsulin polypeptide-oligomer conjugate with a first enzyme and the contacting of the terminal amino acid residue-insulin polypeptide-oligomer conjugate with a second enzyme can occur substantially concurrently. Furthermore, the first enzyme and the second enzyme can be provided in a mixture comprising the first enzyme and the second enzyme and in some embodiments, the first enzyme can be trypsin, and the second enzyme can be carboxy peptidase B.

The methods of this invention can further comprise chemically modifying one or more of the oligomer(s) of the insulin polypeptide-oligomer conjugate, activating one or more of the oligomer(s) of the insulin polypeptide-oligomer conjugate, lengthening one or more of the oligomer(s) of the insulin polypeptide-oligomer conjugate and/or shortening one or more of the oligomer(s) of the insulin polypeptide-oligomer conjugate.

In the methods of this invention, the yield of insulin polypeptide-oligomer conjugate can be greater than 75 percent, greater than 85 percent, greater than about 90 percent, greater than 95 percent, and/or greater than 99 percent.

The methods of this invention further comprise a method of synthesizing an insulin polypeptide, comprising synthesizing an insulin polypeptide-oligomer conjugate as described herein and hydrolyzing the oligomer(s) from the polypeptide-oligomer conjugate to yield the insulin polypeptide.

Also provided herein is a method of synthesizing insulin, comprising synthesizing an insulin polypeptide-oligomer conjugate as described herein and hydrolyzing the oligomer(s) from the polypeptide-oligomer conjugate to yield insulin.

In further embodiments, the present invention provides a method of synthesizing an insulin polypeptide-oligomer conjugate comprising: contacting a proinsulin polypeptide comprising an insulin polypeptide coupled to one or more non-insulin polypeptides by peptide bond(s) capable of being cleaved to yield the insulin polypeptide with an oligomer comprising the structure of Formula I:

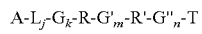 (I)

wherein:
A is an activatable moiety;
L is an optional linker moiety;
G, G' and G" are each optional spacer moieties;
R is a lipophilic moiety and R' is a polyalkylene glycol moiety, or R' is the lipophilic moiety and R is the polyalkylene glycol moiety, and wherein, (i) R and R' are both present, or (ii) R and G are absent and L is coupled to G' if present or to R' if G' is not present, or (iii) R' and G" are absent and T is coupled to G' if present or to R if G' is not present;
T is a terminating moiety; and
j, k, m and n are individually 0 or 1;
under conditions sufficient to couple the oligomer to the insulin polypeptide portion of the proinsulin polypeptide and provide a proinsulin polypeptide-oligomer conjugate; and
(b) cleaving the one or more non-insulin polypeptides from the proinsulin polypeptide-oligomer conjugate to provide the insulin polypeptide-oligomer conjugate.

In certain embodiments of the methods of this invention, R and R' can be both present; R and G can be absent and L can be coupled to G' if present or to R' if G' is not present; R' can be a polyethylene glycol moiety; R' and G" can be absent and T can be coupled to G' if present or to R if G' is not present; A can be —C(O)—OH, C(S)—OH, —C(S)—SH, —OH, —SH, and/or NH$_2$; L can be an alkyl moiety or a fatty acid moiety; G, G' and G" can be individually selected from sugar moieties, cholesterol, and glycerine moieties; and/or T can be alkyl and alkoxy.

In specific embodiments of the methods of this invention, A can be a carboxylic acid moiety; R can be an alkyl moiety having between 3 and 8 carbon atoms; R' can be a polyethylene glycol having between 4 and 10 polyethylene glycol subunits; T can be a lower alkyl or lower alkoxy; and j, k, m and n can be 0. In other embodiments, A can be a carboxylic acid moiety; R can be an alkyl moiety having between 3 and 8 carbon atoms; R' can be a polyethylene glycol having 7 polyethylene glycol subunits; T can be methoxy; and j, k, m and n can be 0.

Further provided in the present invention is a method of synthesizing an insulin polypeptide-oligomer conjugate comprising: contacting a proinsulin polypeptide comprising an insulin polypeptide coupled to one or more non-insulin polypeptides by peptide bond(s) capable of being cleaved to yield the insulin polypeptide with an oligomer comprising the structure of Formula II:

 (II)

wherein:
A is —C(O)—OH, C(S)—OH, —C(S)—SH, —OH, —SH, or NH$_2$;
X is an oxygen atom or a covalent bond, with the proviso that X is not an oxygen atom when A is —OH;
Y is an ester, an ether, a carbamate, a carbonate, or an amide bonding moiety;
m is between 0 and 30;
n is between 0 and 50;
m and n are not both 0; and
R is an alkyl moiety, a sugar moiety, cholesterol, adamantane, an alcohol moiety, or a fatty acid moiety;
under conditions sufficient to couple the oligomer to the insulin polypeptide portion of the proinsulin polypeptide and provide a proinsulin polypeptide-oligomer conjugate; and cleaving the one or more non-insulin polypeptides from the proinsulin polypeptide-oligomer conjugate to provide the insulin polypeptide-oligomer conjugate.

Also provided is a method of synthesizing an insulin polypeptide-oligomer conjugate comprising: contacting a proinsulin polypeptide comprising an insulin polypeptide coupled to one or more non-insulin polypeptides by peptide bond(s) capable of being cleaved to yield the insulin polypeptide with an oligomer comprising the structure of Formula III:

$$A\text{-}(CH_2)_m(OC_2H_4)_nOR \qquad (III)$$

wherein:

A is —C(O)—OH, C(S)—OH, —C(S)—SH, —OH, —SH, or NH$_2$;

m is between 0 and 25;

n is between 0 and 25;

m and n are not both 0; and

R is alkyl;

under conditions sufficient to couple the oligomer to the insulin polypeptide portion of the proinsulin polypeptide and provide a proinsulin polypeptide-oligomer conjugate; and cleaving the one or more non-insulin polypeptides from the proinsulin polypeptide-oligomer conjugate to provide the insulin polypeptide-oligomer conjugate.

Additionally provided is a method of synthesizing an insulin polypeptide-oligomer conjugate comprising: contacting a proinsulin polypeptide comprising an insulin polypeptide having an A-chain polypeptide and a B-chain polypeptide, which comprises a lysine residue; a connecting peptide coupled at a first end to the C-terminus of the B-chain polypeptide and coupled at a second end to the N-terminus of the A-chain polypeptide; and a leader peptide coupled to the N-terminus of the B-chain polypeptide with an oligomer comprising the structure of Formula IV:

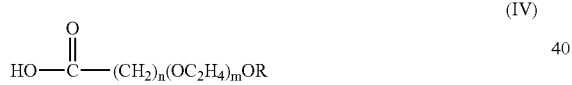

$$\text{HO}-\overset{\overset{\displaystyle O}{\|}}{C}-(CH_2)_n(OC_2H_4)_mOR \qquad (IV)$$

wherein:

m is between 0 and 30;

n is between 0 and 50;

m and n are not both 0; and

R is alkyl;

under conditions sufficient to couple the oligomer to the lysine residue of the B-chain polypeptide of the insulin polypeptide portion of the proinsulin polypeptide and provide a proinsulin polypeptide-oligomer conjugate; and enzymatically cleaving the connecting peptide and the leader peptide from the proinsulin polypeptide-oligomer conjugate to provide the insulin polypeptide-oligomer conjugate.

In the methods described herein, m can be between 3 and 16, between 4 and 14, and/or between 5 and 10. In some embodiments, n can be between 3 and 18, between 4 and 14 and/or between 5 and 10 and R can be a lower alkyl, R can be a C1 to C3 alkyl, and/or R can be a methyl.

The present invention further provides a method of synthesizing an insulin-oligomer conjugate comprising: contacting a proinsulin polypeptide, which comprises proinsulin coupled at its N-terminus to a leader peptide, with an oligomer comprising the structure of Formula V:

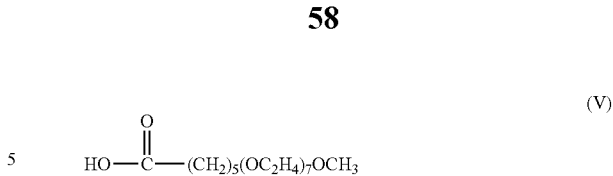

$$\text{HO}-\overset{\overset{\displaystyle O}{\|}}{C}-(CH_2)_5(OC_2H_4)_7OCH_3 \qquad (V)$$

under conditions sufficient to couple the oligomer to the B29 lysine residue of the proinsulin and provide a proinsulin polypeptide-oligomer conjugate; and enzymatically cleaving the C-peptide and the leader peptide from the proinsulin polypeptide-oligomer conjugate to provide the insulin-oligomer conjugate.

In the methods described herein, the enzymatic cleavage of the C-peptide and the leader peptide from the proinsulin polypeptide-oligomer conjugate can comprise contacting the proinsulin polypeptide-oligomer conjugate with a first enzyme under conditions sufficient to provide a (Arg$^{31}$)-insulin-oligomer conjugate; and contacting the (Arg$^{31}$)-insulin polypeptide-oligomer conjugate with a second enzyme under conditions sufficient to provide the insulin polypeptide-oligomer conjugate. The first enzyme can be trypsin and the second enzyme can be carboxy peptidase B.

Also provided herein is a method of synthesizing an insulin polypeptide-acyl oligomer conjugate, comprising enzymatically cleaving one or more non-insulin polypeptides from a proinsulin polypeptide-acyl oligomer conjugate to provide the insulin polypeptide-acyl oligomer conjugate.

In another embodiment, the present invention provides a method of synthesizing an insulin-acyl oligomer conjugate comprising enzymatically cleaving a leader peptide and a C-peptide from a proinsulin polypeptide-acyl oligomer conjugate comprising the following structure:

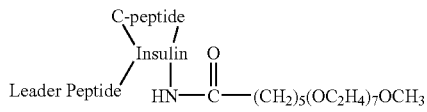

to provide the insulin-acyl oligomer conjugate comprising the following structure:

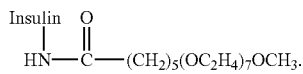

In the methods described herein, the leader peptide can be devoid of lysine residues and/or the enzymatic cleavage of the C-peptide and the leader peptide from the proinsulin polypeptide-acyl oligomer conjugate can comprise contacting the proinsulin polypeptide-oligomer conjugate with a first enzyme under conditions sufficient to provide an (Arg$^{31}$)-insulin-oligomer conjugate; and contacting the (Arg$^{31}$)-insulin polypeptide-oligomer conjugate with a second enzyme under conditions sufficient to provide the insulin polypeptide-oligomer conjugate. The first enzyme can be trypsin and the second enzyme can be carboxy peptidase B.

A method is also provided herein of synthesizing a proinsulin polypeptide-oligomer conjugate comprising contacting a proinsulin polypeptide with an oligomer comprising a hydrophilic moiety and a lipophilic moiety under conditions sufficient to provide the proinsulin polypeptide-oligomer conjugate.

Further provided is a method of synthesizing a C-peptide polypeptide-oligomer conjugate comprising: contacting a pro-C-peptide polypeptide comprising a C-peptide polypeptide coupled to one or more non-insulin polypeptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate; and cleaving the one or more non-insulin polypeptides from the pro-C-peptide polypeptide-oligomer conjugate to provide the C-peptide polypeptide-oligomer conjugate. The C-peptide polypeptide can be C-peptide, the pro-C-peptide polypeptide can be a proinsulin polypeptide, and/or the pro-C-peptide polypeptide can be proinsulin.

It will be appreciated that although the foregoing discussion focuses primarily on pro-X polypeptides and the like, the principles of the invention can be equally applied to the manufacture of other propolypeptides. Thus, for example, the principles of the invention can be applied to pro-X polypeptides, where X can be, but is not limited to, insulin, parathyroid hormone (1–34) (PTH (1–34)), human B-type natriuretic peptide (hBNP), atrial natriuretic peptide (ANP), glucagon-like peptide 1 (GLP 1), luminal cholecystekinin releasing factor (LCRF), C-peptide, leu-enkephalin, met-enkephalin, lysine-leu-enkephalin, as well as any other polypeptide or analog of a polypeptide now known or later identified, for which a pro-polypeptide can be produced and/or a polypeptide can be produced from a pro-polypeptide according to the present invention.

Thus, in one embodiment, the present invention provides a method of synthesizing an X polypeptide-oligomer conjugate. The method generally includes contacting a pro-X polypeptide with an oligomer comprising a hydrophilic moiety and/or a lipophilic moiety. The contacting step generally occurs under conditions sufficient to couple the oligomer to the pro-X polypeptide and provide a pro-X polypeptide-oligomer conjugate. The pro-X polypeptide generally includes an X polypeptide and one or more non-X polypeptides coupled to the X polypeptide by peptide bond(s) capable of being cleaved to yield the X polypeptide. After conjugation, the method generally includes cleaving the one or more non-X polypeptide(s) from the pro-X polypeptide-oligomer conjugate to provide the X polypeptide-oligomer conjugate.

The pro-X polypeptide can include multiple conjugation sites, and a pro-X polypeptide-oligomer comprising multiple oligomers can be produced. The pro-X polypeptide can include one or more conjugation sites on the X polypeptide portion thereof, and a pro-X polypeptide-oligomer comprising one or more oligomers on the X polypeptide portion thereof can be produced. The methods of this invention can also be used to make a pro-X polypeptide-oligomer conjugate wherein one or more of the non-X polypeptide(s) are unconjugated.

The pro-X polypeptide can include at least one conjugation site on the X polypeptide portion thereof. The pro-X polypeptide can include at least one conjugation site on one or more non-X polypeptide portions thereof. A pro-X polypeptide-oligomer can be produced that can include at least one oligomer coupled to the X polypeptide portion thereof; and at least one oligomer coupled to one or more of the non-X polypeptide portion(s) thereof.

The methods of this invention can further include contacting the oligomer with an activating agent under conditions sufficient to provide an activated oligomer capable of coupling to a nucleophilic functionality on the pro-X polypeptide; and contacting the activated oligomer with the pro-X polypeptide under conditions sufficient to provide the pro-X polypeptide-oligomer conjugate. The methods of this invention can be performed in situ.

In some embodiments of the methods of this invention, the molar ratio of activated oligomer to pro-X polypeptide can be greater than about 1:1, greater than about 3:1, and/or greater than about 4:1.

In some embodiments, the oligomer is coupled to the pro-X polypeptide at a conjugation site that is within 1, 2, 3, 4, 5, 6, 7, 8, 9 or 10 amino acids of the site of hydrolysis (counting the last peptide remaining after hydrolysis as being 1 amino acid of the site of hydrolysis).

The oligomers used in the methods of this invention can include a polyethylene glycol moiety and in some embodiments, the oligomer can consist essentially of a polyethylene glycol moiety. The polyethylene glycol moiety can, in some embodiments include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 polyethylene glycol subunits, and can be linear, branched, and/or looped.

In the methods of this invention, the X polypeptide can include two or more polypeptide chains, and can include one or more non-X polypeptides coupled to the polypeptide chains. The polypeptide chains can include conjugation sites, such as amino termini and/or conjugatable functional groups, such as lysine side chains. The X polypeptide-oligomer conjugate can be conjugated at one or more of the conjugation sites. In some embodiments, the pro-X polypeptide can have a single lysine, and the X polypeptide-oligomer conjugate can be a monoconjugate. In still additional embodiments, pro-X polypeptide can include a connecting peptide or a C-peptide polypeptide connecting one or more subunits of the pro-X polypeptide. The methods of this invention can produce a pro-X polypeptide-oligomer in which the lysine(s) of the connecting or C-peptide polypeptide are coupled to oligomer(s). In other embodiments, the connecting peptide or C-peptide can be devoid of lysine residues.

The pro-X polypeptide can include a leader peptide coupled to an N-terminus pf the pro-X polypeptide or a subunit polypeptide thereof. The leader peptide can include one or more lysines, and a pro-X polypeptide-oligomer in which the lysine(s) of the leader peptide are coupled to oligomer(s) can be produced. In some embodiments, the leader peptide can be devoid of lysine residues.

In some embodiments of the methods of this invention, a pro-X polypeptide-oligomer comprising an oligomer coupled at an N-terminus of the leader peptide can be produced. The one or more or more non-X polypeptides can include a leader peptide coupled to an N-terminus of the X polypeptide. The leader peptide can include a lysine and a pro-X polypeptide-oligomer conjugate in which the lysine(s) of the C-peptide are coupled to oligomer(s) can be produced. In other embodiments, the leader peptide can be devoid of lysine residues.

In other embodiments of the methods of this invention, the pro-X polypeptide can include an A-chain polypeptide and a B-chain polypeptide, and the C-terminus of the B-chain polypeptide can be coupled to the N-terminus of the A-chain polypeptide.

In some embodiments of the methods of this invention, the pro-X polypeptide can be coupled at the N-terminus of the B-chain to a leader peptide by a cleavable peptide bond.

In other embodiments, the X polypeptide can be insulin and the oligomer can be coupled to the lysine at the B29 position of the insulin.

The method of the invention can be used to produce conjugated native peptides, as well as conjugated analogs of native peptides.

In various embodiments of the methods of this invention, the X polypeptide-oligomer conjugate can be amphiphilically balanced. The X polypeptide-oligomer can be soluble in organic solvents as well as water. The oligomer can be present as a substantially monodispersed mixture and/or the oligomer can be present as a monodispersed mixture. The hydrophilic moiety of the oligomer can comprise, consist essentially of or consist of a polyalkylene glycol moiety and/or the polyalkylene glycol moiety can be a polyethylene glycol moiety. The polyalkylene glycol moiety can have between 1 and 50 polyalkylene glycol subunits, between 3 and 50 polyalkylene glycol subunits, between 2 and 10 polyalkylene glycol subunits, between 4 and 10 polyalkylene glycol subunits, and/or least 2 polyalkylene glycol subunits.

In some embodiments of the methods of this invention, the lipophilic moiety can be an alkyl or fatty acid moiety and the lipophilic moiety can have between 1 and 28 carbon atoms, between 2 and 24 carbon atoms, between 3 and 18 carbon atoms, between 4 and 12 carbon atoms, between 5 and 7 carbon atoms, and/or between 4 and 14 carbon atoms.

In various embodiments of the methods of this invention, cleavage of one or more non-X polypeptides from the pro-X polypeptide-oligomer conjugate can include contacting the pro-X polypeptide-oligomer conjugate with one or more enzymes that are capable of cleaving the bond(s) between the one or more non-X polypeptides and the X polypeptide under conditions sufficient to cleave the one or more non-X polypeptides from the pro-X polypeptide-oligomer conjugate. The one or more enzymes can be, for example, trypsin, carboxy peptidase B, and/or mixtures thereof.

In some embodiments of the methods provided herein, the connecting peptide can have a terminal amino acid residue at the first end, and cleavage of the connecting peptide from the pro-X polypeptide-oligomer conjugate can include contacting the pro-X polypeptide-oligomer conjugate with a first enzyme under conditions sufficient to provide a terminal amino acid residue-X polypeptide-oligomer conjugate; and contacting the terminal amino acid residue-X polypeptide-oligomer conjugate with a second enzyme under conditions sufficient to provide the X polypeptide-oligomer conjugate. The terminal amino acid residue can be an arginine residue, the X polypeptide can be insulin, and the connecting peptide can be human C-peptide.

The contacting of the pro-X polypeptide-oligomer conjugate with a first enzyme and the contacting of the terminal amino acid residue-X polypeptide-oligomer conjugate with a second enzyme can occur substantially concurrently. Furthermore, the first enzyme and the second enzyme can be provided in a mixture comprising the first enzyme and the second enzyme and in some embodiments, the first enzyme can be trypsin, and the second enzyme can be carboxy peptidase B.

The methods of this invention can further include chemically modifying one or more of the oligomer(s) of the X polypeptide-oligomer conjugate, activating one or more of the oligomer(s) of the X polypeptide-oligomer conjugate, lengthening one or more of the oligomer(s) of the X polypeptide-oligomer conjugate and/or shortening one or more of the oligomer(s) of the X polypeptide-oligomer conjugate.

In the methods of this invention, the yield of X polypeptide-oligomer conjugate can be greater than 75 percent, greater than 85 percent, greater than about 90 percent, greater than 95 percent, and/or greater than 99 percent.

The methods of this invention further include a method of synthesizing an X polypeptide, comprising synthesizing an X polypeptide-oligomer conjugate as described herein and hydrolyzing the oligomer(s) from the polypeptide-oligomer conjugate to yield the X polypeptide.

Also provided herein is a method of synthesizing an X polypeptide, comprising synthesizing an X polypeptide-oligomer conjugate as described herein and hydrolyzing the oligomer(s) from the polypeptide-oligomer conjugate to yield X polypeptide.

Oligomers useful in conjugating pro-X polypeptides include oligomers as described herein, such as oligomers of Formulae I, II, III, IV, V, and VI described above.

According to yet other embodiments of the present invention, a pharmaceutical composition is provided that includes (i) a polypeptide-oligomer conjugate comprising a pro-polypeptide comprising a bioactive polypeptide coupled to a peptide by a peptide bond that is cleavable in vitro or in vivo to yield the bioactive polypeptide and (ii) a pharmaceutically acceptable excipient.

Pharmaceutical compositions comprising a proinsulin polypeptide-oligomer conjugate according to embodiments of the present invention are also provided. The proinsulin polypeptide-oligomer conjugates described above may be formulated for administration in a pharmaceutical carrier in accordance with known techniques. See, e.g., Remington, *The Science And Practice of Pharmacy* ($9^{th}$ Ed. 1995).

In the manufacture of a pharmaceutical composition according to embodiments of the present invention, the propolypeptide-oligomer conjugate is typically admixed with, inter alia, a pharmaceutically acceptable carrier. The carrier must, of course, be acceptable in the sense of being compatible with any other ingredients in the pharmaceutical composition and should not be deleterious to the subject. The carrier may be a solid or a liquid, or both, and is preferably formulated with the propolypeptide-oligomer conjugate as a unit-dose formulation, for example, a tablet, which may contain from about 0.01 or 0.5% to about 95% or 99% by weight of the propolypeptide-oligomer conjugate. The pharmaceutical compositions may be prepared by any of the well-known techniques of pharmacy including, but not limited to, admixing the components, optionally including one or more accessory ingredients.

In some embodiments, the propolypeptide is proinsulin, a proinsulin analog, a proinsulin fragment, a proinsulin fragment analog, preproinsulin, a preproinsulin analog, a preproinsulin fragment, or a preproinsulin fragment analog and the treatable condition is an insulin deficiency, such as Type I or Type II diabetes.

The present invention further provides pharmaceutical compositions comprising the insulin-oligomer and/or C-peptide oligomer conjugates and/or insulin propeptide-oligomer conjugates of this invention in a pharmaceutically acceptable carrier and methods of administering said pharmaceutical compositions to a subject to treat an insulin deficiency or a disorder associated with an insulin deficiency.

As used herein, a "pharmaceutically acceptable carrier" according to the present invention is a component such as a carrier, diluent, or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects (such as toxicity, irritation, allergic response, and death). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents.

Pharmaceutical compositions according to embodiments of the present invention can include various suitable excipients as will be understood by those skilled in the art, such as those found in the *National Formulary* 19, pages 2404–2406 (2000), the disclosure of pages 2404 to 2406 being incorporated herein by reference in their entirety for these teachings. For example, the pharmaceutical compositions can include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols and inert fillers can also be used. Examples of polyols include, but are not limited to, mannitol, sorbitol, xylitol, sucrose, maltose, glucose, lactose, dextrose, and the like. Other inert fillers that can be used encompass those that are known in the art and are useful in the manufacture of various dosage forms. If desired, the solid formulations can include other components such as bulking agents and/or granulating agents, and the like. The drug products of the invention can be formulated so as to provide quick, sustained, or delayed release of the active ingredient after administration to a subject by employing procedures well known in the art.

The present invention also provides pharmaceutical compositions according to embodiments of the present invention that include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular insulin drug-oligomer conjugate which is being used.

Pharmaceutical compositions suitable for oral administration can be presented in discrete units, such as capsules, cachets, lozenges, or tables, each containing a predetermined amount of the insulin drug-oligomer conjugates; as a powder or granules; as a solution or a suspension in an aqueous or non-aqueous liquid; or as an oil-in-water or water-in-oil emulsion. Such formulations can be prepared by any suitable method of pharmacy that includes the step of bringing into association the insulin drug-oligomer conjugate and a suitable carrier (which can contain one or more accessory ingredients as noted above). In general, the pharmaceutical composition according to embodiments of the present invention are prepared by uniformly and intimately admixing the insulin drug-oligomer conjugate with a liquid or finely divided solid carrier, or both, and then, if necessary, shaping the resulting mixture.

In some embodiments of the present invention, the pharmaceutical composition is a liquid pharmaceutical composition suitable for oral administration. When the pharmaceutical composition is a liquid pharmaceutical composition, the composition can include a buffering agent as described above. Liquid pharmaceutical compositions according to embodiments of the present invention have a pH that is physiologically compatible. Liquid pharmaceutical compositions according to embodiments of the present invention can have a pH that is between 6.2 and 9.0. In some embodiments, liquid pharmaceutical compositions according to embodiments of the present invention have a pH that is between a lower limit of 6.3, 6.4, 6.5, 6.6, 6.7, 6.8, 6.9, 7.0, 7.1, 7.2, 7.3, 7.4, 7.5, 7.6, or 7.7 and an upper limit of 7.9, 8.0, 8.1, 8.2, 8.3, 8.4, 8.5, 8.6, 8.7, 8.8, or 8.9. In some embodiments, liquid pharmaceutical compositions according to embodiments of the present invention have a pH that is between 7.0 and 8.5. In other embodiments, liquid pharmaceutical compositions according to embodiments of the present invention have a pH that is between 7.4 and 8.2.

In other embodiments of the present invention, the pharmaceutical composition is a solid pharmaceutical composition suitable for oral administration. The solid pharmaceutical composition can be prepared by various methods as will be understood by those skilled in the art. For example, a tablet can be prepared by compressing or molding a powder or granules containing the insulin drug-oligomer conjugate, optionally with one or more accessory ingredients. Compressed tablets can be prepared by compressing, in a suitable machine, the mixture in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Pharmaceutical compositions suitable for buccal (sub-lingual) administration include lozenges comprising the insulin drug-oligomer conjugate in a flavored base, usually an artificial sweetener and acacia or tragacanth; and pastilles comprising the insulin drug-oligomer conjugate in an inert base such as gelatin and glycerin or sucrose and acacia.

Pharmaceutical compositions according to embodiments of the present invention suitable for parenteral administration can comprise sterile aqueous and non-aqueous injection solutions comprising the insulin drug-oligomer conjugate, which preparations can be isotonic with the blood of the intended recipient. These preparations can contain antioxidants, buffers, bacteriostats and solutes that render the composition isotonic with the blood of the intended recipient. Aqueous and non-aqueous sterile suspensions can include suspending agents and thickening agents. The compositions can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition comprising the insulin drug-oligomer conjugate in a unit dosage form in a sealed container can be provided. The insulin drug-oligomer conjugate is provided in the form of a lyophilizate which is capable of being reconstituted with a suitable pharmaceutically acceptable carrier to form a liquid composition suitable for injection thereof into a subject.

Pharmaceutical compositions according to the present invention can further comprise a buffering component. The buffering component can comprise various buffering agents as will be understood by those skilled in the art. Exemplary buffering agents include, but are not limited to, inorganic acids (e.g., phosphoric acid), organic acids (e.g., citric acid), organic bases (e.g., tris-base (tris(hydroxymethyl)aminomethane), trolamine (triethanolamine), or histadine), and mixtures thereof. The buffering component can comprise an organic base, and can comprise tris-base, trolamine, or a mixture thereof. In some embodiments, the buffering component comprises an organic acid and an organic base, and can comprise citric acid and tris-base, trolamine, or a mixture thereof. The buffering agent can be present in an amount that will buffer the pharmaceutical composition against the acidic environment that may be experienced in the gut as will be understood by one skilled in the art.

The unit dosage form of the compositions of this invention can range from about 1.0 µg to about 10 grams of the insulin drug-oligomer conjugate. When the insulin drug-oligomer conjugate is substantially water-insoluble, a sufficient amount of emulsifying agent that is physiologically acceptable can be employed in sufficient quantity to emulsify the insulin drug-oligomer conjugate in an aqueous carrier. One such useful emulsifying agent is phosphatidyl choline.

Pharmaceutical compositions suitable for rectal administration can be presented as unit dose suppositories. These can be prepared by admixing the insulin drug-oligomer conjugate with one or more conventional solid carriers, for example, cocoa butter, and then shaping the resulting mixture.

Pharmaceutical compositions suitable for topical application to the skin can take the form of an ointment, cream, lotion, paste, gel, spray, aerosol, transdermal patch or oil. Carriers that can be used include, but are not limited to, petroleum jelly, lanoline, polyethylene glycols, alcohols, transdermal enhancers, and combinations of two or more thereof.

Pharmaceutical compositions suitable for transdermal administration can be presented as discrete patches adapted to remain in intimate contact with the epidermis of the recipient for a prolonged period of time. Compositions suitable for transdermal administration can also be delivered by iontophoresis (see, for example, *Pharmaceutical Research* 3 (6):318 (1986)) and typically take the form of an optionally buffered aqueous solution of the insulin drug-oligomer conjugate. Suitable formulations comprise citrate or bis\tris buffer (pH 6) or ethanol/water and can contain, for example, from 0.1 to 0.2M active ingredient.

Methods of treating an insulin deficiency and/or disorders associated with an insulin deficiency in a subject in need of such treatment by administering a therapeutically effective amount of any of the various pharmaceutical compositions of the present invention are also provided. The effective amount of the insulin drug-oligomer conjugate, the use of which is in the scope of present invention, will vary somewhat from conjugate to conjugate, and subject to subject, and will depend, for example, upon factors such as the age and condition of the subject, the severity of the condition to be treated and/or the route of delivery. An appropriate "therapeutically effective amount" in any individual case can be determined by one of ordinary skill in the art by reference to the pertinent texts and literature and/or by using routine experimentation. (See, for example, Remington, *The Science And Practice of Pharmacy* ($9^{th}$ Ed. 1995). A therapeutically effective amount of the pharmaceutical compositions of this invention can include those amounts that result in, or maintain, blood glucose levels in a normal range, as would be well known to one skilled in the art.

A subject of this invention can be any animal that produces insulin and is therefore susceptible to insulin deficiency and/or disorders related to a deficiency of insulin and that would be able to be treated with the compositions of this invention. The subject can be any mammal and the mammal can be a human.

Methods of treating a condition treatable by a bioactive polypeptide in a subject in need of such treatment are also provided herein that include administering to the subject an effective amount of a propolypeptide-oligomer conjugate, which conjugate comprises the bioactive polypeptide coupled to a peptide by a peptide bond that is cleavable in vivo to yield the bioactive polypeptide, and an oligomer coupled to the bioactive polypeptide portion of the propolypeptide are also provided.

As an example, a dosage of from about 1.0 µg/kg to about 50 mg/kg, including any dosage range between these values, will have therapeutic efficacy, with all weights being calculated based upon the weight of the insulin and/or the insulin drug-oligomer conjugate. Toxicity concerns at the higher level may restrict intravenous dosages to a lower level such as up to about 10 mg/kg, with all weights being calculated based upon the weight of the active base. A dosage of from about 10 mg/kg to about 50 mg/kg can be employed for oral administration. Typically, a dosage of from about 0.5 mg/kg to 5 mg/kg can be employed for intramuscular injection. The frequency of administration can be, for example, one, two, three or more times per day or as necessary to control the condition. Control of the condition and efficacy of the treatment can be readily determined by those skilled in the art of studying and/or treating insulin deficiencies and/or related disorders. Alternatively, the pharmaceutical compositions of this invention can be administered by continuous infusion. The duration of treatment depends on the type of insulin deficiency being treated and can be for as long as the life of the subject.

The present invention will now be described with reference to the following examples. It should be appreciated that these examples are for the purposes of illustrating aspects of the present invention, and do not limit the scope of the invention as defined by the claims.

EXAMPLES

Example 1

Synthesis of 6-(2-{2-[2-(2-{2-[2-(2-methoxyethoxy)ethoxy]-ethoxy}-ethoxy)-ethoxy]-ethoxy}-ethoxy)-hexanoic acid 2,5-dioxo-pyrrolidin-1-yl ester (8)

Hexaethylene Glycol Monobenzyl Ether (1). An aqueous sodium hydroxide solution prepared by dissolving 3.99 g (100 mmol) NaOH in 4 ml water was added slowly to monodispersed hexaethylene glycol (28.175 g, 25 ml, 100 mmol). Benzyl chloride (3.9 g, 30.8 mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of monodispersed compound 1 as a yellow oil.

Ethyl 6-methylsulfonyloxyhexanoate (2). A solution of monodispersed ethyl 6-hydroxyhexanoate (50.76 ml, 50.41 g, 227 mmol) in dry dichloromethane (75 ml) was chilled in an ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated NaHCO$_3$, water and brine. The organics were dried over Na$_2$SO$_4$, filtered and concentrated in vacuo to a pale yellow oil. Final purification of the crude product was achieved by flash chromatography (silica gel, 1/1 hexanes/ethyl acetate) to give the monodispersed compound 2 (46.13 g, 85%) as a clear, colorless oil. FAB MS: m/e 239 (M+H), 193 (M-C$_2$H$_5$O).

6-{2-[2-(2-{2-[2-(2-Benzyloxyethoxy)ethoxy]ethoxy}-ethoxy)-ethoxy]-ethoxy}-hexanoic acid ethyl ester (3). Sodium hydride (3.225 g or a 60% oil dispersion, 80.6 mmol) was suspended in 80 ml of anhydrous toluene, placed under a nitrogen atmosphere and cooled in an ice bath. A solution of the monodispersed alcohol 9 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The monodispersed mesylate 10 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the monodispersed compound 3 as a pale yellow oil (16.52 g, 44%). FAB MS: m/e 515 (M+H).

6-{2-[2-(2-{2-[2-(2-hydroxyethoxy)ethoxy]ethoxy}-ethoxy)-ethoxy]-ethoxy}-hexanoic acid ethyl ester (4). Substantially monodispersed benzyl ether 3 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the monodispersed compound 4 as a clear oil (0.67 g, 79%). FAB MS: m/e 425 (M+H), 447 (M+Na).

6-{2-[2-(2-{2-[2-(2-methylsulfonylethoxy)ethoxyl] ethoxy}-ethoxy)-ethoxy]-ethoxy}-hexanoic acid ethyl ester (5). The monodispersed alcohol 4 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated NaHCO$_3$, water and brine. The organics were dried over Na$_2$SO$_4$, filtered and concentrated in vacuo. The residue was purified by column chromatography (silica gel, 9/1 ethyl acetate/methanol) to give monodispersed compound 5 as a clear oil (0.819 g, 83%). FAB MS: m/e 503 (M+H).

6-(2-{2-[2-(2-{2-[2-(2-methoxyethoxy)ethoxy]-ethoxy}-ethoxy)-ethoxy]-ethoxy }-ethoxy)-hexnoic acid ethyl ester (6). NaH (88 mg of a 60% dispersion in oil, 2.2 mmol) was suspended in anhydrous toluene (3 ml) under N$_2$ and chilled to 0° C. Monodispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy gray suspension became clear and yellow and then turned brown. Mesylate 5 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the monodispersed compound 6 as a clear yellow oil (0.302 g 57%). FAB MS: m/e 527 (M+H), 549 (M+Na).

6-(2-{2-[2-(2-{2-[2-(2-methoxyethoxy)ethoxy]-ethoxy}-ethoxy)-ethoxy]-ethoxy }-hexanoic acid (7). Monodispersed ester 6 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml×2), dried over Na$_2$SO$_4$, filtered and concentrated in vacuo to yield the monodispersed compound 15 as a yellow oil (0.147 g, 62%). FAB MS: m/e 499 (M+H), 521 (M+Na).

6-(2-{2-[2-(2-{2-[2-(2-methoxyethoxy)ethoxy]-ethoxy}-ethoxy)-ethoxy]-ethoxy }-hexanoic acid 2,5-dioxo-pyrrolidin-1-yl ester (8). Monodispersed acid 7 (0.209 g, 0.42 mmol) was dissolved in 4 ml of dry dichloromethane and added to a dry flask already containing NHS (N-hydroxysuccinimide) (57.8 mg, 0.502 mmol) and EDC (1-(3-dimethylaminopropyl)-3-ethylcarbodiimide hydrochloride) (98.0 mg, 0.502 mmol) under a N$_2$ atmosphere. The solution was stirred at room temperature overnight and filtered through silica gel to remove excess reagents and the urea formed from the EDC. The filtrate was concentrated in vacuo to provide the activated monodispersed oligomer 8 as a dark yellow oil (0.235 g, 94%). FAB MS: m/e 596 (M+H), 618 (M+Na).

Example 2

Synthesis of Activated MPEG$_7$-C$_8$ (14)

Mesylate of triethylene glycol monomethyl ether (9). To a solution of CH$_2$Cl$_2$ (100 mL) cooled to 0° C. in an ice bath was added monodispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL CH$_2$Cl$_2$). The reaction mixture was stirred for 30 min at 0° C., allowed to warm to room temperature, and then stirred for 2 h. The crude reaction mixture was filtered through Celite (washed CH$_2$Cl$_2$~200 mL), then washed with H$_2$O (300 mL), 5% NaHCO$_3$ (300 mL), H$_2$O (300 mL), sat. NaCl (300 mL), dried MgSO$_4$, and evaporated to dryness. The oil was then placed on a vacuum line for ~2 h to ensure dryness and afforded the monodispersed compound 9 as a yellow oil (29.15 g, 80% yield).

Heptaethylene glycol monomethyl ether (10). To a solution of monodispersed tetraethylene glycol (51.5 g, 0.27 mol) in THF (1L) was added potassium t-butoxide (14.8 g, 0.13 mol, small portions over ~30 min). The reaction mixture was then stirred for 1 h and then 9 (29.15 g, 0.12 mol) dissolved in THF (90 mL) was added dropwise and the reaction mixture was stirred overnight. The crude reaction mixture was filtered through Celite (washed $CH_2Cl_2$, ~200 mL) and evaporated to dryness. The oil was then dissolved in HCl (250 mL, 1 N) and washed with ethyl acetate (250 mL) to remove excess 9. Additional washings of ethyl acetate (125 mL) may be required to remove remaining 9. The aqueous phase was washed repetitively with $CH_2Cl_2$ (125 mL volumes) until most of the compound 18 has been removed from the aqueous phase. The first extraction will contain 9, 10, and dicoupled side product and should be back extracted with HCl (125 mL, 1N). The organic layers were combined and evaporated to dryness. The resultant oil was then dissolved in $CH_2Cl_2$ (100 mL) and washed repetitively with $H_2O$ (50 mL volumes) until 10 was removed. The aqueous fractions were combined, total volume 500 mL, and NaCl was added until the solution became cloudy and then was washed with $CH_2Cl_2$ (2×500 mL). The organic layers were combined, dried $MgSO_4$, and evaporated to dryness to afford the monodispersed compound 10 as an oil (16.9 g, 41% yield). It may be desirable to repeat one or more steps of the purification procedure to ensure high purity.

8-Bromooctoanate (11). To a solution of monodispersed 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil 11 (5.5 g, 98% yield).

$MPEG_7$-$C_8$ ester (12). To a solution of the monodispersed compound 10 (3.0 g, 8.8 mmol) in ether (90 mL) was added potassium t-butoxide (1.2 g, 9.6 mmol) and the reaction mixture was stirred for 1 h. Then dropwise addition of the monodispersed compound 11 (2.4 g, 9.6 mmol), dissolved in ether (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the monodispersed compound 12 as a clear oil (0.843 g, 19% yield).

$MPEG_7$-$C_8$ acid (13). To the oil of the monodispersed compound 12 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the monodispersed compound 13 as a clear oil (0.35 g, 53% yield).

Activation of $MPEG_7$-$C_8$ acid. Monodispersed mPEG7-C8-acid 13 (0.3 1g, 0.64 mmol) was dissolved in 3 ml of anhydrous methylene chloride and then solution of N-hydroxysuccinimide (0.079 g, 0.69 mmol) and EDCI.HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford monodispersed activated $MPEG_7$-$C_8$ 14 as a clear oil and dried via vacuum.

Example 3

Synthesis of Activated $MPEG_7$-$C_{10}$ (19)

10-hydroxydecanoate (15). To a solution of monodispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the monodispersed compound 15 as a clear oil (6.9 g, 98% yield).

Mesylate of 10-hydroxydecanoate (16). To a solution of $CH_2Cl_2$ (27 mL) was added monodispersed 10-hydroxydecanoate 15 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the monodispersed compound 16 as a yellowish oil (7.42 g, 97% yield).

$MPEG_7$-$C_{10}$ ester (17). To a solution of substantially monodispersed heptaethylene glycol monomethyl ether 10 (2.5 g, 7.3 mmol) in tetrahydrofuran (100 mL) was added sodium hydride (0.194 g, 8.1 mmol) and the reaction mixture was stirred for 1 h. Then dropwise addition of mesylate of monodispersed 10-hydroxydecanoate 16 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the monodispersed compound 17 as a clear oil (0.570 g, 15% yield).

$MPEG_7$-$C_{10}$ acid (18). To the oil of monodispersed $mPEG_7$-$C_{10}$ ester 17 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the monodispersed compound 18 as a clear oil (0.340 g, 62% yield).

Activation of $MPEG_7$-$C_{10}$ acid. The monodispersed acid 18 was activated using procedures as described herein to provide activated $MPEG_7$-$C_{10}$ Oligomer 19.

Example 4

Synthesis of Activated $C_{18}(PEG_6)$ Oligomer (22)

Synthesis of $C_{18}(PEG_6)$ Oligomer (20). Monodispersed stearoyl chloride (0.7 g, 2.31 mmol) was added slowly to a mixture of monodispersed $PEG_6$ (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over MgSO$_4$, concentrated and dried via vacuum. Purified monodispersed compound 20 was analyzed by FABMS: m/e 549/M$^+$H.

Activation of C$_{18}$(PEG$_6$) Oligomer. Activation of monodispersed C$_{18}$(PEG$_6$) oligomer was accomplished in two steps:

1) Monodispersed stearoyl-PEG$_6$ 20 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining substantially monodispersed stearoyl PEG6 chloroformate 21 was dried over P$_2$O$_5$ overnight.

2) To a solution of monodispersed stearoyl-PEG$_6$ chloroformate 21 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over MgSO$_4$, filtered, concentrated and dried via vacuum to provide the monodispersed activated C$_{18}$(PEG$_6$) oligomer 22.

Example 5

Synthesis of Activated C$_{18}$(PEG$_8$) Oligomer (28)

Tetraethylene glycol monobenzylether (23). To the oil of monodispersed tetraethylene glycol (19.4 g, 0.10 mol) was added a solution of NaOH (4.0 g in 4.0 mL) and the reaction was stirred for 15 min. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed CH$_2$Cl$_2$ (2×200 mL). The organic layers were combined, washed sat. NaCl, dried MgSO$_4$, and chromatographed (silica, ethyl acetate) to afford the monodispersed compound 23 as a yellow oil (6.21 g, 71% yield).

Mesylate of tetraethylene glycol monobenzylether (24). To a solution of CH$_2$Cl$_2$ (20 mL) was added monodispersed tetraethylene glycol monobenzylether 23 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in CH$_2$Cl$_2$ (2 mL) was added and the reaction mixture was stirred at 0° C. for 30 min, the ice bath was removed and the reaction was stirred for an additional 2 h at room temperature. The crude reaction mixture was filtered through Celite (washed CH$_2$Cl$_2$, 80 mL) and the filtrate was washed H$_2$O (100 mL), 5% NaHCO$_3$ (2×100 mL), H$_2$0 (100 mL), sat. NaCl (100 mL), and dried MgSO$_4$. The resulting yellow oil was chromatographed on a pad of silica containing activated carbon (10 g) to afford the monodispersed compound 24 as a clear oil (7.10 g, 89% yield).

Octaethylene glycol monobenzylether (25). To a solution of tetrahydrofuran (140 mL) containing sodium hydride (0.43 g, 18 mmol) was added dropwise a solution of monodispersed tetraethylene glycol (3.5 g, 18 mmol) in tetrahydrofuran (10 mL) and the reaction mixture was stirred for 1 h. Then mesylate of monodispersed tetraethylene glycol monobenzylether 24 (6.0 g, 16.5 mmol) dissolved in tetrahydrofuran (10 mL) was added dropwise and the reaction mixture was stirred overnight. The crude reaction mixture was filtered through Celite (washed, CH$_2$Cl$_2$, 250 mL) and the filtrate was washed H$_2$O, dried MgSO$_4$, and evaporated to dryness. The resultant oil was chromatographed (silica, ethyl acetate/methanol, 10:1) and chromatographed (silica, chloroform/methanol, 25:1) to afford the monodispersed compound 25 as a clear oil (2.62 g, 34% yield).

Synthesis of Stearate PEG$_8$-Benzyl (26). To a stirred cooled solution of monodispersed octaethylene glycol monobenzylether 25 (0.998 g, 2.07 mmol) and pyridine (163.9 mg, 2.07 mmol) was added monodispersed stearoyl chloride (627.7 mg, 2.07 mmol) in benzene. The reaction mixture was stirred overnight (18 hours). The next day the reaction mixture was washed with water, dried over MgSO$_4$, concentrated and dried via vacuum. Then the crude product was chromatographed on flash silica gel column, using 10% methanol/90% chloroform. The fractions containing the product were combined, concentrated and dried via vacuum to afford the monodispersed compound 26.

Hydrogenolysis of Stearate-PEG$_8$-Benzyl. To a methanol solution of monodispersed stearate-PEG$_8$-Bzl 26 (0.854 g 1.138 mmol) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with R$_f$=0.6 collected, concentrated and dried to provide the monodispersed acid 27.

Activation of C$_{18}$(PEG$_8$) Oligomer. Two step activation of monodispersed stearate-PEG8 oligomer 27 was performed as described for stearate-PEG$_6$ in Example 4 above to provide the monodispersed activated C$_{18}$(PEG$_8$) oligomer 28.

Example 6

Synthesis of Activated Triethylene Glycol Monomethyl Oligomers

A solution of toluene containing 20% phosgene (100 ml, approximately 18.7 g, 189 mmol phosgene) was chilled to 0° C. under a N$_2$ atmosphere. Monodispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the monodispersed mTEG chloroformate as a clear oily residue.

The monodispersed nTEG chloroformate was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil was taken up in dichloromethane and washed twice with cold deionized water, twice with 1N HCl and once with brine. The organics were dried over MgSO$_4$, filtered and concentrated to provide the monodispersed title compound as a clear, light yellow oil. If necessary, the NHS ester could be further purified by flash chromatography on silica gel using EtOAc as the elutant.

Example 7

Synthesis of Activated Palmitate-TEG Oligomers

Monodispersed palmitic anhydride (5 g; 10 mmol) was dissolved in dry THF (20 mL) and stirred at room temperature. To the stirring solution, 3 mol excess of pyridine was added followed by monodispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% $H_2SO_4$ acid and extracted ethyl acetate (3×30 mL). The combined extract was washed sequentially with water, brine, dried over $MgSO_4$, and evaporated to give monodispersed palmitate-TEG oligomers.

A solution of N,N'-disuccinimidyl carbonate (3 mmol) in DMF (~10 mL) is added to a solution of the monodispersed palmitate-TEG oligomers (1 mmol) in 10 mL of anhydrous DMF while stirring. Sodium hydride (3 mmol) is added slowly to the reaction mixture. The reaction mixture is stirred for several hours (e.g., 5 hours). Diethyl ether is added to precipitate the monodispersed activated title oligomer. This process is repeated 3 times and the product is finally dried.

Example 8

Synthesis of Activated Hexaethylene Glycol Monomethyl Oligomers

Monodispersed activated hexaethylene glycol monomethyl ether was prepared analogously to that of monodispersed triethylene glycol as described herein. A 20% phosgene in toluene solution (35 mL, 6.66 g, 67.4 mmol phosgene) was chilled under a $N_2$ atmosphere in an ice/salt water bath. Monodispersed hexaethylene glycol (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving monodispersed methyl hexaethylene glycol chloroformate as a clear, oily residue.

The monodispersed chloroformate was dissolved in 20 mL dry dichloromethane and placed under a dry, inert atmosphere. Triethylamine (0.94 mL, 0.68 g, 6.7 mmol) and then NHS (N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over $Na_2SO_4$, filtered and concentrated. Final purification was done via flash chromatography (silica gel, EtOAc) to obtain the activated monodispersed hexaethylene monomethyl ether.

Example 9

Synthesis of Activated Heptaethylene Glycol Monomethyl Ether

8-Methoxy-1-(methylsulfonyl)oxy-3,6-dioxaoctane (29). A solution of monodispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over $Na_2SO_4$, filtered and concentrated in vacuo to give a monodispersed mixture of compounds 29 as a clear oil (5.31 g, 86%).

Heptaethylene glycol mono methyl ether (30). To a stirred solution of monodispersed tetraethylene glycol (35.7 mmol) in dry DMF (25.7 mL), under $N_2$ was added in portion a 60% dispersion of NaH in mineral oil, and the mixture was stirred at room temperature for 1 hour. To the resulting sodium salt of the tetraethylene glycol was added a solution of monodispersed mesylate 29 (23.36) in dry DMF (4 ml) in a single portion, and the mixture was stirred at room temperature for 3.5 hours. Progress of the reaction was monitored by TLC (12% $CH_3OH$—$CHCl_3$). The reaction mixture was diluted with an equal amount of 1N HCl, and extracted with ethyl acetate (2×20 ml) and discarded. Extraction of aqueous solution and work-up gave monodispersed heptaethylene glycol monomethyl ether 30 (82–84% yield). Oil; Rf 0.46 (methanol:chloroform=3:22); MS m/z calc'd for $C_{15}H_{32}O_8$ 340.21 ($M^+$+1), found 341.2.

Activation of Heptaethylene glycol monomethyl ether. Monodispersed heptaethylene glycol monomethyl ether 30 is activated by a procedure as described herein to activate triethylene glycol monomethyl ether to provide the activated heptaethylene glycol monomethyl ether.

Example 10

Synthesis of Activated Decaethylene Glycol Monomethyl Ether (33)

20-methoxy-1-(methylsulfonyl)oxy-3,6,9,12,15,18-hexaoxaeicosane (31). Monodispersed compound 31 was obtained in quantitative yield from compound 30 and methanesulfonyl chloride as described for 29 herein, as an oil; Rf 0.4 (ethyl acetate: acetonitrile=1:5); MS m/z calc'd for $C_{17}H_{37}O_{10}$ 433.21 ($M^+$+1), found 433.469.

Decaethylene glycol monomethyl ether (32). Monodispersed compound 32 was prepared from compound 31 and monodispersed triethylene glycol using the procedure described herein. Oil; Rf 0.41 (methanol: chloroform=6:10); MS m/z calc'd for $C_{21}H_{44}O_{11}$ 472.29 ($M^+$+1), found 472.29.

Activation of decaethylene glycol monomethyl ether. Monodispersed decaethylene glycol monomethyl ether 32 is activated by a procedure as described herein to activate triethylene glycol monomethyl ether to provide the activated decaethylene glycol monomethyl ether 33.

Example 11

Preparation of Lys$^{B29}$-Oligomer-Conjugated Insulin

Figure 11:
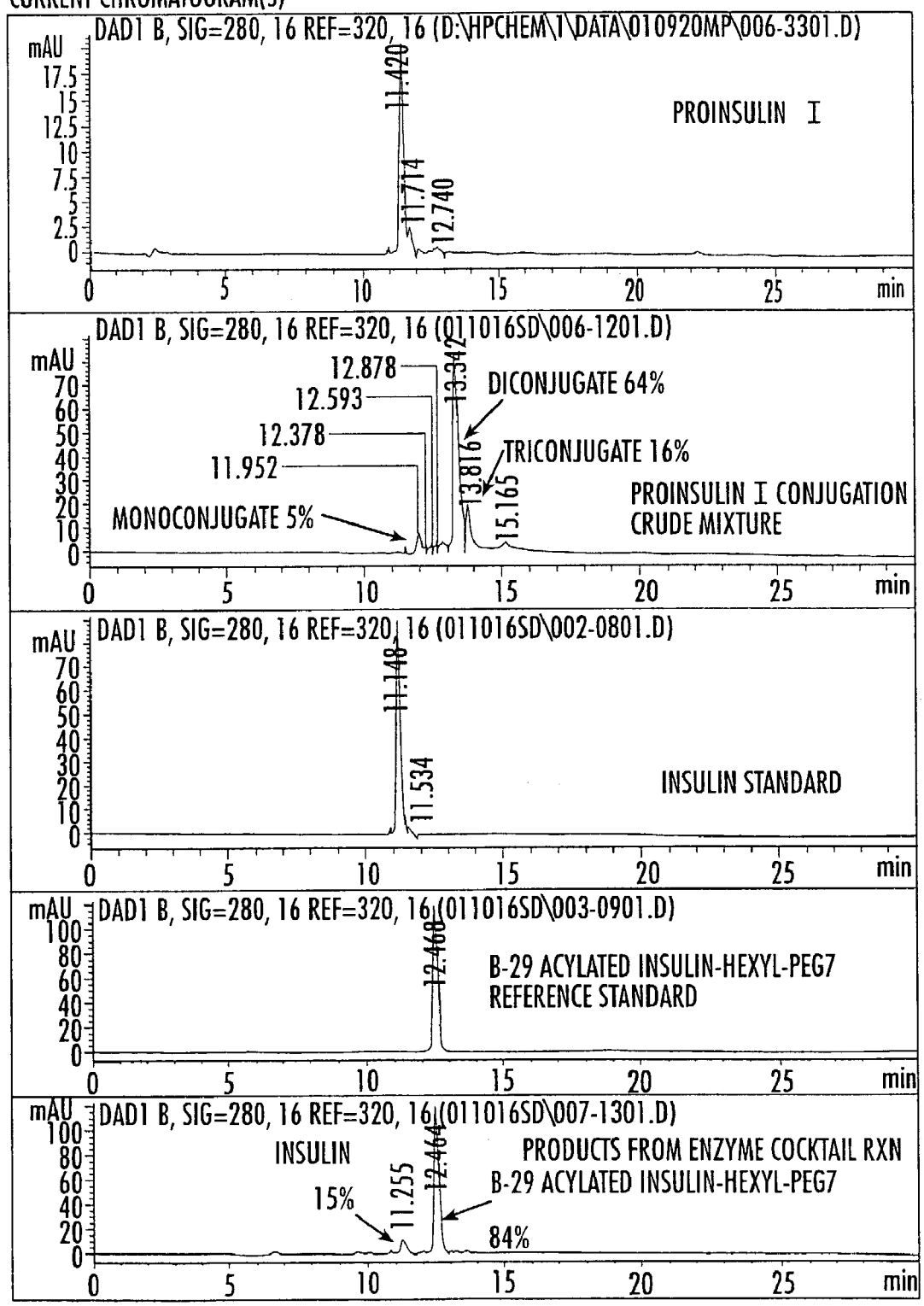
FIG. 11 illustrates an HPLC profile of production of B-29 acylated Insulin-hexyl-PEG7 via proinsulin I.

Conjugation of Recombinant Proinsulin I. Recombinant Proinsulin I (MW 10,642 Daltons) was obtained from Biobras, of Belo Horizonte, Brazil. A 2.32×10$^{-3}$ mmol portion of proinsulin I was dissolved in 10 mL of DMSO. To the solution was added 324 µL of triethylamine. The resulting solution was allowed to stir for 5 minutes, and then a solution of activated methylheptaethylene glycol ((PEG7)-hexyl oligomer) (9.30×10$^{-3}$ mmol) in acetonitrile was added. The course of the conjugation (acylation) reaction was monitored by HPLC. When reaction appeared to be complete, it was quenched by addition of 3.54 mL of 5% aqueous trifluoroacetic acid solution. The reaction mixture was then processed and exchanged into 100 mM Tris-HCl Buffer, pH 7.6. The HPLC profile of the product mixture, oligomer-conjugated recombinant Proinsulin I, is shown in FIG. 11.

Figure 12:
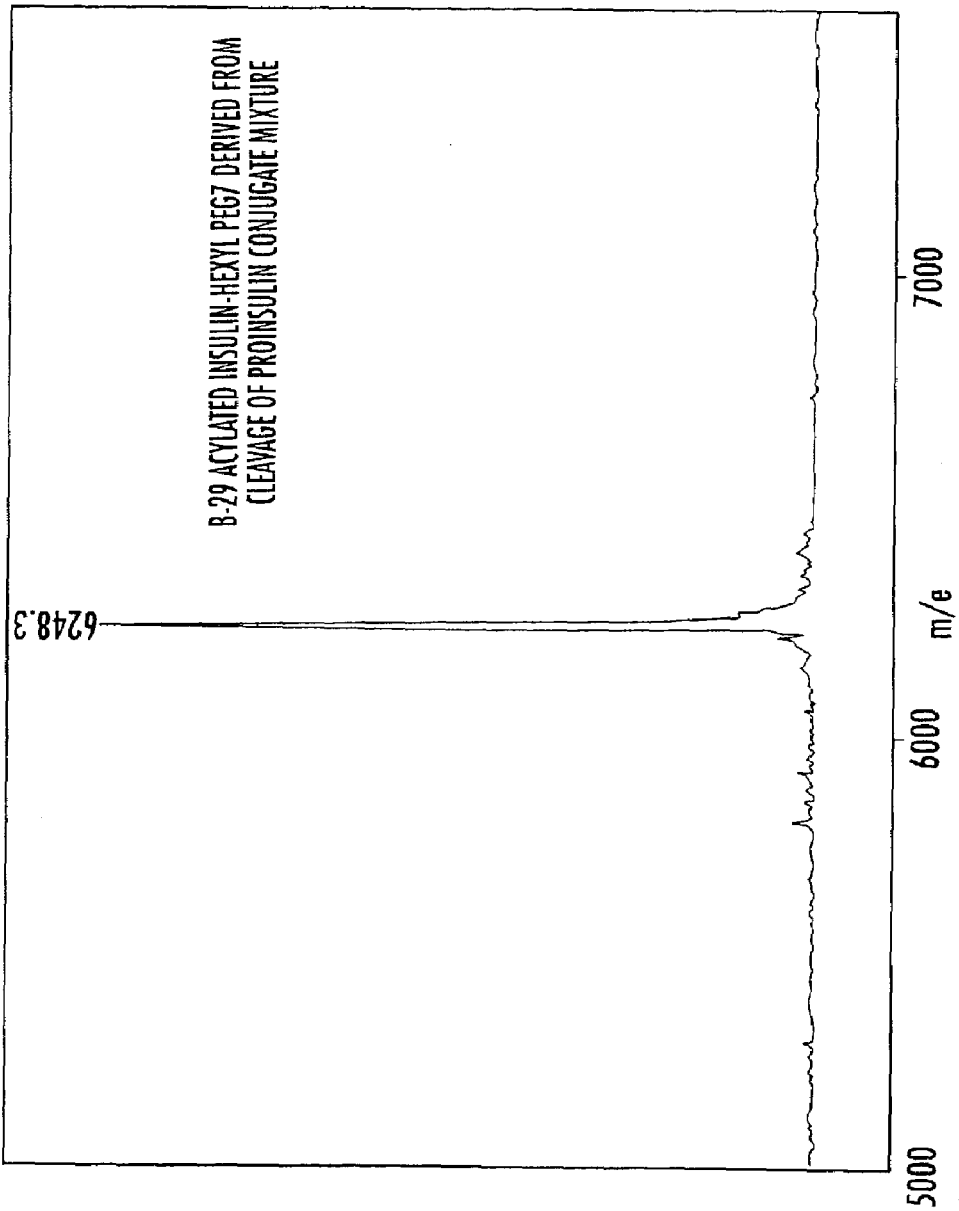
FIG. 12 illustrates an m.s. spectrum of B-29 acylated Insulin-hexyl-PEG7 via proinsulin I.
Figure 13:
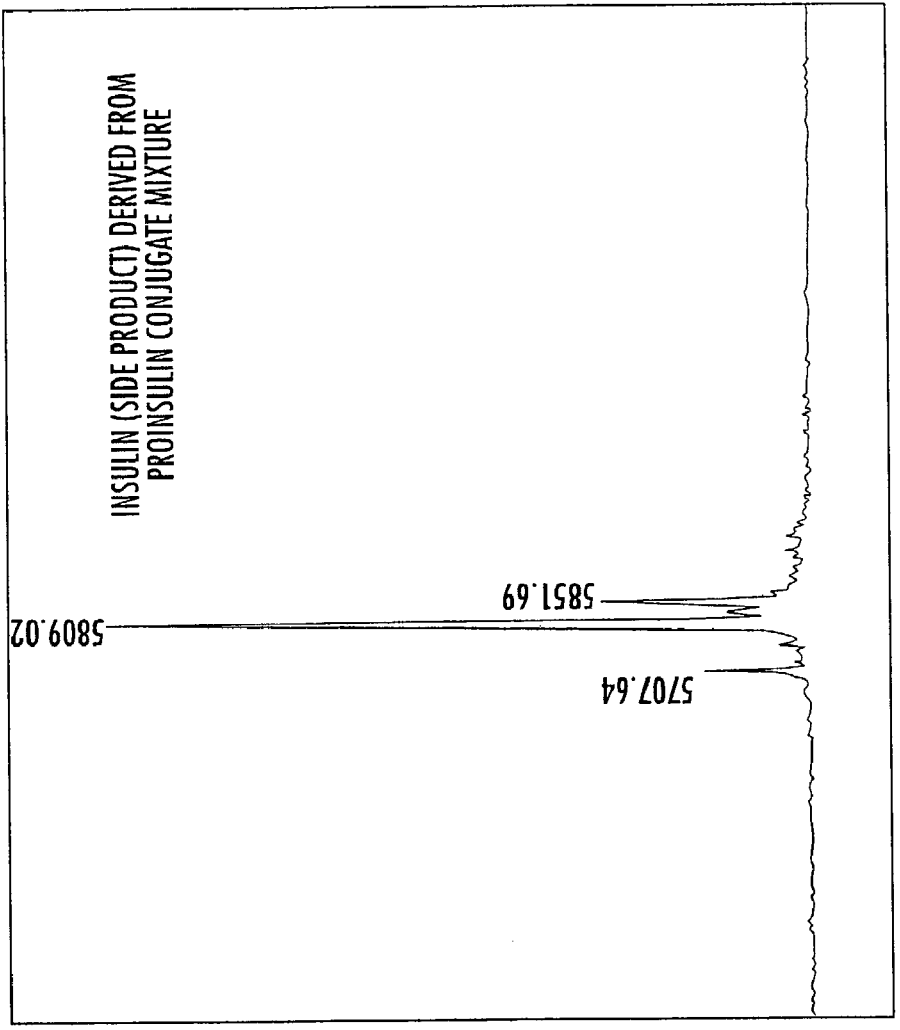
FIG. 13 illustrates an m.s. spectrum of insulin (side product) derived from proinsulin I conjugate mixture.

(b) Enzyme Cocktail Cleavage of Oligomer-Conjugated Recombinant Proinsulin I. An aliquot of the Tris-HCl solution of the product mixture from Example 1(a) was analyzed by HPLC to determine the polypeptide concentration. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture from Example 11(a) (0.424 µmol/mL) was then allowed to react with trypsin (5.97×10$^{-4}$ µmol/mL) and carboxypeptidase B (1.93×10$^{-4}$ µmol/mL). After 30 minutes, the reaction was quenched by the addition of 1.58 mL of 1% trifluoroacetic acid in acetonitrile. The major products were identified by HPLC retention time (relative to the retention times of known reference standards) and mass spectral analysis. Insulin (10%) and LYS$^{B29}$-Hexyl-PEG7-Oligomer-Conjugated Insulin (84%) were thus obtained (FIGS. 11–13).

Example 12

Isolation of the Products of Oligomer-Conjugation of Recombinant Proinsulin I Reversed-phase HPLC was used to isolate the major products from the product mixture obtained from the conjugation reaction described in Example 11(a). An HPLC column (1.0 cm. i.d.×25 cm. length) was packed with a commercially available C18 stationary phase known to be useful for the separation of peptides and proteins, and then was incorporated into an HPLC system. The system was equilibrated with elution buffer, a mixture comprising 72% mobile phase A (H$_2$O with 0.1% trifluoroacetic acid) and 28% mobile phase B (acetonitrile with 0.1% trifluoroacetic acid) that was delivered at a flow rate of 5 mL/min. A solution of the product mixture in 100 mM Tris-HCl Buffer, pH 7.6, was applied to the reversed-phase column, and the products were separated and eluted using a gradient in which the acetonitrile component of the elution buffer (mobile phase B) was increased as follows:

28%–30% mobile phase B over 60 minutes, then
  30%–32% mobile phase B over 30 minutes, then
  32%–36% mobile phase B over 40 minutes.

Figure 14:
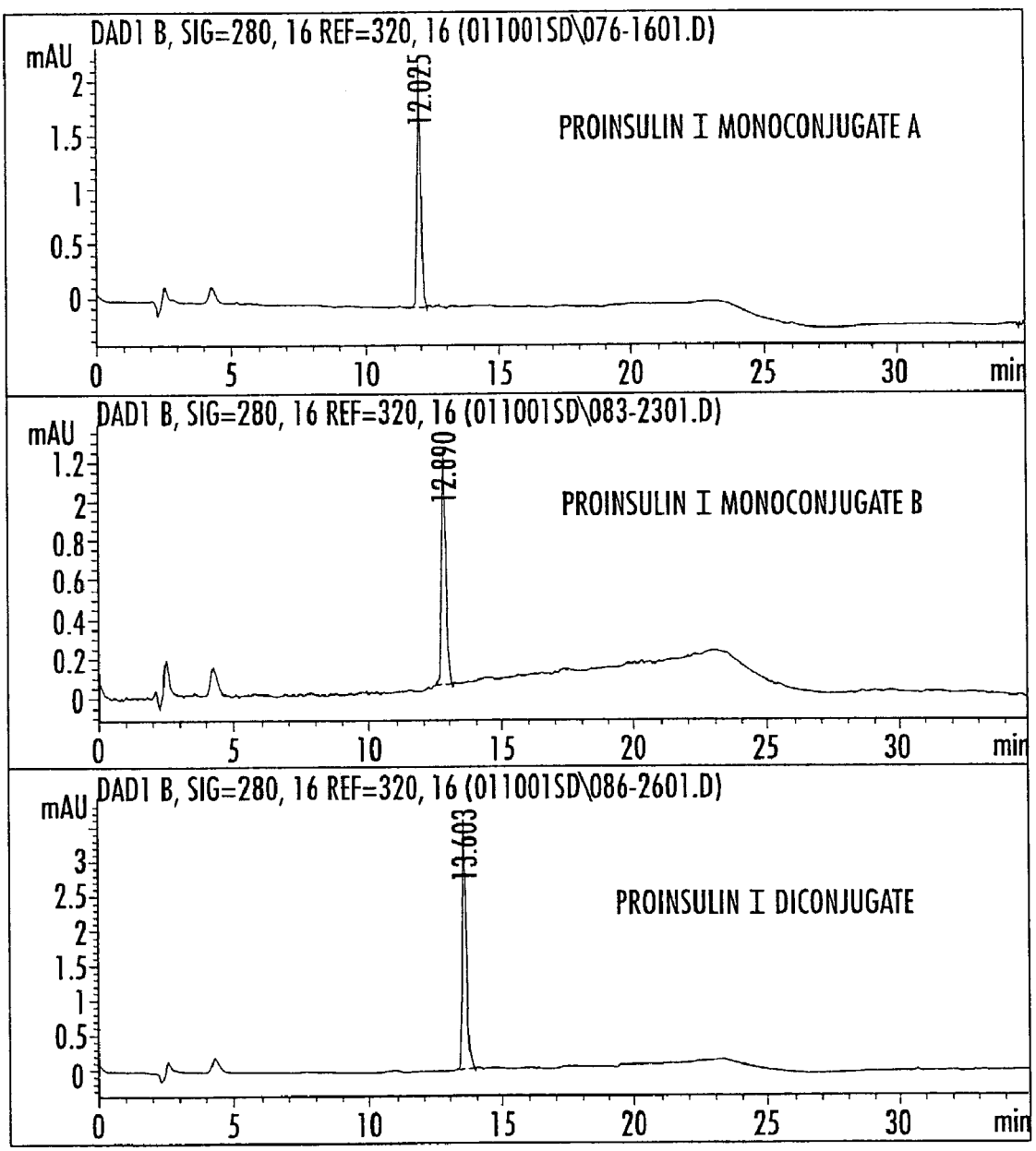
FIG. 14 illustrates an HPLC profile of proinsulin I monoconjugate A, proinsulin I monoconjugate B and proinsulin I diconjugate.
Figure 15:
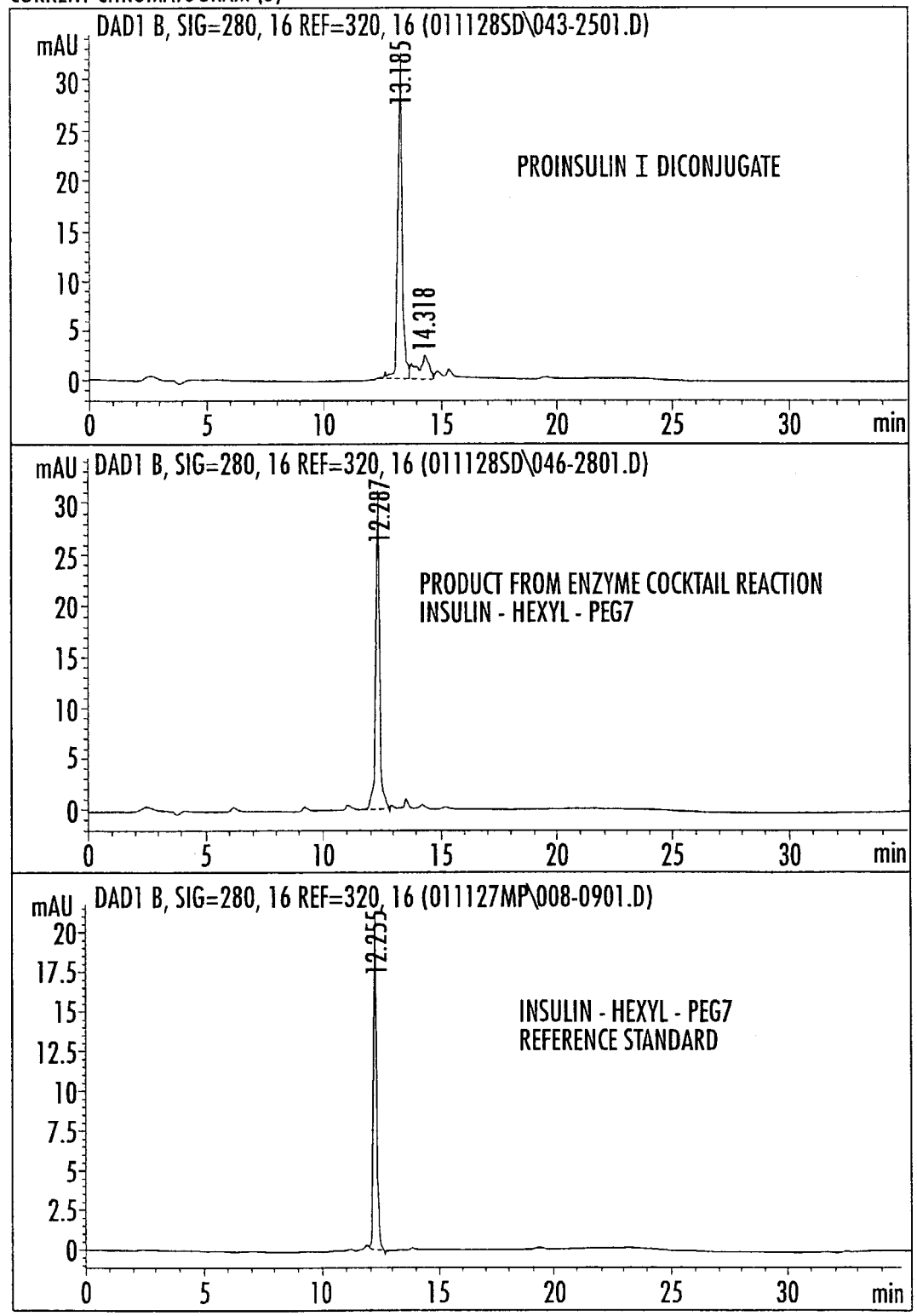
FIG. 15 illustrates an HPLC profile of production of Insulin-hexyl-PEG7 monoconjugate from reaction of proinsulin I diconjugate with enzyme cocktail of carboxy peptidase B and trypsin.
Figure 16:
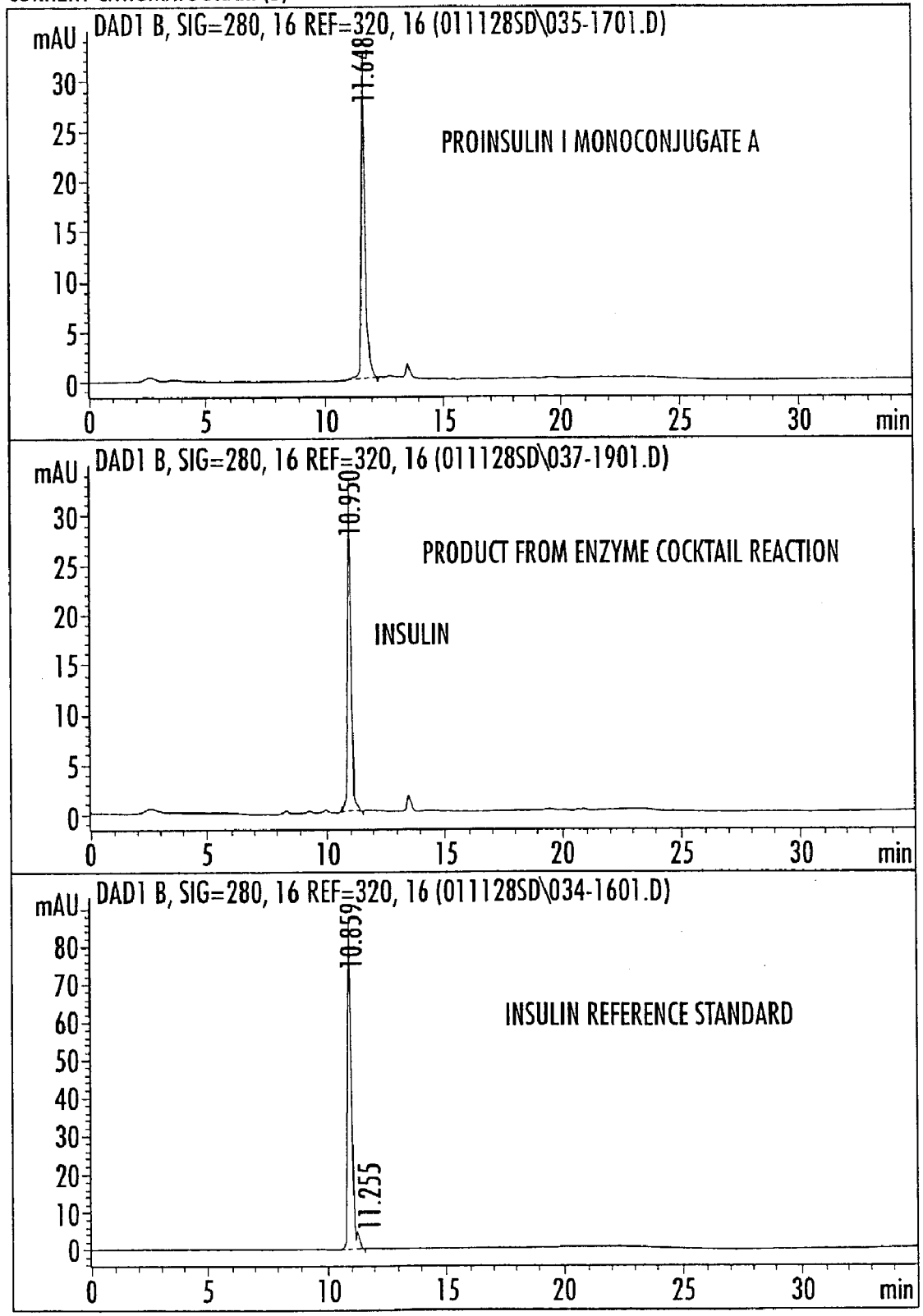
FIG. 16 illustrates an HPLC profile of production of insulin (side product) from reaction of proinsulin I monoconjugate A with enzyme cocktail of carboxy peptidase B and trypsin.

Fractions were collected and individually analyzed by HPLC to determine the identity and purity of the product contained therein. Common fractions containing one of the four products (monoconjugate-A ("Proinsulin I Monoconjugate-A"), monoconjugate-B ("Proinsulin I Monoconjugate-B"), diconjugate ("Proinsulin I Diconjugate") and triconjugate ("Proinsulin I Triconjugate") were then pooled, and the solvent was removed by rotary evaporation. HPLC (FIG. 14) and mass spectral analysis were used to determine the identity and purity of each isolate.

Example 13

Enzyme Cocktail Cleavage of Isolated Conjugates of Recombinant Proinsulin (I)

Each conjugate (Proinsulin I Mono A, Mono B, Di, or Tri) that was isolated using the procedure described in Example 12 was dissolved in 100 mM Tris-HCl Buffer, pH 7.6, and analytical HPLC was used to determine the polypeptide concentration of the resulting solution. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The crude mixture (1 mmol) was then allowed to react with trypsin (1.39×10$^{-3}$ mmol) and carboxypeptidase B (4.56×10$^{-4}$ mmol). After 30 minutes, the reaction was quenched by addition of 1% trifluoroacetic acid in acetonitrile. The product mixture from each reaction was processed and analyzed by HPLC. The HPLC retention time relative to that of reference standards and mass spectral analysis were used to determine the identity and purity of each product (Table 1).

TABLE 1

Oligomer-conjugates of Proinsulin I and Products (or Expected Products) from Enzyme Cocktail Cleavage of Each

| Conjugate | Product (Expected Products) | Figure |
|---|---|---|
| Proinsulin I Mono A (Proinsulin I conjugated at Lys 64) | Insulin, (Lys64-hexyl-PEG7-oligomer-conjugated C-peptide), (Diarginal insulin), (monoarginal insulin), (Arg65Lys$^{64}$-hexyl-PEG7-oligomer-conjugated C-peptide) and leader peptide | 16 |
| Proinsulin I Mono B (proinsulin I conjugated at B29) | (Lys $^{B29}$-Hexyl-PEG7-oligomer-conjugated insulin), (Des Arg 31, 32 Lys $^{B29}$-hexyl-PEG7-oligomer conjugated proinsulin or proinsulin I), Des 65, 64 Lys $^{B29}$-hexyl-PEG7-oligomer conjugated proinsulin or proinsulin I), leader peptide) | — |
| Proinsulin I Di (proinsulin I conjugated at B29 and Lys 64) | LysB29-Hexyl-PEG7-Oligomer-Conjugated Insulin (Lys$^{64}$-hexyl-PEG7-oligomer conjugated C-peptide), (Des 65 Lys $^{64}$Lys $^{B29}$-Di (hexyl-PEG7-oligomer conjugated proinsulin or proinsulin I), Des Arg 31, 32 Lys $^{64}$Lys $^{B29}$-Di(hexyl-PEG7-oligomer) conjugated proinsulin or proinsulin I), (leader peptide), , (Arg31, 32 Lys$^{64}$-hexyl-PEG7-oligomer conjugated C-peptide), (Arg32 Lys$^{64}$-hexyl-PEG7-oligomer conjugated C-peptide) | 15 |

TABLE 1-continued

Oligomer-conjugates of Proinsulin I and Products (or Expected Products) from Enzyme Cocktail Cleavage of Each

| Conjugate | Product (Expected Products) | Figure |
|---|---|---|
| Proinsulin I Tri (proinsulin I conjugated at B29, Lys 64 and N-amino terminal of Leader peptide) | (LysB29-Hexyl-PEG7-Oligomer-Conjugated Insulin) (Lys-hexyl-PEG7-oligomer-conjugated C-peptide) (Lys $^{B29}$-hexyl-PEG7-oligomer conjugated Insulin-Arg$^{31}$–Arg$^{32}$, Des 65 Lys $^{64}$Lys $^{B29}$-Di (hexyl-PEG7-oligomer conjugated proinsulin or proinsulin I, Des Arg 31, 32 Lys $^{64}$Lys$^{B29}$-Di (hexyl-PEG7-oligomer) conjugated proinsulin or proinsulin I, , Hexyl-PEG7-oligomer Leader peptide-Arg and Hexyl-PEG7-oligomer Leader peptide | — |

Example 14

Trypsin Cleavage of Isolated Conjugates of Proinsulin I

Each conjugate (Proinsulin I Mono A, Mono B, Di, or Tri) that was isolated using the procedure described in Example 12 is dissolved in 100 mM Tris-HCl Buffer, pH 7.6, and the resulting solution is analyzed by HPLC to determine the polypeptide concentration. A solution of trypsin (TPCK treated; from bovine pancreas) is prepared in 100 mM Tris-HCl Buffer, pH 7.6. Each conjugate (300 mmol) is then allowed to react with trypsin (1 mmol). After 20 minutes, the reaction is quenched by addition of 1% trifluoroacetic acid in acetonitrile. The products of the reaction are isolated and analyzed by HPLC retention time and mass spectral analysis to determine identity. The expected products are Insulin (Arg31) or LysB29-hexyl-PEG7-oligomer-conjugated Insulin(Arg31) illustrated in Table 2.

TABLE 2

| Conjugate | Expected Products |
|---|---|
| Proinsulin I Mono A (Proinsulin I conjugated at Lys 64) | Insulin-Arg$^{31}$, Insulin-Arg$^{31}$–Arg$^{32}$, Des 65, 64 proinsulin or proinsulin I, Des Arg 31, 32 proinsulin or proinsulin I, Lys64-hexyl-PEG7-oligomer conjugated C-peptide and Arg65-Lys64-C-peptide |
| Proinsulin I Mono B (proinsulin I conjugated at B29) | LysB29-hexyl-PEG7-oligomer-conjugated insulin(Arg31), Insulin-Arg$^{31}$–Arg$^{32}$, Des 65, 64 Lys $^{B29}$-hexyl-PEG7-oligomer conjugated proinsulin or proinsulin I, Des Arg 31, 32 Lys$^{B29}$-hexyl-PEG7-oligomer conjugated proinsulin or proinsulin I, and C-peptide |
| Proinsulin I Di (proinsulin I conjugated at B29 and Lys 64) | Lys$^{B29}$-hexyl-PEG7-oligomer-conjugated insulin(Arg31), Arg65-Lys64-hexyl-PEG7-oligomer conjugated C-peptide, Lys $^{B29}$-hexyl-PEG7-oligomer conjugated Insulin-Arg$^{31}$–Arg$^{32}$, Des 65 Lys $^{64}$Lys $^{B29}$-Di (hexyl-PEG7-oligomer conjugated proinsulin or proinsulin I, Des Arg 31, 32 Lys $^{64}$Lys $^{B29}$-Di(hexyl-PEG7-oligomer) conjugated proinsulin or proinsulin I and Lys$^{64}$-hexyl-PEG7-oligomer conjugated C-peptide |
| Proinsulin I Tri (proinsulin I conjugated at B29, Lys 64 and N-amino terminal of Leader peptide) | Lys$^{B29}$-hexyl-PEG7-oligomer-conjugated insulin(Arg31), Arg65-Lys64-hexyl-PEG7-oligomer conjugated C-peptide, Lys $^{B29}$-hexyl-PEG7-oligomer conjugated Insulin-Arg$^{31}$–Arg$^{32}$, Des 65 Lys $^{64}$Lys $^{B29}$-Di (hexyl-PEG7-oligomer conjugated proinsulin or proinsulin I, Des Arg 31, 32 Lys $^{64}$Lys $^{B29}$-Di(hexyl-PEG7-oligomer) conjugated proinsulin or proinsulin I, Lys$^{64}$-hexyl-PEG7-oligomer conjugated C-peptide and Hexyl-PEG7-oligomer Leader peptide-Arg |

Example 15

Carboxypeptidase B Cleavage of Trypsin Cleavage Product Mixture

An aliquot of the reaction mixture containing $Lys^{B29}$-hexyl-PEG7-oligomer-conjugated Insulin($Arg^{31}$) (300 mmol) (from Example 14) in 100 mM Tris-HCl buffer, pH 7.6, is removed. A solution of carboxypeptidase B (from porcine pancreas) is prepared in 100 mM Tris-HCl buffer, pH 7.6. Carboxypeptidase B (1 mmol) is added to the reaction mixture. The reaction is allowed to continue for 15 hours, and then is quenched with addition of 1% trifluoroacetic acid in acetonitrile. The expected products of each reaction are illustrated in Table 3.

TABLE 3

| Conjugate | Expected Products |
| --- | --- |
| Proinsulin I Mono A | Insulin and Lys-hexyl-PEG7-oligomer conjugated C-peptide |
| Proinsulin I Mono B | $Lys^{B29}$-hexyl-PEG7-oligomer-conjugated insulin and C-peptide |
| Proinsulin I Di | $Lys^{B29}$-hexyl-PEG7-oligomer-conjugated insulin and Lys-hexyl-PEG7-oligomer conjugated C-peptide |
| Proinsulin I Tri | $Lys^{B29}$-hexyl-PEG7-oligomer-conjugated insulin and Lys-hexyl-PEG7-oligomer-conjugated C-peptide and Lys-hexyl-PEG7-oligomer conjugated leader peptide |

Example 16

Figure 2:
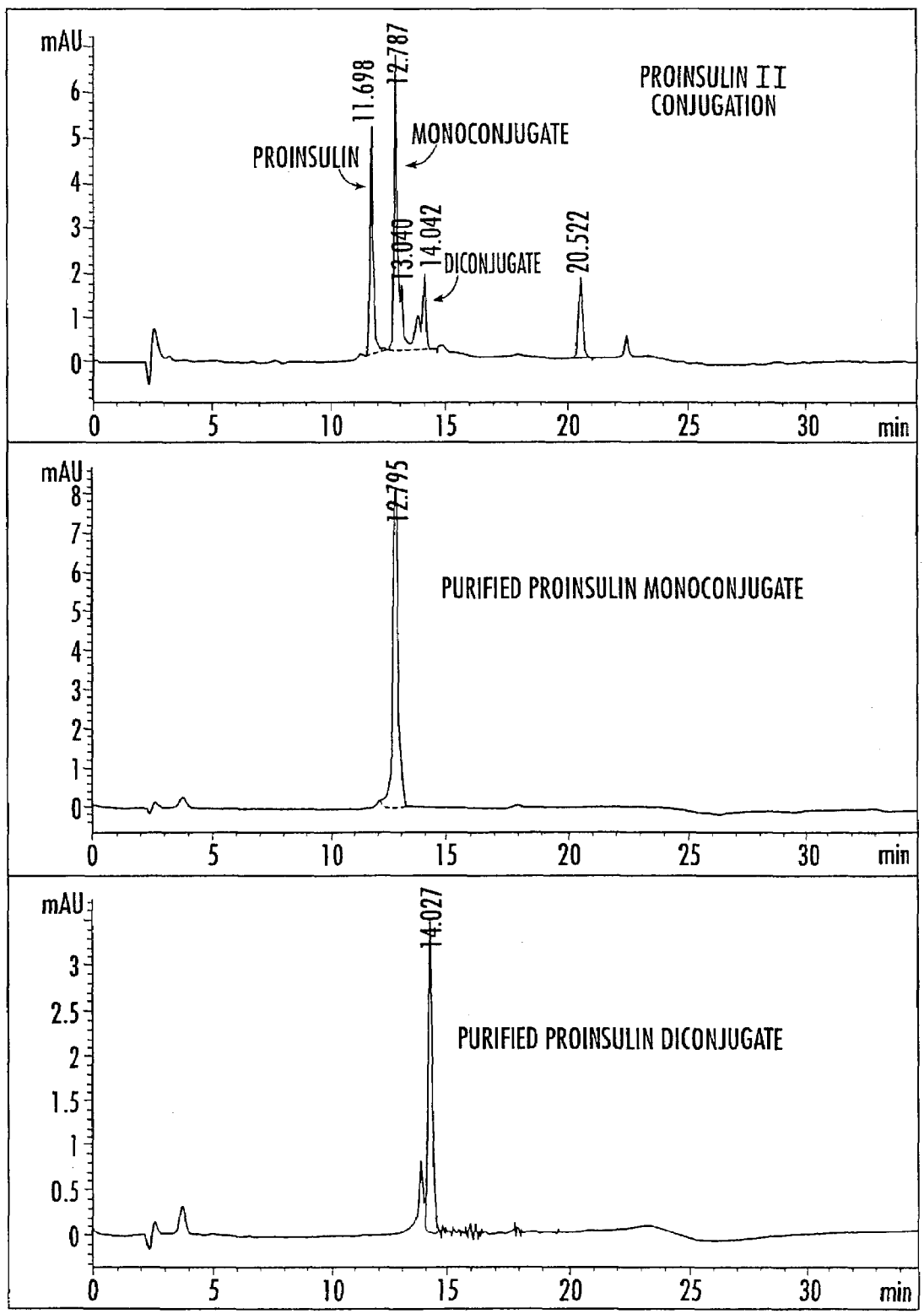
FIG. 2 illustrates an HPLC profile of proinsulin II conjugation.

Preparation of $Lys^{B29}$-Oligomer Conjugated Insulin (a) Conjugation of Recombinant Proinsulin II. Recombinant Proinsulin II (MW 11,133 Daltons) was obtained from Itoham Foods, Inc. of Ibaraki Pref, Japan. The Recombinant Proinsulin II had a leader peptide and a C-peptide that were each devoid of Lysine residues. A $2.55 \times 10^{-3}$ mmol portion of recombinant Proinsulin II was dissolved in mL of DMSO. To the solution was added 355 µL of triethylamine. The resulting solution was allowed to stir for 5 minutes, and then a solution of activated methylpolyethylene glycol ((PEGn)-hexyl oligomer) (n=7±3 or n=7) ($5.10 \times 10^{-3}$ mmol) in acetonitrile was added. The course of the reaction was monitored by HPLC. After the reaction appeared to be complete, it was quenched by addition of 3.7 mL of 5% aqueous trifluoroacetic acid solution. The reaction mixture was then processed and exchanged into 100 mM Tris-HCl Buffer, pH 7.6. The HPLC profile of the oligomer-conjugated recombinant Proinsulin II product mixture is shown in FIG. 2.

Figure 9:
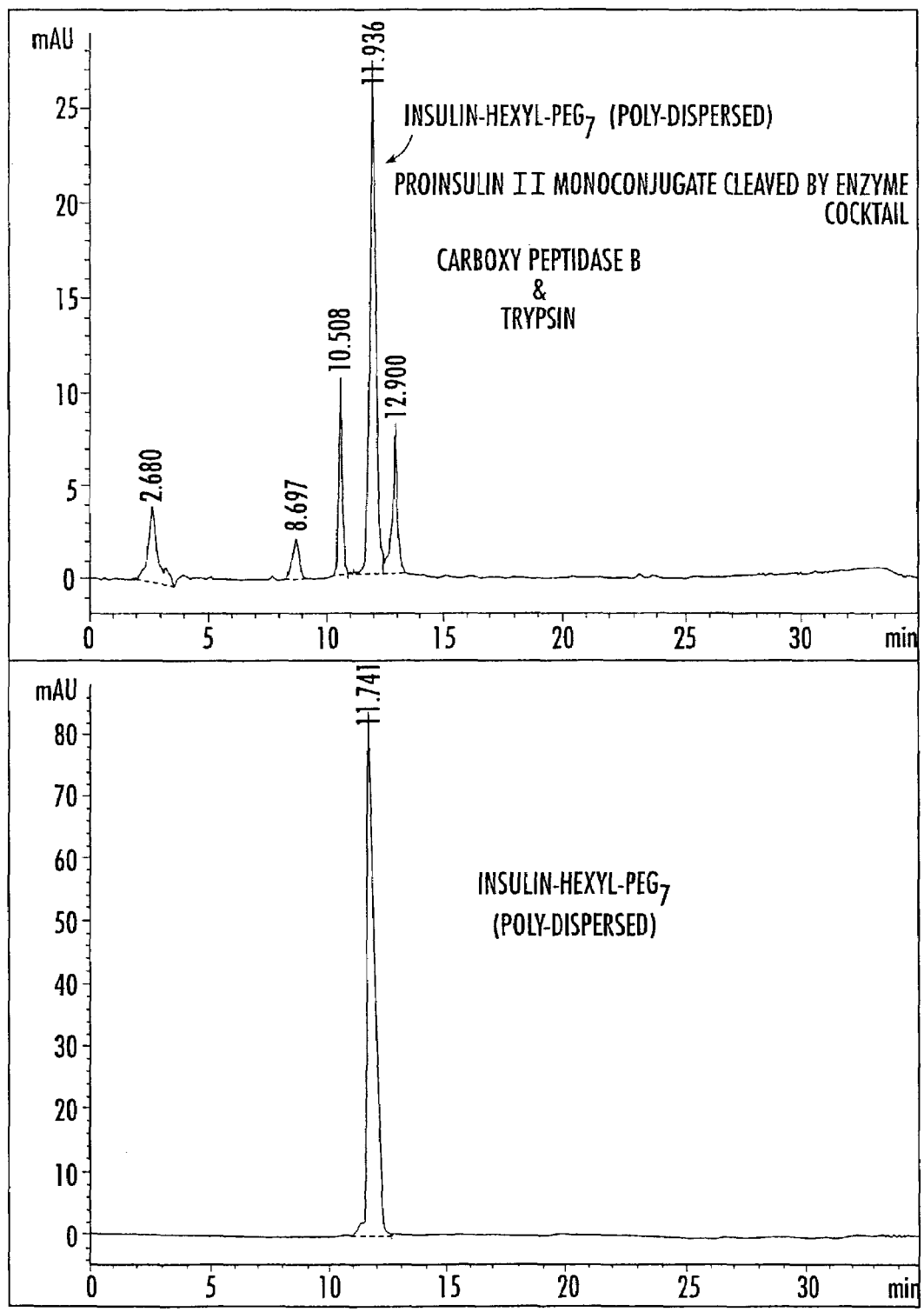
FIG. 9 illustrates an HPLC profile of the production of Insulin-hexyl-PEG7 (polydispersed) from Proinsulin II monoconjugate cleaved by an enzyme cocktail of carboxy peptidase B and trypsin.
Figure 10:
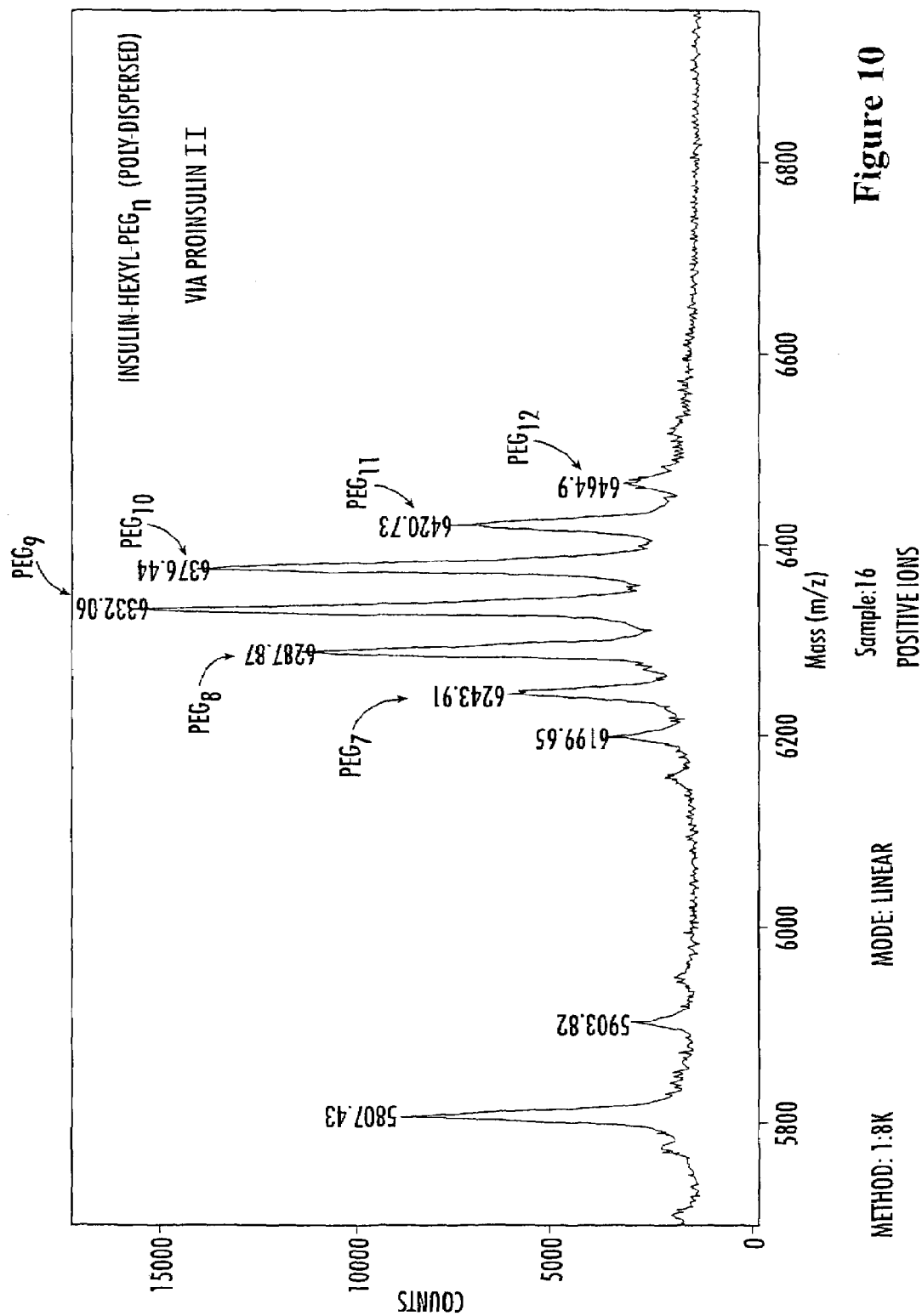
FIG. 10 illustrates an m.s. spectrum of Insulin-hexyl-PEGn (polydispersed) via proinsulin II.

(b) Enzyme Cocktail Cleavage of Oligomer-Conjugated Recombinant Proinsulin II. The Tris-HCl solution of the product mixture from Example 16(a) was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.399 µmol/mL) was allowed to react with trypsin ($5.57 \times 10^{-4}$ µmol/mL) and carboxypeptidase B ($1.82 \times 10^{-4}$ µmol/mL). After 30 minutes, the reaction was quenched by addition of 550 µL of 1% trifluoroacetic acid in acetonitrile. The major products were identified by HPLC retention time (relative to that of known reference standards) and mass spectral analysis. Insulin (23%) and $Lys^{B29}$-hexyl-PEGn-oligomer-conjugated Insulin (60%) and other (17%) were thus obtained (FIGS. 9–10).

Example 17

Figure 3:
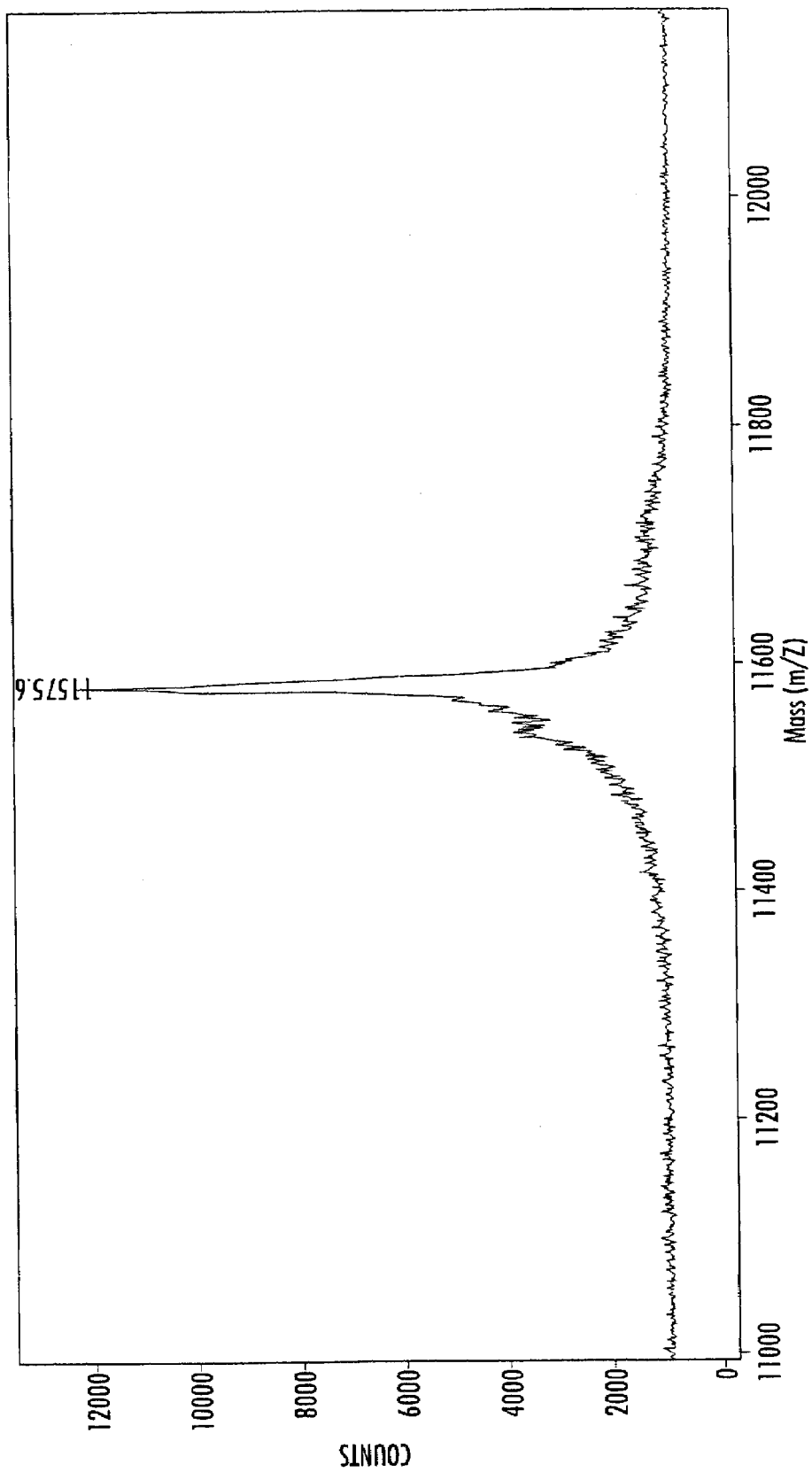
FIG. 3 illustrates an m.s. spectrum of purified proinsulin II monoconjugate.
Figure 4:
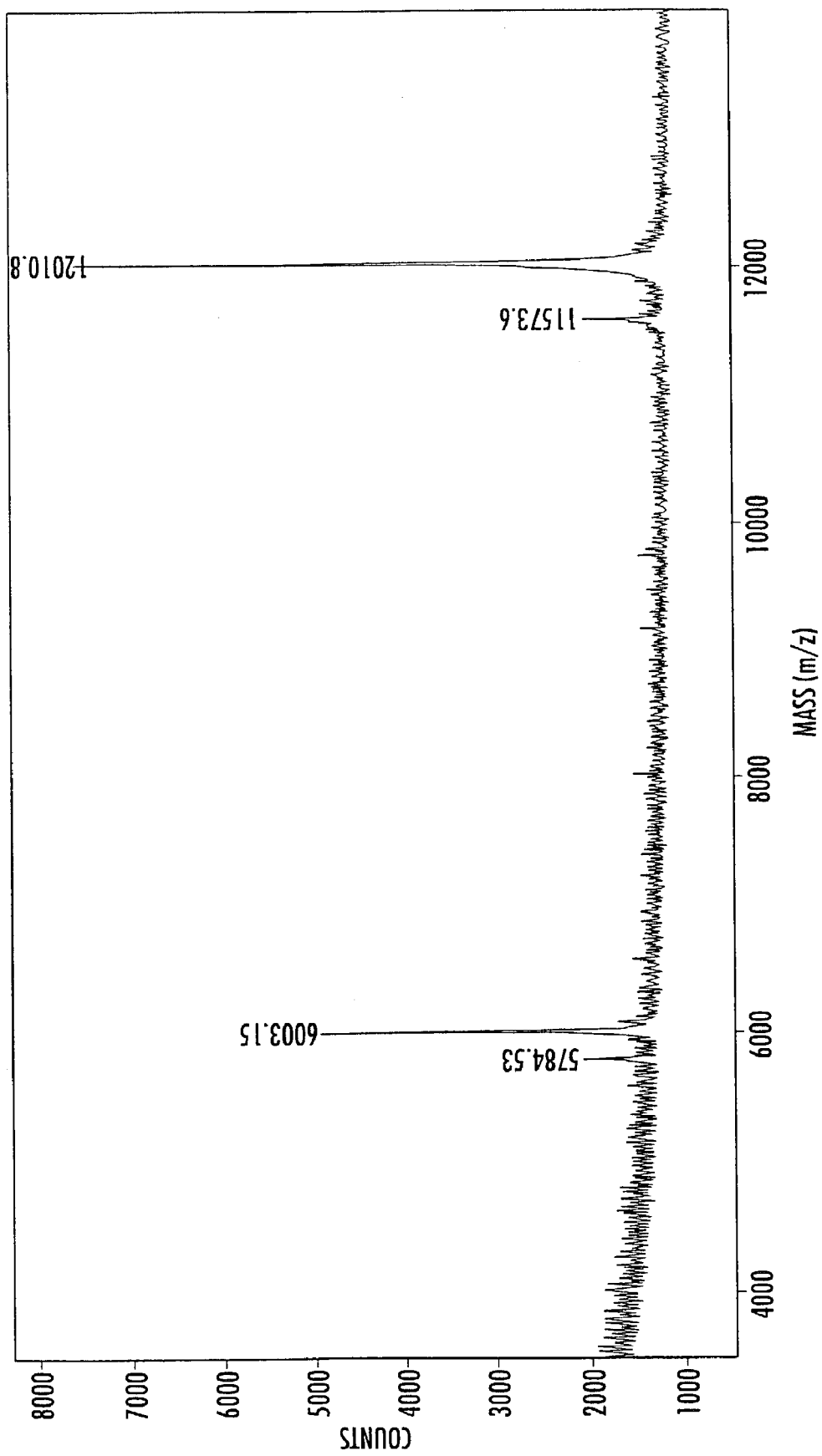
FIG. 4 illustrates an m.s. spectrum of purified proinsulin II diconjugate.

Isolation of the Products of Oligomer-Conjugation of Recombinant Proinsulin II Each major product from the conjugation reaction described in Example 16(a) was isolated using reversed-phase HPLC. A column (1.0 cm. i.d.×25 cm. length) was packed with a commercially available C18 stationary phase known to be useful for the resolution of polypeptides and proteins, and then was incorporated into an HPLC system. The system was equilibrated with elution buffer that was a mixture of 75% mobile phase A ($H_2O$ with 0.1% trifluoroacetic acid) and 25% mobile phase B (acetonitrile with 0.1% trifluoroacetic acid) that was delivered at a flow rate of 5 mL/min. The Tris-HCl solution of the product mixture from Example 16(a) was applied to the column, and the major products were separated and eluted using a gradient elution in which the composition of the elution buffer was changed from 25% mobile phase B to 35% mobile phase B over 120 minutes. Each of the fractions that were collected was analyzed by HPLC to determine the identity and purity of the product contained therein. Common fractions of each product (Proinsulin II monoconjugate ("Proinsulin II Mono") and diconjugate ("Proinsulin II Di") were then pooled, and the solvent was removed by rotary evaporation. The identity and purity of each product were determined by HPLC and mass spectrometric analyses (FIGS. 2–4).

Example 18

Enzyme Cocktail Cleavage of Isolated Conjugates of Recombinant Proinsulin II Each Proinsulin II conjugate (Proinsulin II Mono, Di or Tri) that was isolated using the procedure described in Example 17 was dissolved in 100 mM Tris-HCl Buffer, pH 7.6, and an aliquot of the solution was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The conjugate (0.127 µmol/mL) was allowed to react with trypsin ($1.77 \times 10^{-4}$ umol/mL) and carboxypeptidase B ($5.77 \times 10^{-5}$ µmol/mL). After 30 minutes, the reaction was quenched by addition of 250 µL of 1% trifluoroacetic acid in acetonitrile. Isolation of the major products followed by identification by HPLC retention time against reference standards and mass spectral analysis showed that Insulin or B-29 acylated Insulin-hexyl-PEG7 were produced in the reaction. The products and yields of each reaction are illustrated in Table 4.

TABLE 4

| Conjugate | Expected Products | Yield |
| --- | --- | --- |
| Proinsulin II Mono | Insulin | 15% |
|  | $Lys^{B29}$-hexyl-PEGn-oligomer conjugated insulin | 85% |
| Proinsulin II Di | $Lys^{B29}$-hexyl-PEGn-oligomer-conjugated insulin | 92% |

Example 19

Trypsin Cleavage of Isolated Conjugates of Proinsulin II

Each conjugate (Proinsulin II Mono, Di or Tri) from Example 17 was dissolved in 100 mM Tris-HCl Buffer, pH 7.6, and the resulting solution was analyzed by HPLC to determine the polypeptide concentration therein. A solution of trypsin (TPCK treated; from bovine pancreas) was prepared in 100 mM Tris-HCl Buffer, pH 7.6. Each conjugate (0.127 µmol/mL) was then allowed to react with trypsin ($4.23 \times 10^{-4}$ µmol/mL). After 20 minutes, reaction was quenched by addition of 250 µL of 1% trifluoroacetic acid in acetonitrile. Isolation of the major products followed by identification by HPLC retention time and mass spectral analysis showed that Insulin($Arg^{31}$) or $LYS^{B29}$-hexyl-PEGn-oligomer-conjugated Insulin($Arg^{31}$) was produced in the reaction. The products and yields of each reaction are illustrated in Table 5.

TABLE 5

| Conjugate | Products and (expected products) | Yield |
|---|---|---|
| Proinsulin II Mono | Insulin-Arg31, (C-peptide-Arg), (Leader peptide-Arg) | — |
|  | LysB29-hexyl-PEGn-oligomer conjugated insulin-Arg31 | — |
| Proinsulin II Di | LysB29-hexyl-PEGn-oligomer-conjugated insulin-Arg31, (C-peptide-Arg), (hexyl-PEGn-oligomer conjugated Leader peptide-Arg) | — |

Example 20

Carboxypeptidase B Cleavage of Trypsin Cleavage Mixture

Figure 5:
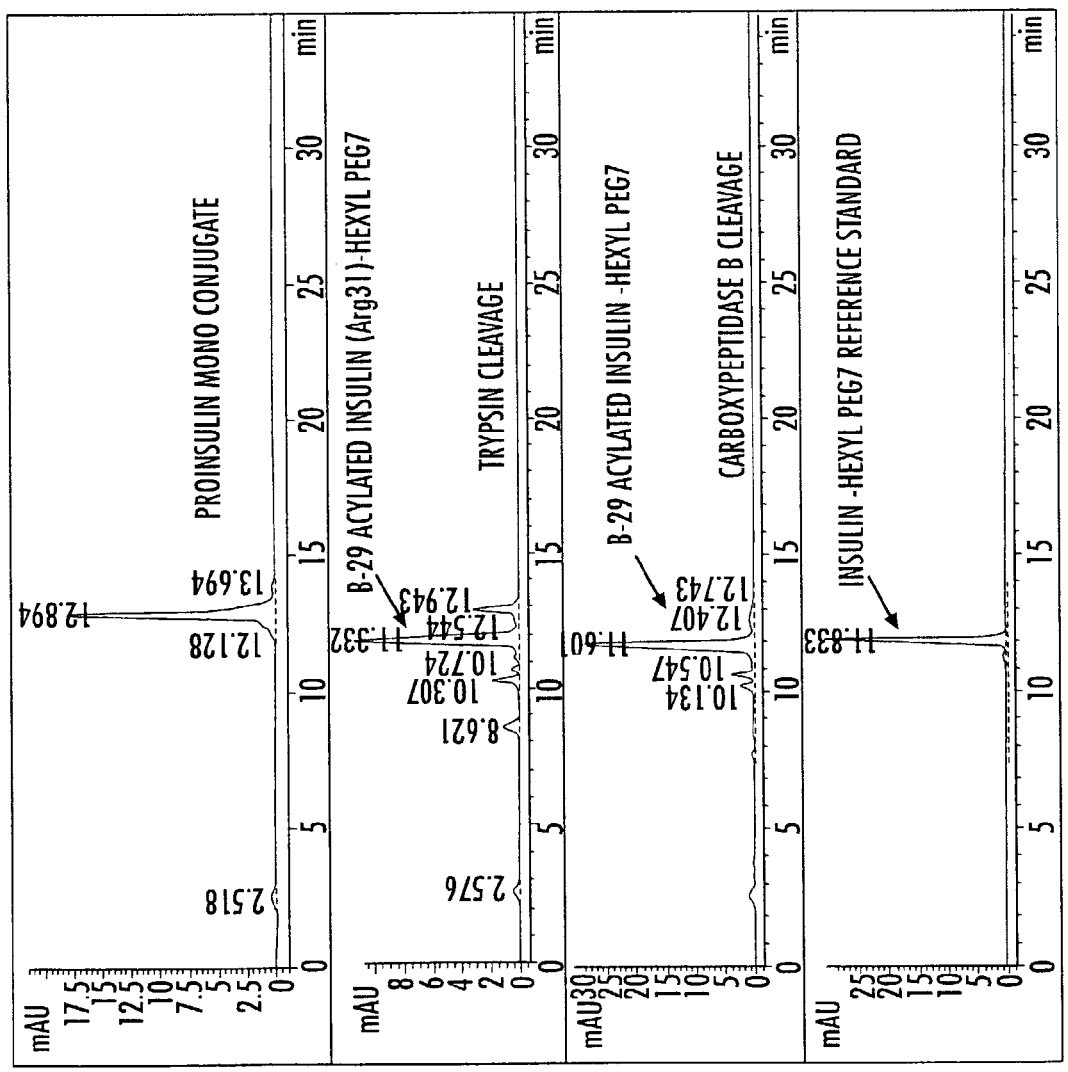
FIG. 5 illustrates an HPLC profile of production of Insulin-hexyl-PEG7 monoconjugate.
Figure 6:
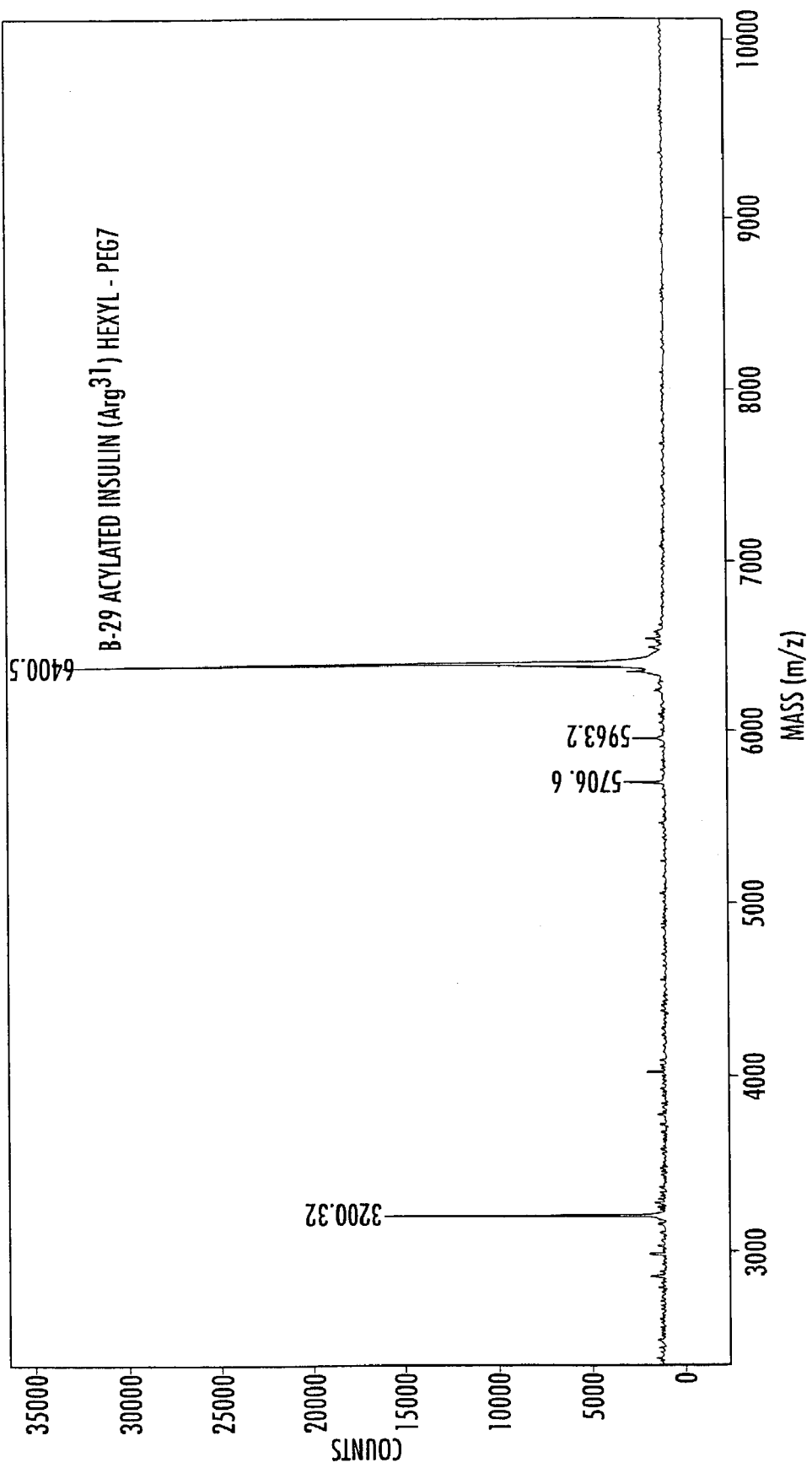
FIG. 6 illustrates an m.s. spectrum of the product of trypsin cleavage of a proinsulin II monoconjugate.
Figure 7:
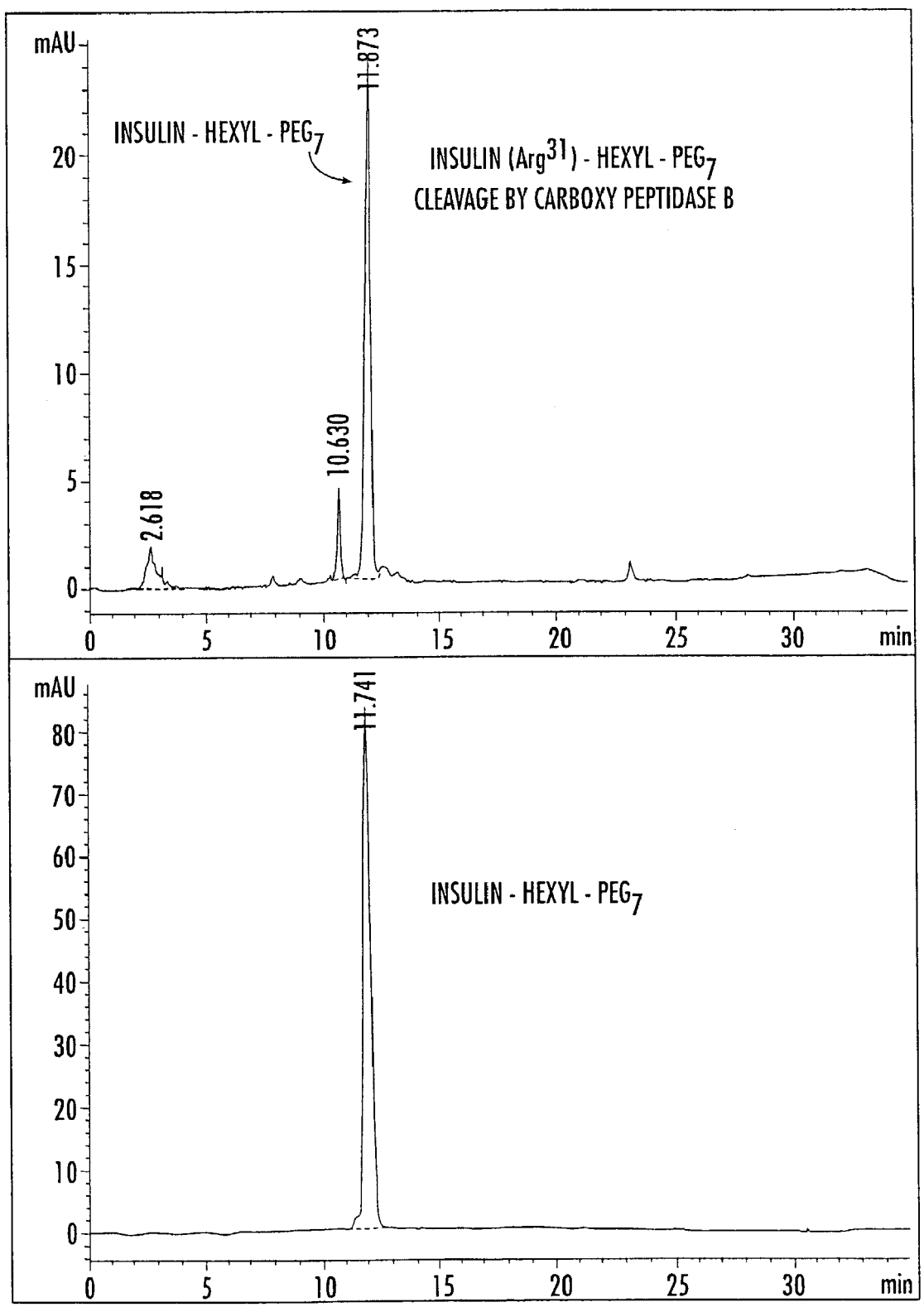
FIG. 7 illustrates an HPLC profile of Insulin(Arg$^{31}$)-hexyl-PEG7 cleavage by carboxy peptidase B.
Figure 8:
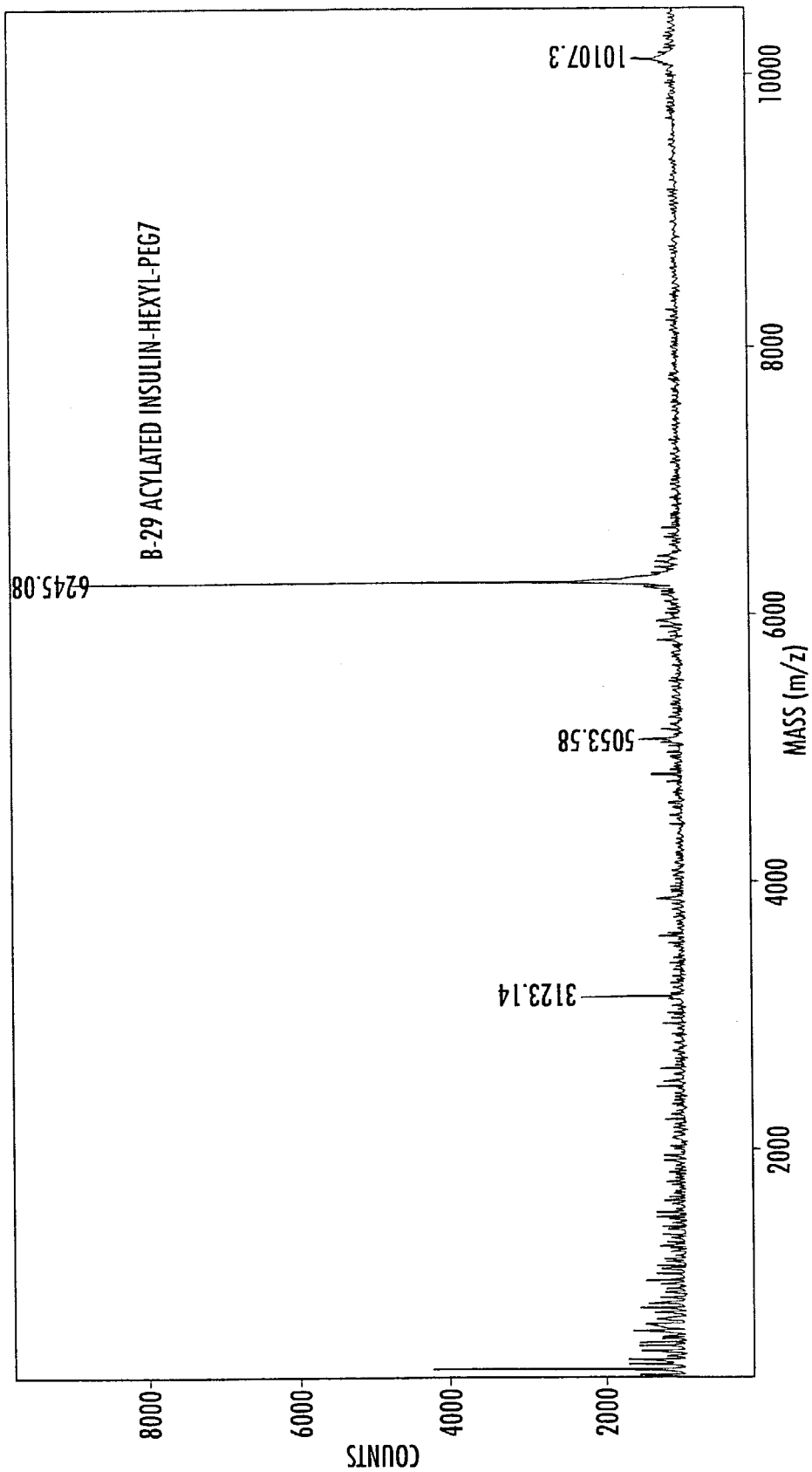
FIG. 8 illustrates an m.s. spectrum of the product of carboxypeptidase cleavage of B-29 acylated Insulin(Arg$^{31}$)-hexyl-PEG7 conjugate.

An aliquot of the reaction mixture of $Lys^{B29}$-hexyl-PEG7-oligomer-conjugated Insulin($Arg^{31}$) ($3.10 \times 10^{-5}$ mmol) from Example 19 was removed. A solution of carboxypeptidase B (from porcine pancreas) was prepared in 100 mM Tris-HCl buffer pH 7.6 Carboxypeptidase B ($103 \times 10^{-7}$) was added to the reaction mixture. Reaction was allowed to continue for 15 hours, and then was quenched with addition of 1% trifluoroacetic acid in acetonitrile. After processing, the products of the reaction were analyzed by HPLC. Retention time and mass spectral analysis were used to determine identity. Insulin (23%) and $Lys^{B29}$-hexyl-PEGn-oligomer-conjugated insulin (60%) (FIGS. 5, 7–8) were produced from the reaction of Proinsulin II monoconjugate. The expected products of the Proinsulin II diconjugate reaction are illustrated in Table 6.

TABLE 6

| Conjugate | Products (Expected Products) | Yield |
|---|---|---|
| Proinsulin II Mono | Insulin and $Lys^{B29}$-hexyl-PEGn-oligomer-conjugated Insulin | 23% 60% |
| Proinsulin II Di | ($Lys^{B29}$-Hexyl-PEGn-oligomer-conjugated Insulin) |  |

Example 21

Preparation of $Lys^{B29}$-Oligomer-Conjugated Insulin (a) Conjugation of Natural Human Proinsulin. Natural human proinsulin (Sigma Chemical Co.) ($3.20 \times 10^{-4}$ mmol) is dissolved in 5 mL of DMSO. To the solution is added 45 µL of triethylamine. The solution is allowed to stir for 5 minutes before a solution of activated PEG7-hexyl oligomer ($6.4 \times 10^{-4}$ mmol) in acetonitrile is added. After the reaction has progressed such that HPLC analysis indicates that the proinsulin has been consumed (or the concentration of proinsulin is no longer decreasing), the reaction is quenched by addition of 0.5 mL of 5% aqueous trifluoroacetic acid solution. The reaction mixture is then processed and exchanged into 100 mM Tris-HCl Buffer, pH 7.6.

(b) Enzyme Cocktail Cleavage of Oligomer-Conjugated Natural Proinsulin. An aliquot of the Tris-HCl solution of the product mixture from Example 21(a) is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The crude mixture (1 mol eq.) is then allowed to react with trypsin ($1.39 \times 10^{-3}$ mol eq.) and carboxypeptidase B ($4.56 \times 10^{-4}$ mol eq.). After 30 minutes, the reaction is quenched by addition of 1% trifluoroacetic acid in acetonitrile. The product mixture of the reaction is processed and analyzed by HPLC. Retention time (versus that of reference standards) and mass spectral analysis are used to determine identity. The expected products of the reaction are Insulin and $Lys^{B29}$-hexyl-PEG7-oligomer-conjugated Insulin.

Example 22

Isolation of the Products of Conjugation of Natural Human Proinsulin

Each major product obtained from the conjugation reaction described in Example 21(a) is isolated using reversed-phase HPLC. A column (1.0 cm. i.d.×25 cm. length) is packed with a commercially available C18 stationary phase known to be useful for the resolution of polypeptides and proteins, and then is incorporated into an HPLC system. The system is equilibrated with elution buffer that comprises a mixture of 75% mobile phase A (H2O with 0.1% trifluoroacetic acid) and 25% mobile phase B (acetonitrile with 0.1% trifluoroacetic acid). The Tris-HCl solution of the product mixture from Example 21(a) is applied to the column, and the major products are separated and eluted using a gradient elution in which the percentage of the acetonitrile component is increased from 25%–35% over 120 minutes. Fractions are collected and analyzed by HPLC to determine the identity and purity of the product therein. Common fractions of each product are pooled, and the solvent is removed by rotary evaporation. The identity and purity of each product peak are determined by HPLC and mass spectrometry. The expected products consist of 2 human Proinsulin monoconjugates (Lys B29 or Lys 64), 1 human Proinsulin diconjugate (Lys B29, Lys 64 and 1 human Proinsulin triconjugate (Phe B1, Lys B29, Lys 64). Use of modified conjugation conditions of Example 21 results in three human Proinsulin monoconjugates (Phe B1 or Lys B29 or Lys 64).

Example 23

Enzyme Cocktail Cleavage of Isolated Conjugates of Natural Human Proinsulin

Each conjugate that is obtained using the procedure described in Example 22 is dissolved in 100 mM Tris-HCl Buffer, pH 7.6, and the resulting solution is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The crude mixture (1 mol eq.) is then allowed to react with trypsin ($1.39 \times 10^{-3}$ mol eq.) and carboxypeptidase B ($4.56 \times 10^4$ mol eq.). After 30 minutes, the reaction is quenched by addition of 1% trifluoroacetic acid in acetonitrile. The products are processed and analyzed by HPLC. Retention time (compared to that of reference standards) and mass spectral analysis are used to determine identity. The expected products of the reaction are Insulin or LysB29-hexyl-PEG7-oligomer-conjugated Insulin or LysB29 or PheB1-Di[Hexyl-PEG7-Oligomer]-Conjugated Insulin or Lys64-hexyl-PEG7-oligomer-conjugated C-peptide or PheB1-hexyl-PEG7-oligomer-conjugated Insulin or LysB29 or C-peptide.

Example 24

Trypsin Cleavage of Isolated Conjugates of Natural Human Proinsulin

Each conjugate that is obtained as described in Example 22 is dissolved in 100 mM Tris-HCl Buffer, pH 7.6, and the resulting solution is analyzed by HPLC to determine the polypeptide concentration therein. A solution of trypsin (TPCK treated; from bovine pancreas) is prepared in 100 mM Tris-HCl Buffer, pH 7.6. The conjugate (300 mol eq.) is then allowed to react with trypsin (1 mol eq.). After 20 minutes, the reaction is quenched by addition of 1% trifluoroacetic acid in acetonitrile. The products are processed and analyzed by HPLC. Retention time and mass spectrometry are used to determine identity. The expected products of the reaction are Insulin(Arg31) or desThr-Insulin or LysB29-hexyl-PEG7-oligomer-conjugated Insulin(Arg31) or LysB29, PheB1-Di [Hexyl-PEG7-Oligomer]-Conjugated Insulin-Arg31 or PheB1-hexyl-PEG7-oligomer-conjugated Insulin-Arg31 or Lys64-hexyl-PEG7-oligomer-conjugated C-peptide or C-peptide-Arg.

Example 25

Carboxypeptidase B Cleavage of Trypsin Cleavage Mixture

An aliquot of the trypsin reaction mixture of each conjugate (300 mmol) from Example 24 is removed. A solution of carboxypeptidase B (from porcine pancreas) is prepared in 100 mM Tris-HCl buffer, pH 7.6. Carboxypeptidase B (1 mmol) is added to the reaction mixture. Reaction is allowed to continue for 15 hours, and then is quenched with addition of 1% trifluoroacetic acid in acetonitrile. The products are processed and analyzed by HPLC. Retention time and mass spectral analysis are used to determine identity. The expected products are Insulin or des Thr-Insulin or LysB29-hexyl-PEG7-oligomer-conjugated Insulin or PheB1- hexyl-PEG7-oligomer-conjugated Insulin or LysB29, PheB1-Di [Hexyl-PEG7-Oligomer]-Conjugated Insulin or Lys64-hexyl-PEG7-oligomer-conjugated C-peptide or C-peptide.

Example 26

Optimized Preparation of $Lys^{B29}$-Oligomer-Conjugated Insulin

Analysis of the experimental data from Example 11 indicated that $Lys^{B29}$-hexyl-PEG7-oligomer-conjugated Insulin and Lys-hexyl-PEG7-oligomer-conjugated C-peptide could be obtained in high yield and purity by (a) acylating the ε-amino group of all lysine residues that are present on a proinsulin raw material, and (b) cleaving the resulting, fully oligomer-conjugated proinsulin with an enzyme cocktail made up of trypsin and carboxypeptidase B. Experimental confirmation of this hypothesis was obtained as follows.

(a) Conjugation of Recombinant Proinsulin I. Recombinant Proinsulin I (MW 10,642 Daltons) is obtained from Biobras, Belo Horizonte, Brazil. A $2.32 \times 10^{-3}$ mmol portion of proinsulin I is dissolved in 10 mL of DMSO. To the solution is added 324 μL of triethylamine. The resulting solution is allowed to stir for 5 minutes, and then a solution of activated methylheptaethylene glycol(PEG7)-hexyl oligomer (4–6 mol eq.; sufficient to covert all Proinsulin I to the triconjugate) in acetonitrile is added. The course of the conjugation (acylation) reaction is monitored by HPLC. When reaction appears to be complete (i.e., no unconjugated Proinsulin I is observed by HPLC), it is quenched by addition of 3.54 mL of 5% aqueous trifluoroacetic acid solution. The reaction mixture is then processed and exchanged into 100 mM Tris-HCl Buffer, pH 7.6. The HPLC profile of the product mixture, oligomer-conjugated recombinant Proinsulin I, is expected to show peaks corresponding to triconjugate (all Lys and N-terminus conjugated) and diconjugate only.

(b) Enzyme Cocktail Cleavage of Oligomer-Conjugated Recombinant Proinsulin I. An aliquot of the Tris-HCl solution of the product mixture from Example 16(a) is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture from Example 16(a) (0.424 μmol/mL) is then allowed to react with trypsin ($5.97 \times 10^{-4}$ μmol/mL) and carboxypeptidase B ($1.93 \times 10^{-4}$ μmol/mL). After 30 minutes, the reaction is quenched by the addition of 1.58 mL of 1% trifluoroacetic acid in acetonitrile. The major products are identified by HPLC retention time (relative to the retention times of known reference standards) and mass spectral analysis. $Lys^{B29}$-Hexyl-PEG7-Oligomer-Conjugated Insulin, the only insulin conjugate that is present, is expected to be obtained in near 95% yield. $Lys^1$-Hexyl-PEG7-Oligomer-Conjugated C-peptide is also obtained in near quantitative yield.

Example 27

Preparation of $Lys^{B29}$-Oligomer-Conjugated Insulin-20 g Scale-Up (a) Conjugation of Recombinant Proinsulin I. Recombinant Proinsulin I (MW 10,642 Daltons) was obtained from Biobras, of Belo Horizonte, Brazil. A 20g (1.85 mmol) portion of proinsulin I was dissolved in 540 mL of 50 mM boric acid. The solution was brought to pH 9.3 with 4N sodium hydroxide solution and added to 120 mL ethanol and adjusted to pH 10.2 with sodium hydroxide. To the above stirred solution was added a solution of activated methylheptaethylene glycol ((PEG7)-hexyl oligomer) (4×1.85 mmol) in 14 mL ethanol. The course of the conjugation (acylation) reaction was monitored by HPLC and the pH was maintained at pH 10.2 using 4N sodium hydroxide. When reaction appeared to be complete after 20 minutes, it was quenched by addition of 4N hydrochloric acid to pH 6.8. The reaction mixture was then processed and exchanged into 100 mM Tris-HCl Buffer, pH 7.6 via diafiltration using Millipore's Pellicon II system. The HPLC profile of the product mixture showed >80% di and tri oligomer-conjugates of recombinant Proinsulin I.

(b) Enzyme Cocktail Cleavage of Oligomer-Conjugated Recombinant Proinsulin I. An aliquot of the Tris-HCl solution of the product mixture was analyzed by HPLC to determine the polypeptide concentration and diluted to 15 mg/ml insulin equivalent. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (2.64 mmol) was then allowed to react with trypsin ($3.68 \times 10^{-3}$ mmol) and carboxypeptidase B ($1.20 \times 10^{-3}$ mmol) at 15° C. After 55 minutes, the reaction was quenched by the addition of 4N of hydrochloric acid to pH~3. The major products were identified by HPLC retention time (relative to the retention times of known reference standards) and mass spectral analysis. $Lys^{B29}$-Hexyl-PEG7-Oligomer-Conjugated Insulin (80%) and insulin (7%) were thus obtained. Lys64-Hexyl-PEG7-Oligomer conjugated c-peptide was obtained as the major side product from C-peptide portion of the conjugates of proinsulin I.

(c) Isolation of the Products of Enzyme Cocktail Cleavage of Oligomer-Conjugation of Recombinant Proinsulin I Reversed-phase HPLC was used to isolate the major products from the product mixture obtained from the conjugation reaction. An HPLC column (10 cm. i.d.×25 cm. length) was packed with a commercially available C18 stationary phase known to be useful for the separation of peptides and proteins, and then was incorporated into an HPLC system. The system was equilibrated with elution buffer, a mixture comprising 80% mobile phase A (10 mM ammonium acetate buffer) and 20% mobile phase B (acetonitrile) that was delivered at a flow rate of 120 mL/min. A solution of the product mixture in 100 mM Tris-HCl Buffer, pH 7.6, was applied to the reversed-phase column, and the products were separated and eluted using a gradient in which the acetonitrile component of the elution buffer (mobile phase B) was increased as follows:

20%–27% mobile phase B over 30 minutes, then
27%–29% mobile phase B over 30 minutes, then
29%–32% mobile phase B over 12 minutes, then
32%–35% mobile phase B over 6 minutes, then
35%–45% mobile phase B over 13 minutes.

Fractions were collected and individually analyzed by HPLC to determine the identity and purity of the product contained therein. Common fractions containing one of the three products (LysB29-Hexyl-PEG7-Oligomer-Conjugated Insulin ("PEG7 HIM2")), Insulin ("Insulin") and Lys64-Hexyl-PEG7-Oligomer conjugated c-peptide ("PEG7 Lys-C-peptide") were then pooled, and each pool was diluted to 10% acetonitrile with water and then processed, exchanged into 10 mM ammonium Acetate Buffer, pH 7.4 and concentrated via diafiltration using Millipore's Pellicon II system. The concentrated solutions of PEG7 HIM2 and PEG7-Lys C-peptide were lyophilized in a tray lyophilizer to white powders of PEG7 HIM2 (4.86 g insulin equivalent) and PEG7-Lys C-peptide (3.7 g). The HPLC and the mass spectral analysis were used to determine the identity and purity of each isolate. A sample of lyophilized material of PEG7 HIM2 was further characterized by additional tests, peptide mapping and biopotency (via mouse blood glucose assay (MBGA)) and compared with that of USP insulin and PEG7 HIM2 obtained via conjugation using USP insulin.

Example 28

Peptide Mapping, Chemical and Potency Comparability of LysB29-PEG7-hexyl-Oligomer Conjugate of Insulin PEG7 HIM2 Produced from Proinsulin Against PEG7 HIM2 Produced from Insulin A. Peptide Mapping Method:

Peptide Mapping by Endoproteinase Glu-C (*Staphylococcus aureus* V8 Protease) Digestion:

The procedure used is based on the method described in the USP monograph for human insulin.

Sample Preparation:

Insulin and insulin conjugate solutions having a concentration of ~0.5 mg/mL were prepared using 100 mM HEPES buffer, pH 7.5, as diluents. The solutions by HPLC using the HPLC method for analysis of Insulin and PEG7 HIM2 to determine the concentration relative to Insulin Standard. The solutions were stored at +5° C. The Endoproteinase Glu-C (from *Staphylococcus aureus* V8) solution having a concentration of 2 mg/mL was prepared in water.

Test Assay:

Placed 0.375 mL of protein solution in a vial, add 30 µL of Endoproteinase Glu-C solution, closed and sealed the vial, then incubated at 25° C. (shaking water bath) for about 4 hours. Added 405 µL of a 50:50 (v/v) solution of 2.0 M ammonium sulfate/0.5 M sulfuric acid to the vial to quench the reaction. The sample was frozen.

Analysis:

Stock samples were analyzed by the HPLC method for the analysis of PEG7 HIM2 and insulin. All digest samples were analyzed by the V8MAP1 HPLC method (below).

Column: Waters DeltaPak C18 column, 150 mm length× 3.9 mm I.D.; 5 µm particle size, 300 Å pore-size stationery phase Column temperature: +40° C.

Detection wavelength: 220 nm

Mobile Phase A: 10% (v/v) methanol in water containing 0.1% TFA

Mobile Phase B: 10% (v/v) methanol in acetonitrile containing 0.1% TFA

Flow Rate: 1 mL/min.

Gradient:

| Time (Minutes) | % Mobile Phase A | % Mobile Phase B |
|---|---|---|
| 0 | 89 | 11 |
| 70 | 67 | 37 |
| 73 | 89 | 11 |
| 75 | 89 | 11 |

TABLE 7

Major Fragments Obtained by Endoproteinase Glu-C Digestion of Human Insulin, USP and PEG7 HIM2 samples produced from Insulin and Proinsulin I

| | | Molecular Weight When Isolated From | | |
|---|---|---|---|---|
| Fragment | | | PEG7 HIM2, Produced from | PEG7 HIM2, Produced from |
| No. | Structure | Human Insulin | insulin | Proinsulin I |
| 1 | [A5–A17 + B1–B13] | 2970 | 2970 | 2970 |
| 2 | [A18–A21 + B14–B21] | 1379 | 1379 | 1378 |
| 3 | [B22–B30] | 1116 | Not present | Not present |
| 3' (Note 1) | | Not present | 1554 (Note 2 and 3) | 1553 (Note 2 and 3) |
| 4 | [A1–A4] | 416 | 416 | 416 |

Notes to Table 7
Note 1: Fragment 3' refers to the peak observed in the peptide map of PEG7 HIM2 that is different from fragment 3 of human insulin.
Note 2: HPLC chromatogram shows a different retention time for this fragment, suggesting fragment has been modified by hexyl-oligomer. The mass spectrum, which shows a psuedo-molecular ion having an m/z ("mass") of 1554 atomic mass units (amu) confirms the structure of this fragment as [B22–B30 + a single molecular weight hexyl-oligomer].
Note 3: HPLC chromatogram shows different retention time for this fragment, suggesting fragment has been modified by hexyl-oligomer. The mass spectrum, which shows an ion having an m/z of 1554, confirms the structure of this fragment as [B22–B30 + a single molecular weight hexyl-oligomer].

Note 1: Fragment 3' refers to the peak observed in the peptide map of PEG7 HIM2 that is different from fragment 3 of human insulin.

Note 2: HPLC chromatogram shows a different retention time for this fragment, suggesting fragment has been modified by hexyl-oligomer. The mass spectrum, which shows a pseudo-molecular ion having an m/z ("mass") of 1554 atomic mass units (amu) confirms the structure of this fragment as [B22-B30+a single molecular weight hexyl-oligomer].

Note 3: HPLC chromatogram shows different retention time for this fragment, suggesting fragment has been modified by hexyl-oligomer. The mass spectrum, which shows an ion having an m/z of 1554, confirms the structure of this fragment as [B22-B30+a single molecular weight hexyl-oligomer].

Figure 17A:
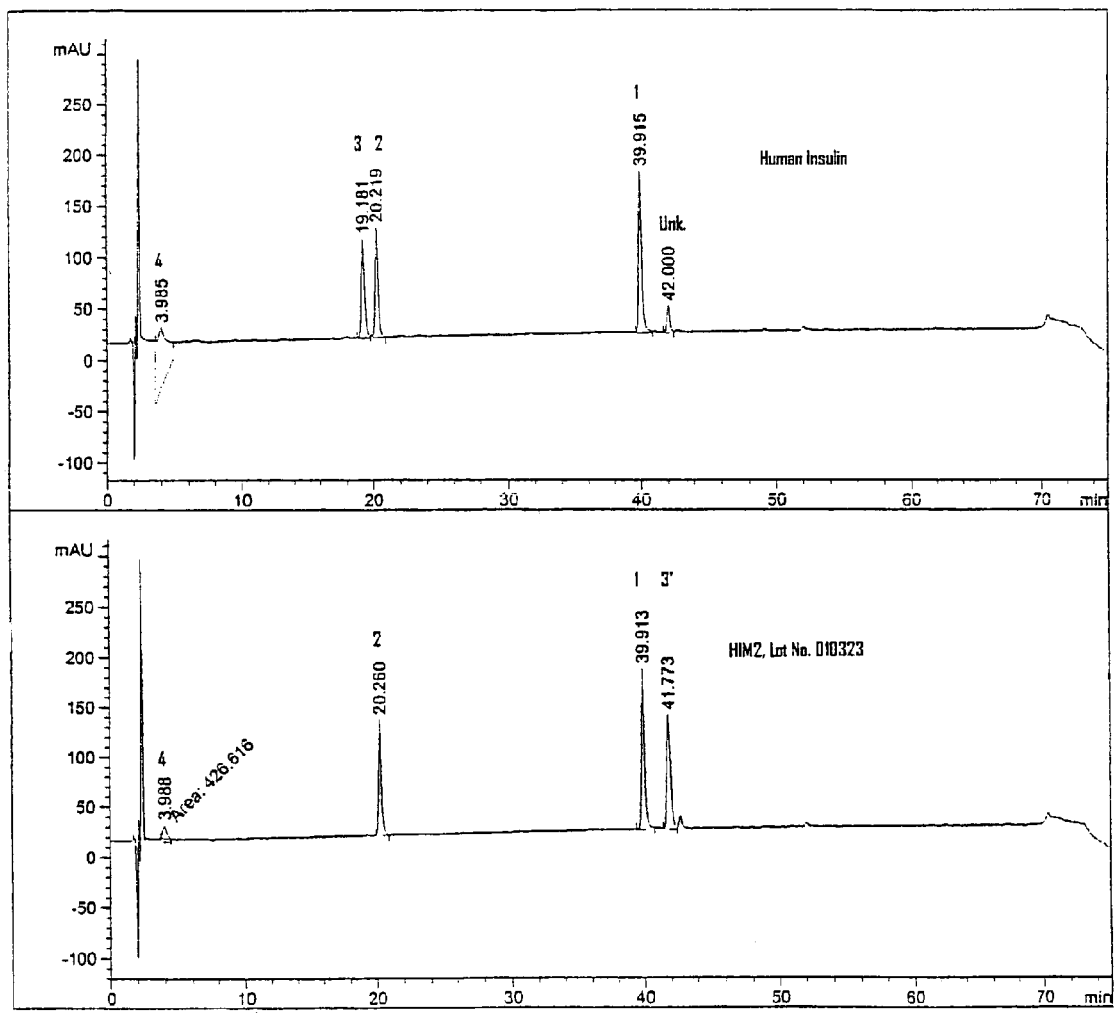
FIGS. 17a and 17b illustrate HPLC chromatograms from peptide mapping of human insulin and PEG7 HIM2.
Figure 17B:
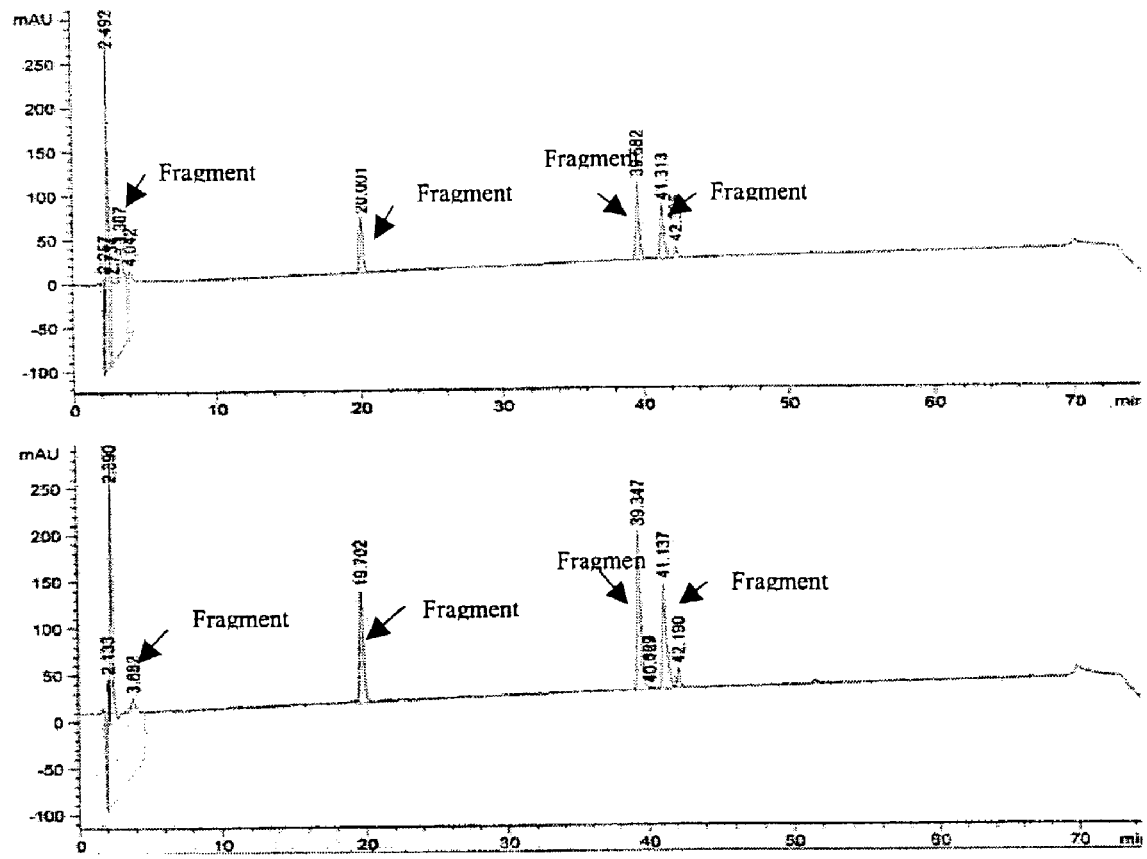

FIGS. 17a and 17b show the HPLC profile of the Glu-C peptidase (VX protease) digestion of the LysB29-PEG7-hexyl-Oligomer conjugate of Insulin (PEG7 HIM2). The peak identified as "unk" is an unknown fragment that is apparently a minor by-product formed under the enzyme digestion conditions. The unidentified fragment is also present in the chromatograms for HIM2 but is not identified by name.

B. Chemical Comparability:

| Control tests | PEG7 HIM2 from USP Insulin | PEG7 HIM2 from Pre-Proinsulin I |
|---|---|---|
| Appearance (Visual) | White Powder | White powder |
| Identity: | | |
| MW (by MALDI/MS) | 6245.2 (M + 1) | 6244 (M + 1) |
| HPLC | Conforms | Conforms |
| Peptide mapping | Conforms | Conforms |
| Purity (HPLC) | 96.1% | 99.3% |
| Related substances (HPLC) | 3.9% | 0.7% |
| Protein content (HPLC) | 95.9% w/w (RH = 23%) | 78.6% w/w (RH = nd) |
| Moisture (Karl Fisher) | 5.7% w/w | 8.7% w/w |

-continued

| Control tests | PEG7 HIM2 from USP Insulin | PEG7 HIM2 from Pre-Proinsulin I |
|---|---|---|
| Acetate (Ion Chromatography) | 0.13% w/w | 2.6% w/w |
| Residual solvents (GC-MS) | ACN 257 ppm | ACN 6.2 ppm Ethanol 4.3 ppm |
| Ammonium ion (Ion Chromatography | 0.4% w/w | 0.52% w/w | nd: not determined

C. Biopotency Method: MBGA

Extended Mouse Blood Glucose Assay (MBGA). Six paired-dose groups of 5 male CF-1 mice (Charles River Laboratories; 25–30 g) received subcutaneous injections of either the insulin conjugate (test article) or recombinant human insulin. The test article was reconstituted with deionized water and dosed at 100, 66.6, 43.3, 30, 20, and 13.3 µg/kg. Insulin was reconstituted with deionized water and dosed at 50, 33.3, 21.7, 15, 10, and 6.7 µg/kg. After receiving a subcutaneous dose in the pocket formed by the thigh and groin, animals were returned to their cages for 30 minutes at room temperature and then were quickly anesthetized and terminally bled. Blood samples were collected in heparin tubes for glucose assay. If glucose assay was delayed, the tubes were stored in ice water and re-warmed to room temperature before assay.

Plasma glucose was measured with a glucometer (e.g., One Touch® Basic; Lifescan), which was calibrated at the beginning of each day of use according to the manufacturer's instructions. The potency of the insulin conjugate was then calculated relative to the standard curve that was generated for the recombinant human insulin response. Calculations were based upon the assumption that recombinant human insulin has a potency of 27.4 IU/mg.

Figure 18A:
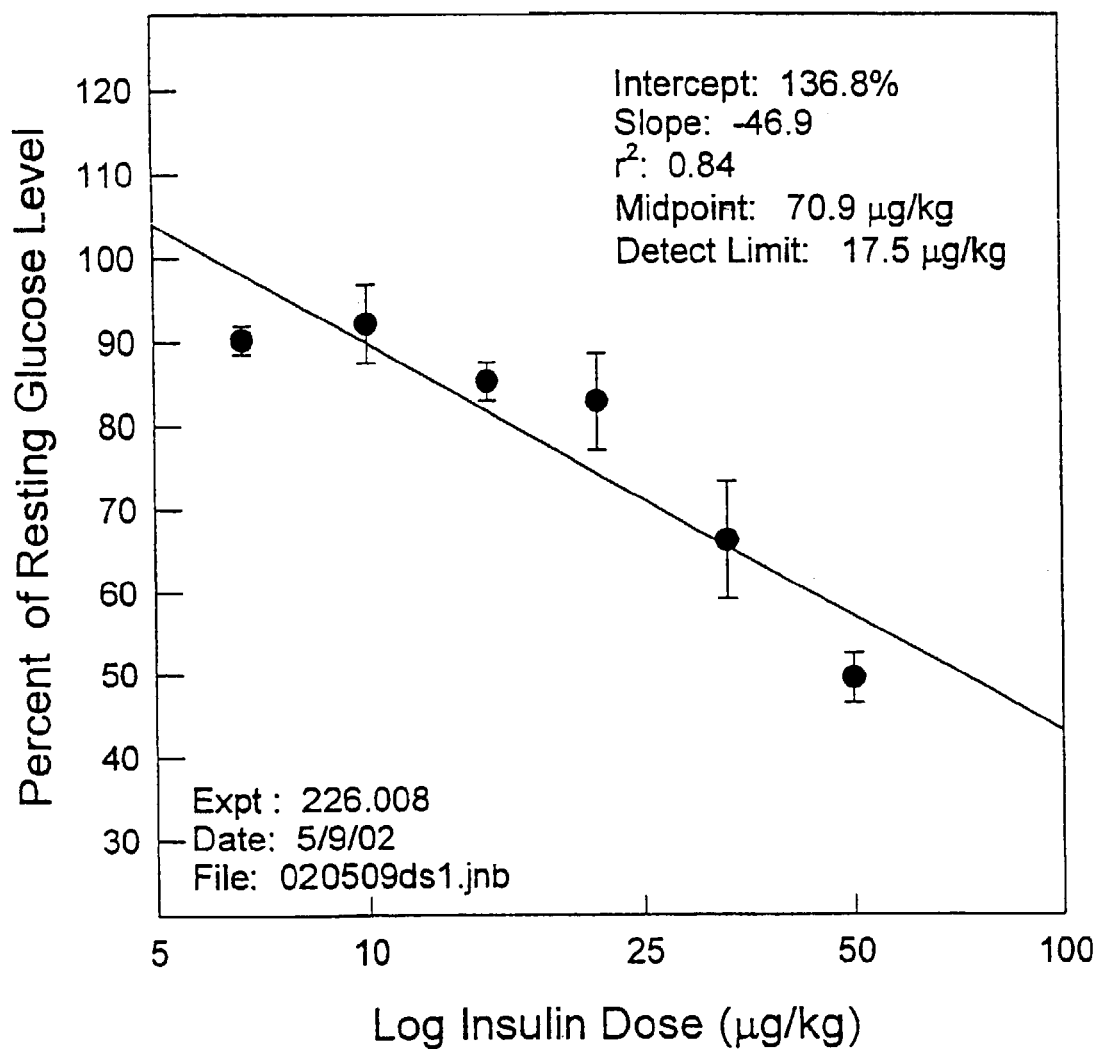
FIGS. 18a and 18b illustrate the MBGA biopotency profiles of oligomer conjugates of this invention produced from insulin.
Figure 18B:
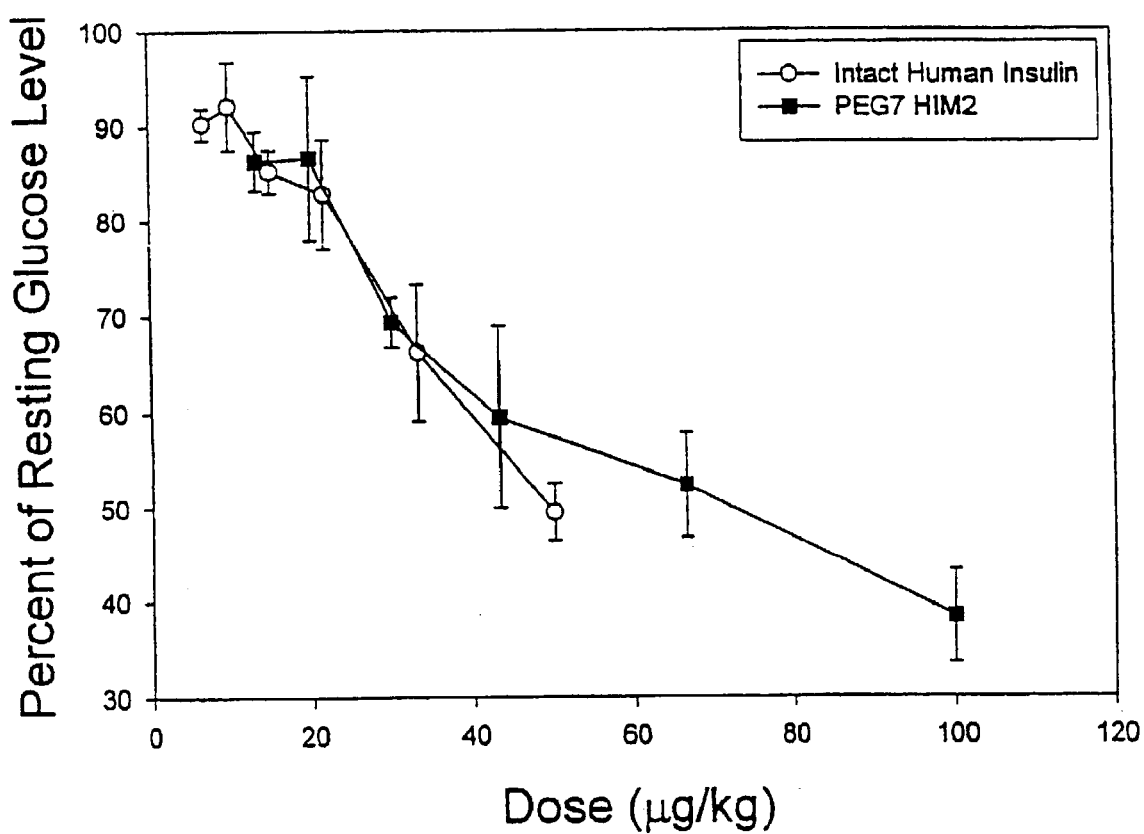
Figure 19A:
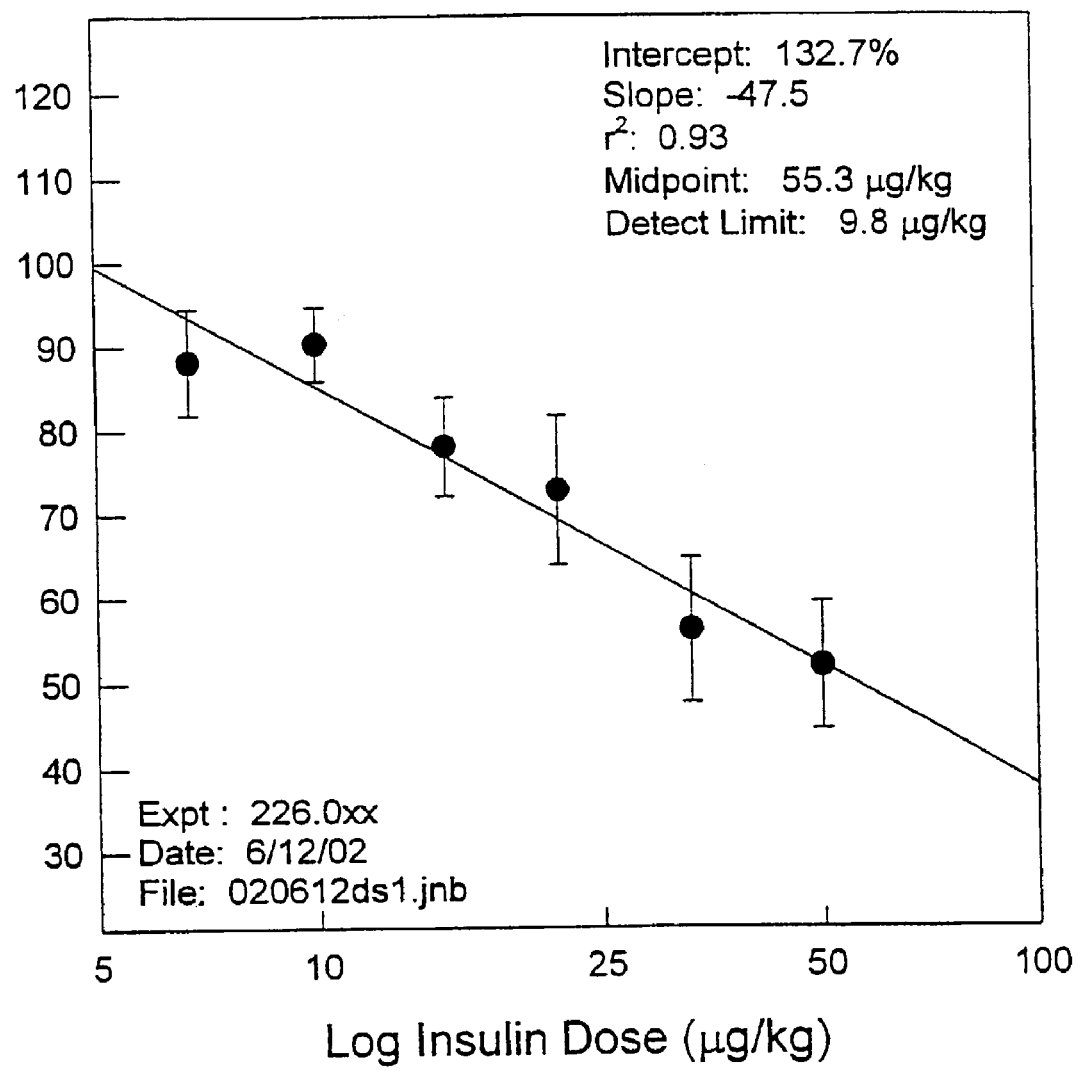
FIGS. 19a and 19b illustrate the MBGA biopotency profiles of oligomer conjugates of this invention produced from proinsulin.
Figure 19B:
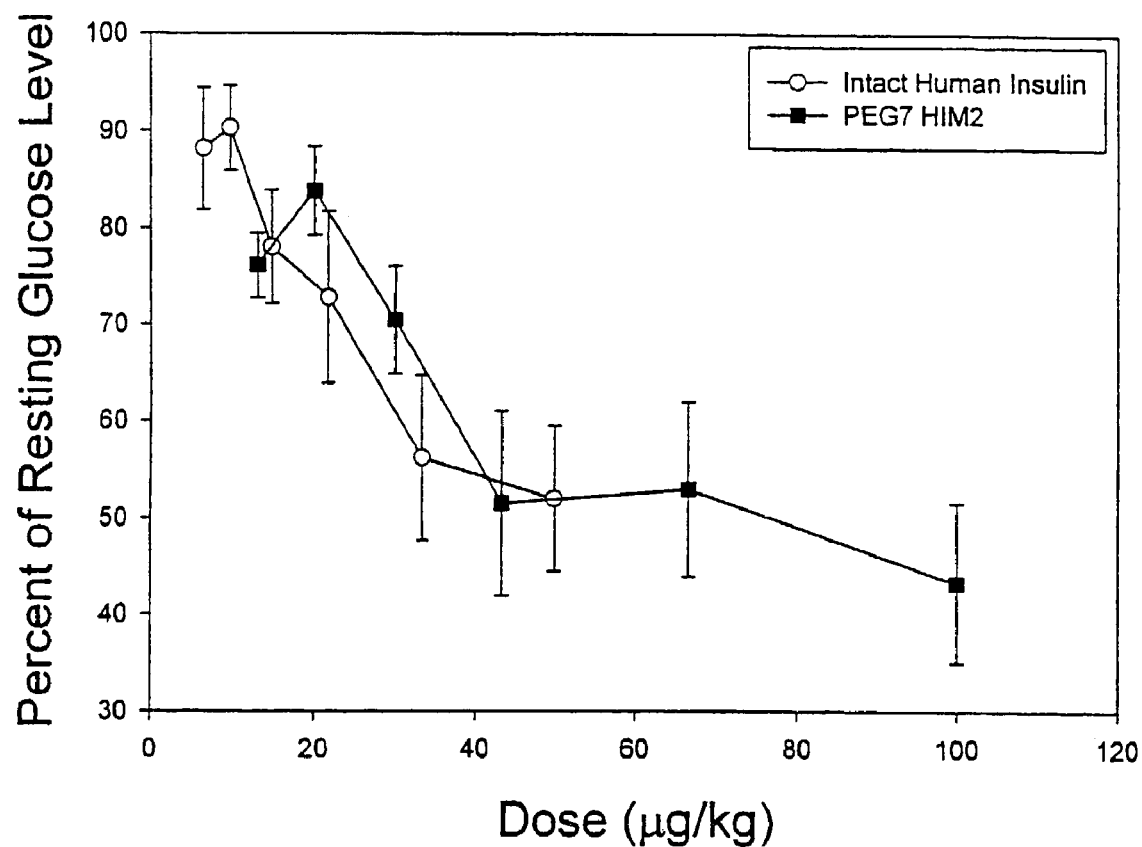

FIGS. 18a & b and 19a & b show the MBGA biopotency profiles of Insulin and PEG7 HIM2 insulin.

| Control tests | PEG7 HIM2 from USP Insulin | PEG7 HIM2 from Pre-Proinsulin I |
|---|---|---|
| Biopotency by MBGA | 76–94% | 84% |

Example 29
Preparation of $Lys_{B29}$-Oligomer-Conjugated Insulin and LysB29, PheB1-Di (Oligomer) Conjugated Insulin as Described in Example 21

(a) Conjugation of Natural Human Proinsulin. Natural human proinsulin (Sigma Chemical Co) ($3.20 \times 10^{-4}$ mmol) was dissolved in 5 mL of DMSO. To the solution was added 45 µL of triethylamine. The solution was allowed to stir for 5 minutes before a solution of activated PEG7-hexyl oligomer ($6.4 \times 10^{-4}$ mmol) in acetonitrile was added. After the reaction had progressed such that HPLC analysis indicated that the proinsulin had been consumed (or the concentration of proinsulin was no longer decreased), the reaction was quenched by addition of 0.5 mL of 5% aqueous trifluoroacetic acid solution. The reaction mixture was then processed and exchanged into 100 mM Tris-HCl Buffer, pH 7.6.

(b) Enzyme Cocktail Cleavage of Oligomer-Conjugated Natural Proinsulin. An aliquot of the Tris-HCl solution of the product mixture was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The crude mixture (1 mol. eq.) was then allowed to react with trypsin ($1.39 \times 10^{-3}$ mol. eq.) and carboxypeptidase B ($4.56 \times 10_{-4}$ mol. eq.). After 30 minutes, the reaction was quenched by addition of 1% trifluoroacetic acid in acetonitrile. The product mixture of the reaction was processed and analyzed by HPLC. Retention time (versus that of reference standards) and mass spectral analysis were used to determine identity. The products and expected products of the reaction were Insulin, LysB29-hexyl-PEG7-oligomer-conjugated Insulin, PheB1,LysB29 Di (hexyl-PEG7-oligomer) conjugated insulin and Lys-hexyl-PEG7-oligomer C-peptide (Table 8)

TABLE 8

Figure 28:
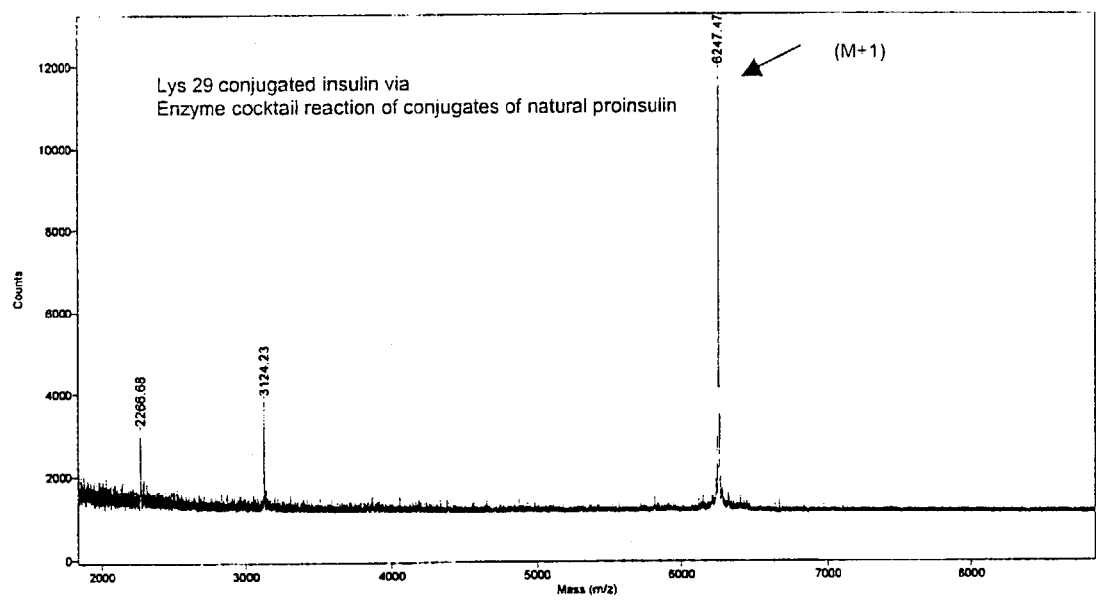
FIG. 28 illustrates a MALDI-Mass Spectrum of LysB29-Hexyl-PEG7-Oligomer Conjugate from Enzyme Cocktail reaction of Hexyl-PEG7-Oligomer conjugates of Natural Proinsulin.
Figure 29:
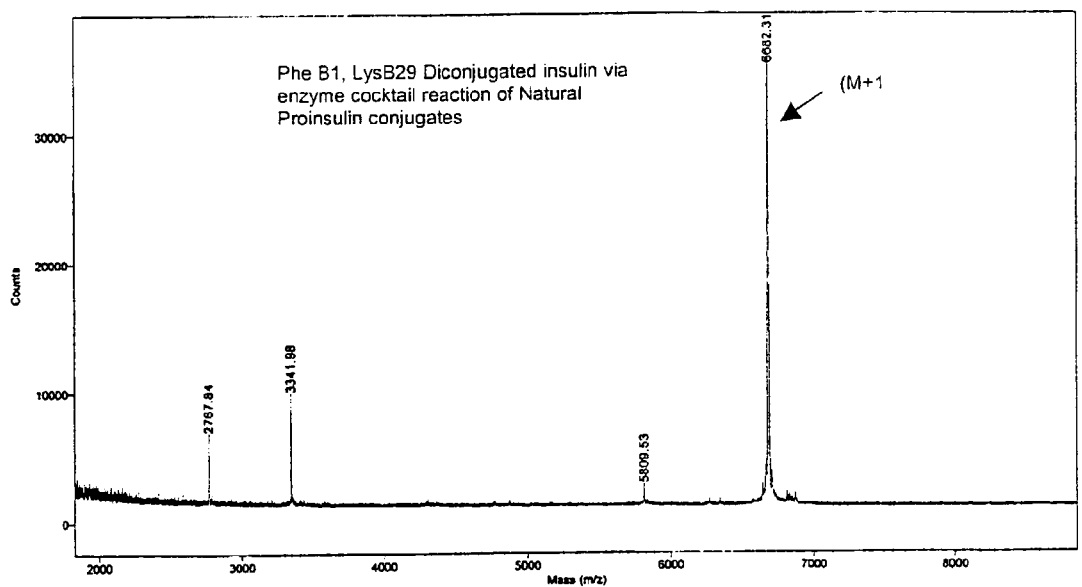
FIG. 29 illustrates a MALDI-Mass Spectrum of PheB1, LysB29 Di (Hexyl-PEG7-Oligomer) Conjugate from Enzyme Cocktail Reaction of Hexyl-PEG7-Oligomer Conjugates of Natural Proinsulin.

| Conjugates in crude mixture | Products and (Expected Products) | MW by mass spec |
|---|---|---|
| Natural Proinsulin Mono A (Lys64 conjugated proinsulin) | Insulin<br>Des Thr insulin<br>(Lys64-hexyl-PEG7-oligomer-conjugated C-peptide), | 5009 (M + 1) |
| Natural Proinsulin III Mono B (Lys29 conjugated proinsulin) | (Diarginal insulin, Monoarginal insulin), (Arg65Lys$^{64}$-hexyl-PEG7-oligomer-conjugated C-peptide), (Des Arg 31, 32 proinsulin) and (Des 65, 64 proinsulin) | |
| Natural Proinsulin Di (LysB29 and Lys64 conjugated proinsulin) | Lys-hexyl-PEG7-oligomer-conjugated Insulin,<br>C-peptide | 6244 (M + 1) (FIG. 28) |
| Proinsulin III Tri (LysB29, Lys 64 and PheB1 conjugated proinsulin) | (Des Arg 31, 32 Lys $^{B29}$-hexyl-PEG7-oligomer conjugated proinsulin), (Des 65, 64 Lys $^{B29}$-hexyl-PEG7-oligomer conjugated proinsulin), (Arg31, 32 Lys$^{64}$-hexyl-PEG7-oligomer conjugated C-peptide) and (Arg32 Lys$^{64}$-hexyl-PEG7-oligomer conjugated C-peptide) | |
| | PheB1, LysB29 Di [Hexyl-PEG7-Oligomer]-Conjugated Insulin, Lys64-hexyl-PEG7-oligomer-conjugated C-peptide<br>(Lys $^{B29}$-hexyl-PEG7-oligomer conjugated Insulin-Arg$^{31}$–Arg$^{32}$), (Des 65 Lys $^{64}$Lys $^{B29}$-Phe B1-Tri (hexyl-PEG7-oligomer) conjugated proinsulin), (Des Arg 31, 32 Lys $^{64}$Lys B29, Phe B1-Tri(hexyl-PEG7-oligomer) conjugated proinsulin), (Arg31, 32 Lys$^{64}$-hexyl-PEG7-oligomer conjugated C-peptide) and (Arg32 Lys$^{64}$-hexyl-PEG7-oligomer conjugated C-peptide) | 6682 (M + 1) (FIG. 29) |

Example 30

Preparation of Mono-dispersed $Lys^{B29}$-Oligomer Conjugated Insulin (a) Conjugation of Recombinant Proinsulin II. Recombinant Proinsulin II (MW 11,133 Daltons) was obtained from Itoham Foods, Inc. of Ibaraki Pref, Japan. The Recombinant Proinsulin II had a leader peptide and a C-peptide that were each devoid of Lysine residues. A $2.55 \times 10^{-3}$ mmol portion of recombinant Proinsulin II was dissolved in 10 mL of DMSO. To the solution was added 355 µL of triethylamine. The resulting solution was allowed to stir for 5 minutes, and then a solution of activated methylheptayethylene glycol ((PEG7)-hexyl oligomer) ($5.10 \times 10^{-3}$ mmol) in 0.6 mL acetonitrile was added. The course of the reaction was monitored by HPLC. After the reaction appeared to be complete, it was quenched by addition of 3.7 mL of 5% aqueous trifluoroacetic acid solution. The reaction mixture was then processed and exchanged into 100 mM Tris-HCl Buffer, pH 7.6.

(b) Enzyme Cocktail Cleavage of Oligomer-Conjugated Recombinant Proinsulin II. The Tris-HCl solution of the product mixture was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.399 μmol/mL) was allowed to react with trypsin ($5.57 \times 10^{-4}$ μmol/mL) and carboxypeptidase B ($1.82 \times 10^{-4}$ μmol/mL). After 30 minutes, the reaction was quenched by addition of 550 μL of 1% trifluoroacetic acid in acetonitrile. The major products were identified by HPLC retention time (relative to that of known reference standards) and mass spectral analysis. Insulin (8%) and $Lys_{B29}$-hexyl-PEG7- oligomer-conjugated Insulin (60%) and other (30%) were thus obtained.

Example 31

Isolation of the Products of Oligomer-Conjugation of Recombinant Proinsulin II

Each major product from the conjugation reaction described in Example 30(a) was isolated using reversed-phase HPLC. A column (1.0 cm. i.d.×25 cm. length) was packed with a commercially available C18 stationary phase known to be useful for the resolution of polypeptides and proteins, and then was incorporated into an HPLC system. The system was equilibrated with elution buffer that was a mixture of 75% mobile phase A ($H_2O$ with 0.1% trifluoroacetic acid) and 25% mobile phase B (acetonitrile with 0.1% trifluoroacetic acid) that was delivered at a flow rate of 5 mL/min. The Tris-HCl solution of the product mixture from Example 30(a) was applied to the column, and the major products were separated and eluted using a gradient elution in which the composition of the elution buffer was changed from 25% mobile phase B to 35% mobile phase B over 120 minutes. Each of the fractions collected was analyzed by HPLC to determine the identity and purity of the product contained therein. Common fractions of each product (Proinsulin II monoconjugate ("Proinsulin II Mono") and diconjugate ("Proinsulin II Di") were then pooled, and the solvent was removed by rotary evaporation. The identity and purity of each product were determined by HPLC and mass spectrometric analyses.

Example 32

Enzyme Cocktail Cleavage of Isolated Conjugates of Recombinant Proinsulin II

Each Proinsulin II conjugate (Proinsulin II Mono, Di or Tri) that was isolated using the procedure described in Example 30 was dissolved in 100 mM Tris-HCl Buffer, pH 7.6, and an aliquot of the solution was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The conjugate (0.127 μmol/mL) was allowed to react with trypsin ($1.77 \times 10^{-4}$ μmol/mL) and carboxypeptidase B ($5.77 \times 10^{-5}$ μmol/mL). After 30 minutes, the reaction was quenched by addition of 250 μL of 1% trifluoroacetic acid in acetonitrile. Isolation of the major products followed by identification by HPLC retention time against reference standards and mass spectral analysis showed that Insulin, B-29 acylated Insulin-hexyl-PEG7 and N-amino acylated artificial C-peptide were produced in the reaction. The products and yields of each reaction are illustrated in Table 9 mono-dispersed.

TABLE 9

Figure 30:
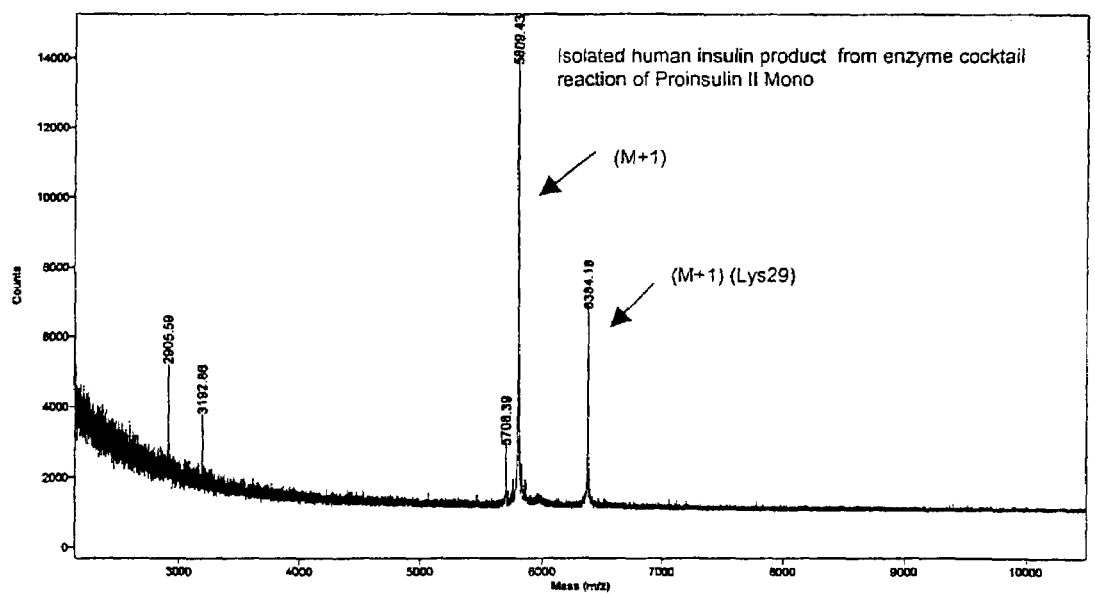
FIG. 30 illustrates a MALDI-Mass Spectrum of Human insulin isolated from Enzyme Cocktail reaction of Proinsulin II Mono Conjugate of Hexyl-PEG7-Oligomer(Proinsulin Mono)
Figure 31:
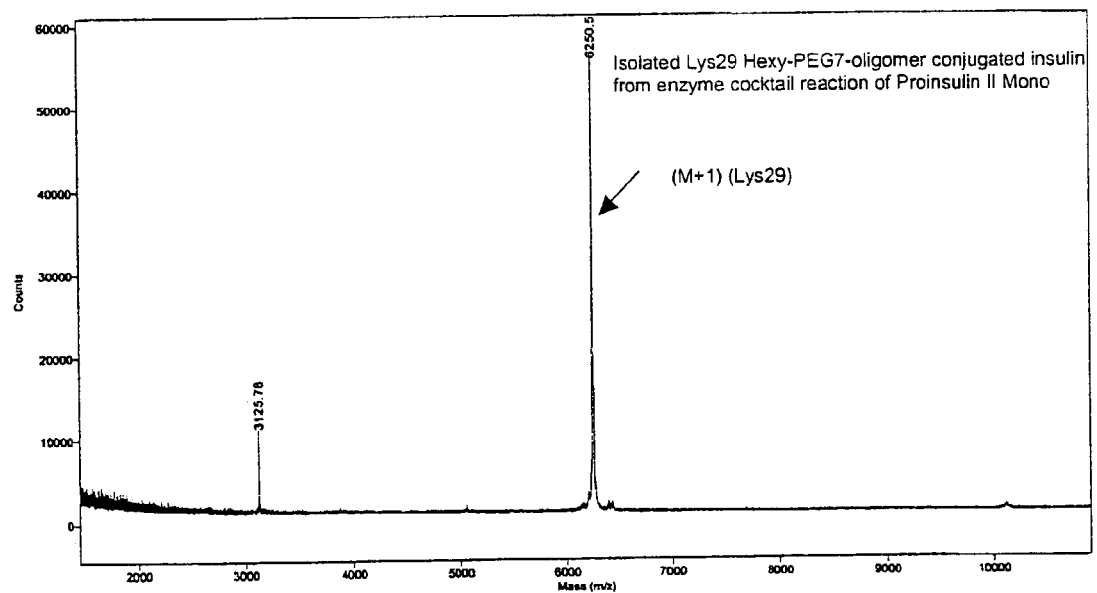
FIG. 31 illustrates MALDI-Mass Spectrum of Lys29-Hexyl-PEG7-Oligomer conjugate of insulin from Enzyme Cocktail reaction of Proinsulin II Mono Conjugate of Hexyl-PEG7-Oligomer (Proinsulin II Mono)
Figure 32:
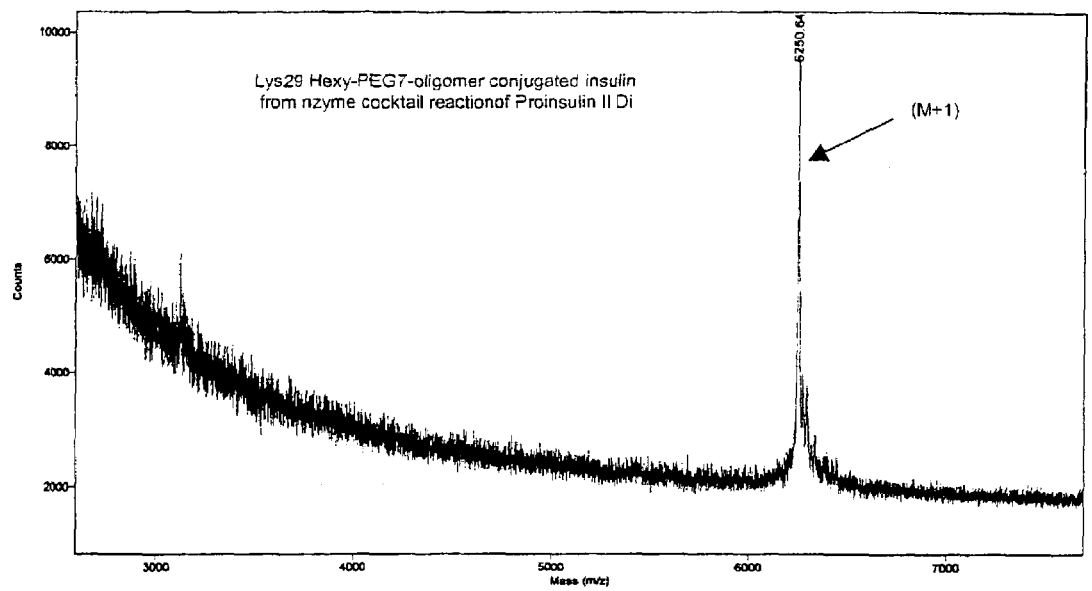
FIG. 32 illustrates a MALDI-Mass Spectrum of Lys29-Hexyl-PEG7-Oligomer conjugate of insulin from Enzyme Cocktail reaction of Proinsulin II Di Conjugate of Hexyl-PEG7-Oligomer (Proinsulin II DI)

| Conjugate | Products | Yield |
|---|---|---|
| | mono-dispersed | |
| Proinsulin II Mono | Insulin (MW 5808) | 8% (FIG. 30) |
| | $Lys^{B29}$-hexyl-PEG7-oligomer conjugated insulin (MW 6244) | 90% (FIG. 31) |
| | N-Hexyl-PEG7-oligomer conjugated artificial C-peptide | |
| Proinsulin II Di | $Lys^{B29}$-hexyl-PEG7-oligomer-conjugated insulin (MW6244) | 92% (FIG. 32) |

Example 33

Preparation of $Lys^{B29}$-Oligomer-Conjugated Insulin (a) Conjugation of Recombinant Proinsulin III. Recombinant Proinsulin III (9990 Daltons) was obtained from another source ("CKD"). A $2.32 \times 10^{-3}$ mmol portion of proinsulin III is dissolved in 10 mL of borate buffer (100 mM, pH 9.5). To the resulting solution is added a solution of activated methylheptaethylene glycol ((PEG7)-hexyl oligomer) ($9.30 \times 10^{-3}$ mmol) in 3–6 mL acetonitrile. The course of the conjugation (acylation) reaction is monitored by HPLC. When the reaction appears to be complete, it is quenched by adjusting the pH of the solution to pH<6 with dilute hydrochloric acid. The reaction mixture is then processed and exchanged into 100 mM Tris-HCl Buffer, pH 7.6.

(b) Enzyme Cocktail Cleavage of Oligomer-Conjugated Recombinant Proinsulin III

An aliquot of the Tris-HCl solution of the product mixture is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture (0.424 μmol/mL) is then allowed to react with trypsin ($5.97 \times 10^{-4}$ μmol/mL) and carboxypeptidase B ($1.93 \times 10^{-4}$ μmol/mL). After 30 minutes, the reaction is quenched by the addition of 1.58 mL of 1% trifluoroacetic acid in acetonitrile. The major products are identified by HPLC retention time (relative to the retention times of known reference standards) and mass spectral analysis. Insulin and $Lys^{B29}$-Hexyl-PEG7-Oligomer-Conjugated Insulin are thus obtained. The product mixture from the reaction is processed and analyzed by HPLC. The HPLC retention time relative to that of reference standards and mass spectral analysis are used to determine the identity and purity of each product (Table 10).

TABLE 10

Oligomer-conjugates of Proinsulin I and Products (or Expected Products) from Enzyme Cocktail Cleavage of Each

| Conjugate | Expected Products |
|---|---|
| Proinsulin III Mono A (Proinsulin I conjugated at Lys 64) | Insulin, Lys64-hexyl-PEG7-oligomer-conjugated C-peptide, Diarginal insulin, Monoarginal insulin, Arg65Lys$^{64}$-hexyl-PEG7-oligomer-conjugated C-peptide, Des Arg 31, 32 proinsulin, Des 65, 64 proinsulin, Arg-Leader peptide and Leader peptide |
| Proinsulin I Mono B (proinsulin I conjugated at B29) | Lys $^{B29}$-Hexyl-PEG7-oligomer-conjugated insulin, C-peptide Des Arg 31, 32 Lys $^{B29}$-hexyl-PEG7-oligomer conjugated proinsulin or proinsulin III, Des 65, 64 Lys $^{B29}$-hexyl-PEG7-oligomer conjugated proinsulin or proinsulin III, Arg31, 32 Lys$^{64}$-hexyl-PEG7-oligomer conjugated C-peptide, Arg32 Lys$^{64}$-hexyl-PEG7-oligomer conjugated C-peptide, Arg-Leader peptide and Leader peptide |
| Proinsulin III Di (proinsulin III conjugated at B29 and Lys 64) | LysB29-Hexyl-PEG7-Oligomer-Conjugated Insulin Lys$^{64}$-hexyl-PEG7-oligomer conjugated C-peptide, Des 65 Lys $^{64}$Lys $^{B29}$-Di (hexyl-PEG7-oligomer) conjugated proinsulin or proinsulin III, Des Arg 31, 32 Lys $^{64}$Lys $^{B29}$-Di(hexyl-PEG7-oligomer) conjugated proinsulin or proinsulin III), Arg31, 32 Lys$^{64}$-hexyl-PEG7-oligomer conjugated C-peptide, Arg32 Lys$^{64}$-hexyl-PEG7-oligomer conjugated C-peptide, Arg-Leader peptide and Leader peptide |
| Proinsulin III Tri (proinsulin III conjugated at B29, Lys 64 and N-amino terminal of Leader peptide) | LysB29-Hexyl-PEG7-Oligomer-Conjugated Insulin Lys-hexyl-PEG7-oligomer-conjugated C-peptide) Lys $^{B29}$-hexyl-PEG7-oligomer conjugated Insulin-Arg$^{31}$–Arg$^{32}$, Des 65 Lys $^{64}$Lys $^{B29}$-Di (hexyl-PEG7-oligomer) conjugated proinsulin or proinsulin III, Des Arg 31, 32 Lys $^{64}$Lys $^{B29}$-Di(hexyl-PEG7-oligomer) conjugated proinsulin or proinsulin III, Arg31, 32 Lys$^{64}$-hexyl-PEG7-oligomer conjugated C-peptide, Arg32 Lys$^{64}$-hexyl-PEG7-oligomer conjugated C-peptide, , Hexyl-PEG7-oligomer conjugated Leader peptide-Arg and Hexyl-PEG7-oligomer Leader peptide |

Example 34

Preparation of LysB$_{29}$-Oligomer-Conjugated desThr Insulin from desThr Single Chain Insulin Precursor (a) Conjugation of desThr Miniproinsulin. Recombinant desThr single chain insulin precursor (desThr miniproinsulin) (MW 5688 Daltons) is obtained. An amount (0.0195 mmol) is dissolved in 5 mL of borate buffer (100 mM, pH 9.5) and the pH is adjusted back to pH 9.97. To The resulting solution is added to a solution of activated methylheptaethylene glycol ((PEG7)-hexyl oligomer) (0.024 mmol) in 1 mL ethanol. The course of the conjugation (acylation) reaction is monitored by HPLC. When the reaction appears to be complete, it is quenched by adjusting the pH of the solution to pH<6 with dilute hydrochloric acid. The reaction mixture is then processed and exchanged into 100 mM Tris-HCl Buffer, pH 7.6. The HPLC chromatogram of the final reaction mixture shows the following composition: unreacted miniproinsulin (20.7%), LysB29 conjugated miniproinsulin (71.1%) and PheB1, LysB29 diconjugated miniproinsulin (6.2%).

From a portion of the above reaction mixture, each major product from the conjugation reaction described above is isolated using reversed-phase HPLC. A column (1.0 cm. i.d.×25 cm. length) is packed with a commercially available C18 stationary phase known to be useful for the resolution of polypeptides and proteins, and then is incorporated into an HPLC system. The system is equilibrated with elution buffer that is a mixture of 75% mobile phase A (H$_2$O with 0.1% 15 20 25 30 trifluoroacetic acid) and 25% mobile phase B (acetonitrile with 0.1% trifluoroacetic acid) that is delivered at a flow rate of 5 mL/min. The Tris-HCl solution of the product mixture is applied to the column, and the major products are separated and eluted using a gradient elution in which the composition of the elution buffer is changed from 25% mobile phase B to 35% mobile phase B over 120 minutes. Each of the fractions that are collected are analyzed by HPLC to determine the identity and purity of the product contained therein. Common fractions of each product (unreacted miniproinsulin, miniproinsulin monoconjugate and miniproinsulin diconjugate) are then pooled, and the solvent is removed by rotary evaporation. The identity and purity of each product is determined by HPLC and mass spectrometric analyses.

(b) Enzyme Cocktail Cleavage of Oligomer-Conjugated Recombinant desThr Miniproinsulin. An aliquot of the Tris-HCl solution of the product mixture is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture (0.424 µmol/mL) is then allowed to react with trypsin (5.97×10$^{-4}$ µmol/mL) and carboxypeptidase B (1.93×10$^{-4}$ µmol/mL). After 60 minutes, the reaction is quenched by the addition of 1.58 mL of 1% trifluoroacetic acid in acetonitrile. The major products are identified by HPLC retention time (relative to the retention times of known reference standards) and mass spectral analysis. $Lys_{B29}$-Hexyl-PEG7-Oligomer-Conjugated desThr Insulin, LysB29, PheB1-Di (Hexyl-PEG7-Oligomer)-Conjugated desThr Insulin and desThr Insulin are thus obtained. The product mixture from the reaction is processed and analyzed by HPLC. The HPLC retention time relative to that of reference standards and mass spectral analysis are used to determine the identity and purity of each product (Table 11).

TABLE 11

Oligomer-conjugates of desThr Miniproinsulin and Products (or Expected Products) from Enzyme Cocktail Cleavage of Each

| Conjugate | Expected Products |
|---|---|
| Miniproinsulin LysB29 monoconjugate | Lys29-hexyl-PEG7-oligomer-conjugated DesThr Insulin |
| Miniproinsulin PheB1, LysB29-diconjugate | PheB1, Lys29-Di(Hexyl-PEG7-oligomer)-conjugated desThr insulin |

Example 35

Preparation of $Lys_{64}$-Oligomer-Conjugated C-Peptide from Pro C-Peptide (a) Conjugation of Synthetic Pro C-peptide. Synthetic pro C-peptide (31–65) (Arg-Arg-human C-peptide-Arg) (MW 3617 Daltons) is purchased from American Peptide Company, USA. A $2.32 \times 10^{-3}$ mmol portion of C-peptide is dissolved in 10 mL of borate buffer (100 mM, pH 9.5). To the resulting solution is added a solution of N-hydroxy succinimide activated methylheptaethylene glycol ((PEG7)-hexyl oligomer) ($9.30 \times 10^{-3}$ mmol) in 3–6 mL acetonitrile. The course of the conjugation (acylation) reaction is monitored by HPLC. When reaction appears to be complete, it is quenched by adjusting the pH of the solution to pH<6 with dilute hydrochloric acid. The reaction mixture is then processed and exchanged into 100 mM Tris-HCl Buffer, pH 7.6.

(b) Enzyme Cocktail Cleavage of Oligomer-Conjugated Pro C-Peptide (31–65).

An aliquot of the Tris-HCl solution of the product mixture is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture (0.424 µmol/mL) is then allowed to react with trypsin ($5.97 \times 10^{-4}$ µmol/mL) and carboxypeptidase B ($1.93 \times 10^{-4}$ µmol/mL). After 30 minutes, the reaction is quenched by the addition of 1.58 mL of 1% trifluoroacetic acid in acetonitrile. The major products are identified by HPLC retention time (relative to the retention times of known reference standards) and mass spectral analysis. Human C-peptide (33–63) and $Lys_{64}$-Hexyl-PEG7-Oligomer-Conjugated C-peptide are thus obtained. The product mixture from the reaction is processed and analyzed by HPLC. The HPLC retention time relative to that of reference standards and mass spectral analysis are used to determine the identity and purity of each product (Table 12).

TABLE 12

Oligomer-conjugates of Pro C-peptide and Products (or Expected Products) from Enzyme Cocktail Cleavage

| Conjugate | Expected Products |
|---|---|
| Pro C-peptide Mono Conjugate(Lys 64) (conjugated at Lys64) | Lys64-hexyl-PEG7-oligomer-conjugated C-peptide, Arg65Lys$^{64}$-hexyl-PEG7-oligomer-conjugated C-peptide, Arg 32, Lys64-hexyl-PEG7-oligomer-conjugated C-peptide |
| Pro C-peptide conjugate(Arg31) (conjugated at Arg 31) | C-peptide, Arg31-C-peptide |
| Pro C-peptide Di conjugate (conjugated at Arg31 and Lys 64) | Lys64-hexyl-PEG7-oligomer-conjugated C-peptide, Arg65Lys$^{64}$-hexyl-PEG7-oligomer-conjugated C-peptide, Arg 32, Lys64-hexyl-PEG7-oligomer-conjugated C-peptide |

Example 36

Figure 20:
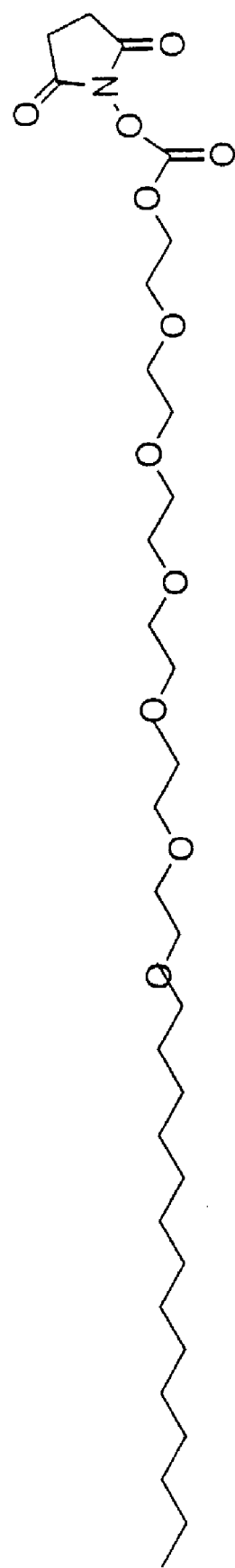
FIG. 20 illustrates the structure of an activated hexaethyleneglycol monohexadecylether (hexadecyl-PEG6 activated oligomer)
Figure 21:
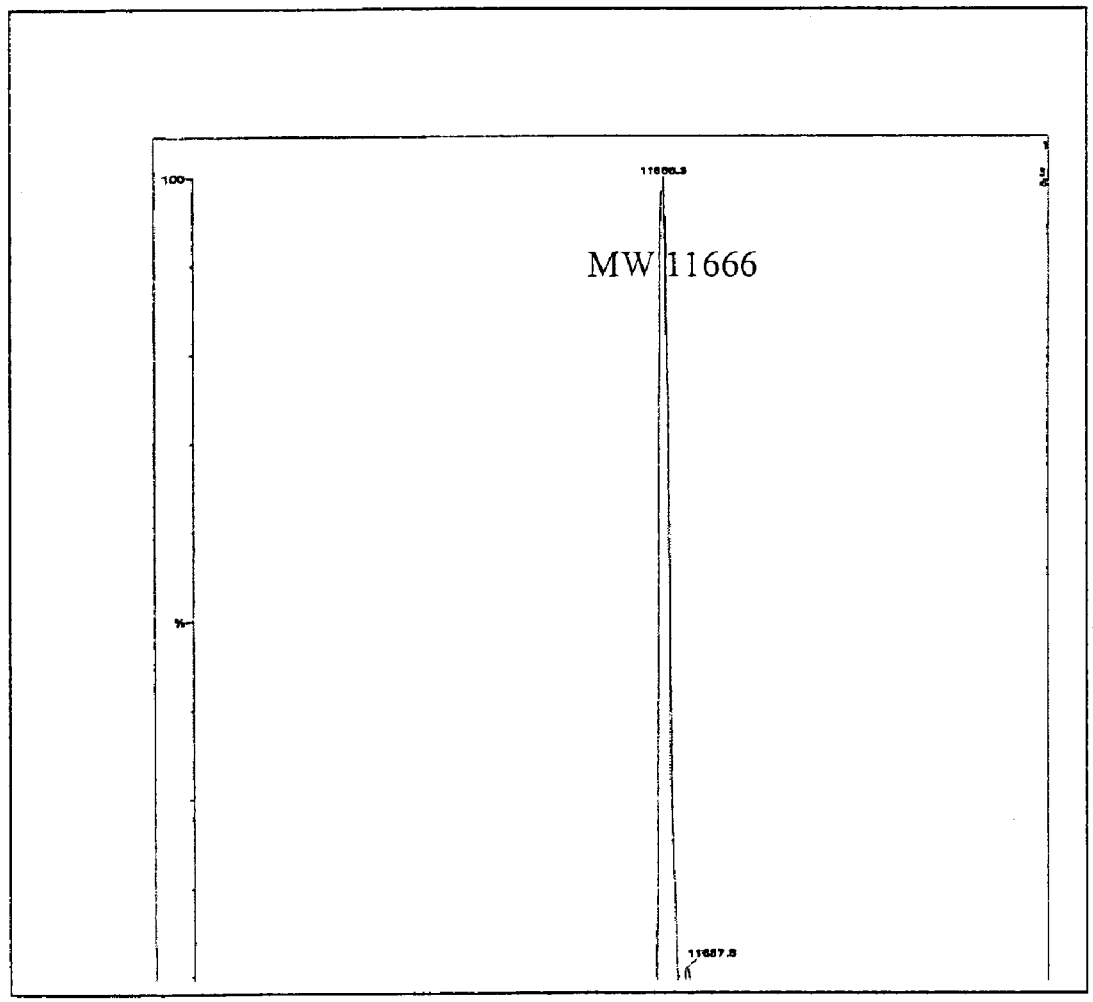
FIG. 21 illustrates a mass spectrum of Proinsulin II Mono B Conjugate of HexadecylPEG6.
Figure 22:
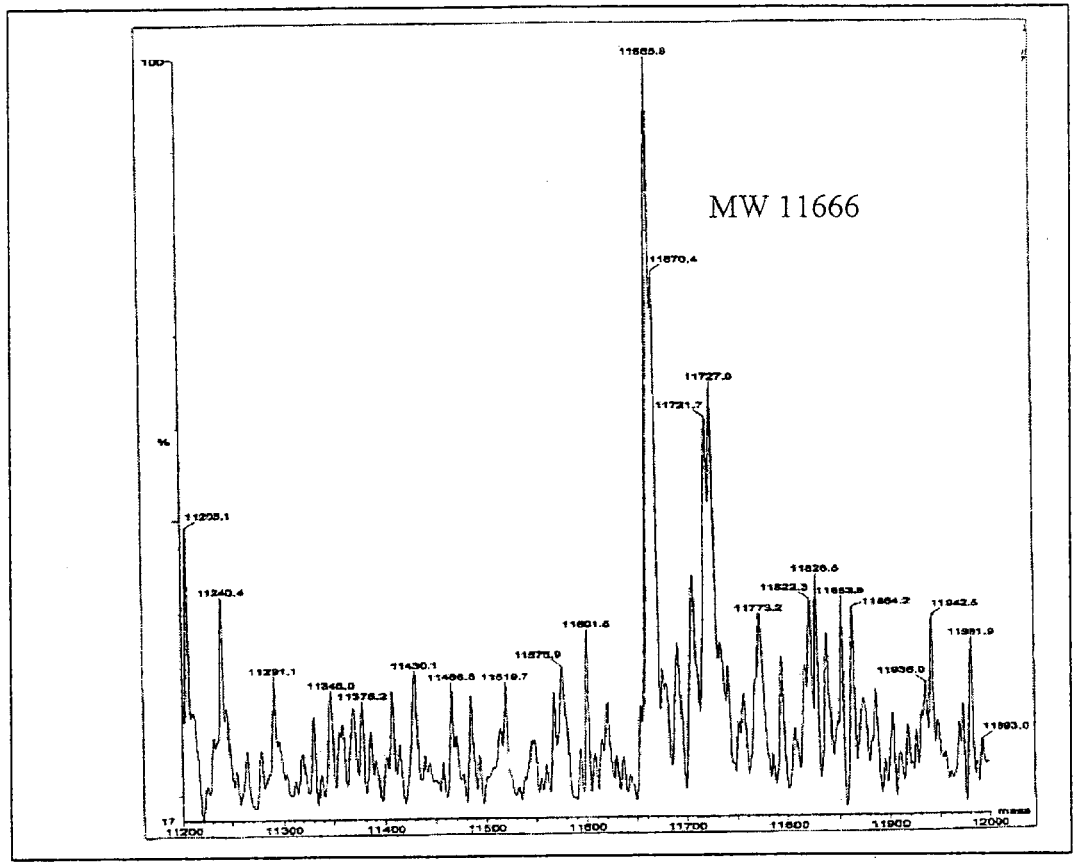
FIG. 22 illustrates a mass spectrum of Proinsulin II Mono A Conjugate of HexadecylPEG6.
Figure 23:
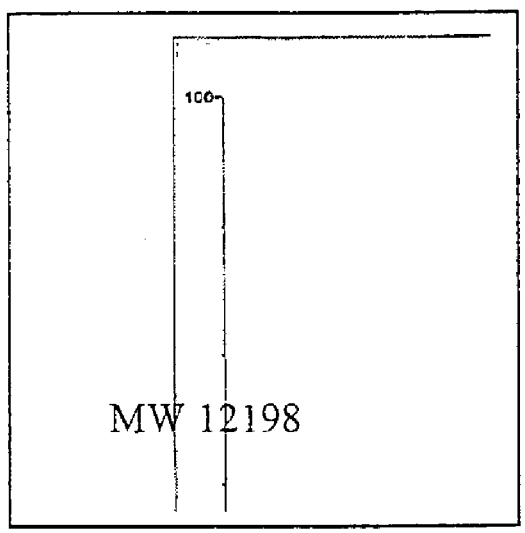
FIG. 23 illustrates a mass spectrum of Proinsulin II Di Conjugate HexadecylPEG6.
Figure 24:
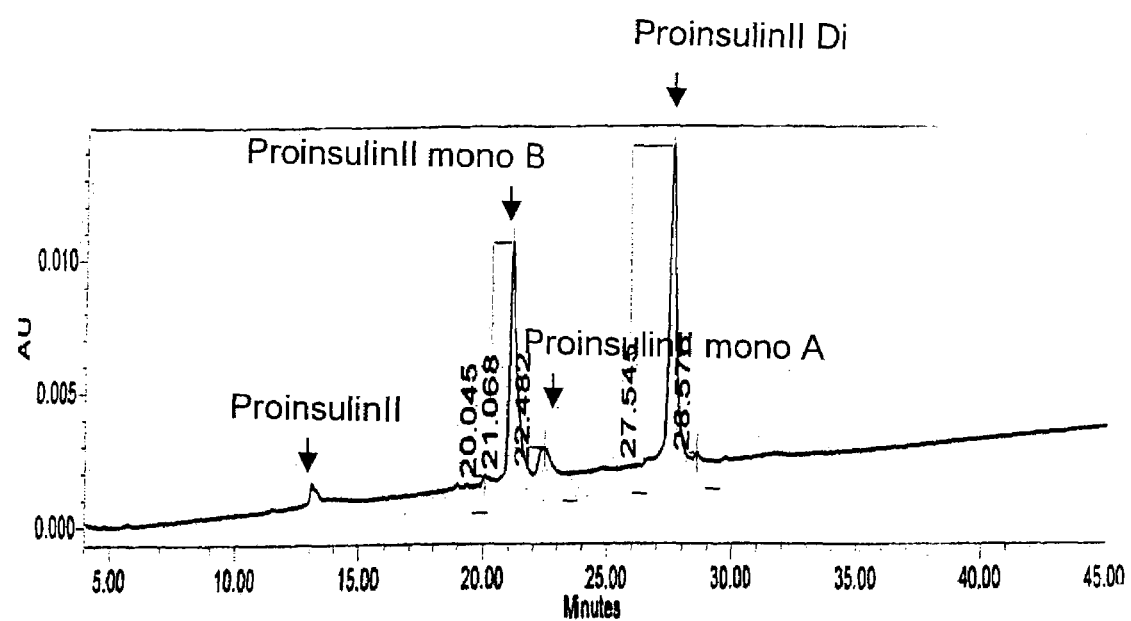
FIG. 24 illustrates a HPLC chromatogram of the conjugation reaction of activated hexadecylPEG6 with proinsulin-II.

Methods of Synthesizing Acylated Insulin Polypeptides using Proinsulin Preparation of other $Lys_{B29}$-Oligomer-Conjugated Insulin (a) Conjugation of Recombinant Proinsulin II. Recombinant Proinsulin II (MW 11134 Daltons) was obtained. A ($1.79 \times 10^{-3}$ mmol) portion of proinsulin II was dissolved in 1 mL of DMSO and added to triethylamine 0.25 mL, and the solution was stirred for 20 minutes. To the resulting solution was added a solution of activated hexaethyleneglycol monohexadecylether (hexadecyl-PEG6 oligomer, FIG. 20) ($4.49 \times 10^{-3}$ mmol) in 1 mL THF. The course of the conjugation (acylation) reaction was monitored by HPLC. When the reaction appeared to be complete, it was quenched with 1% TFA solution. The reaction mixture was then processed and exchanged into 100 mM Tris-HCl Buffer, pH 7.6.

A small portion of the reaction mixture before exchanging with 100 mM Tris-HCl Buffer, pH 7.6 was processed and analyzed by HPLC. The major products were purified by HPLC and analyzed by mass spectroscopy. Two monoconjugates and one diconjugate of Proinsulin II were thus obtained. The HPLC retention time relative to that of reference standards and mass spectral analysis were used to determine the identity and purity of each product (Table 13).

TABLE 13

Oligomer-conjugates of Proinsulin II

| Conjugate | Product | MW | Figure |
|---|---|---|---|
| Proinsulin II Mono B | ($Lys_{B29}$-hexadecyl-PEG6-oligomer-conjugated ProinsulinII) | 11666 | 21 |
| Proinsulin II Mono A | (leaderpeptide-hexadecyl-PEG6-oligomer-conjugated ProinsulinII) | 11666 | 22 |
| Proinsulin II Di | ($Lys_{B29}$-hexadecyl-oligomer-conjugated ProinsulinII and leaderpeptide-hexadecyl-PEG6-oligomer-conjugated ProinsulinII) | 12198 | 23 |

Figure 25:
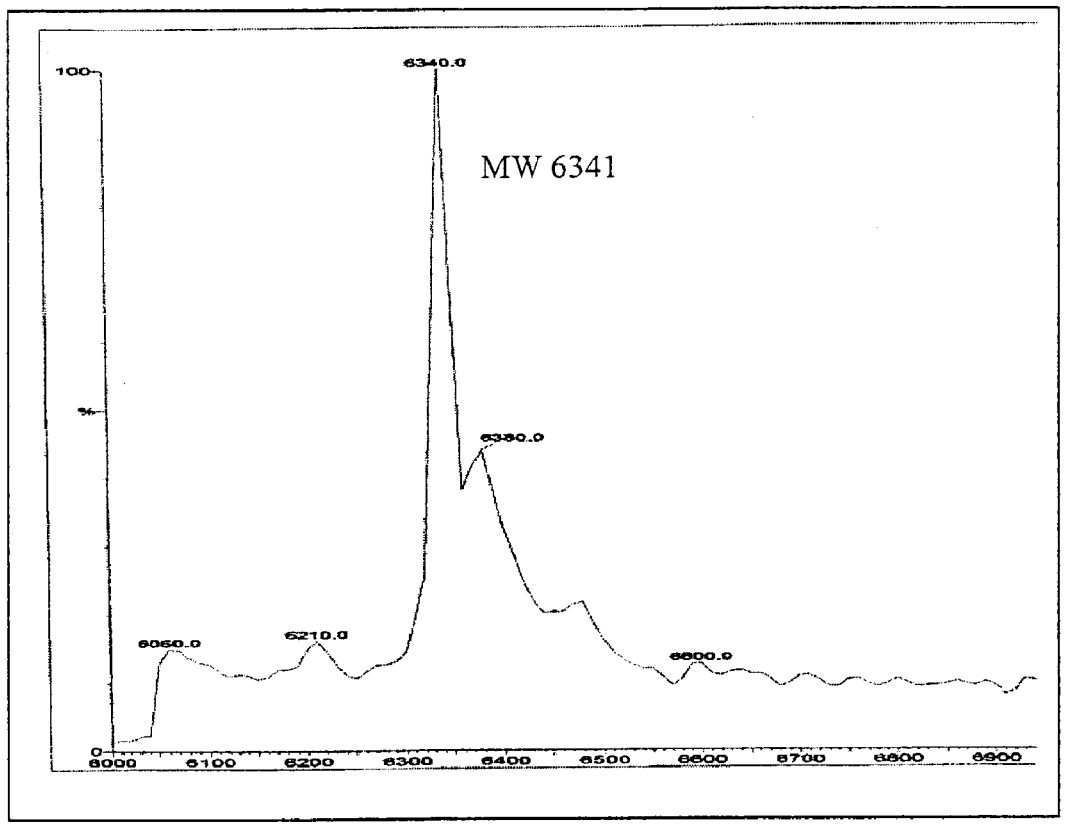
FIG. 25 illustrates an Es-mass spectrum for LysB29-hexadecyl-PEG6-oligomer-conjugated insulin.
Figure 26:
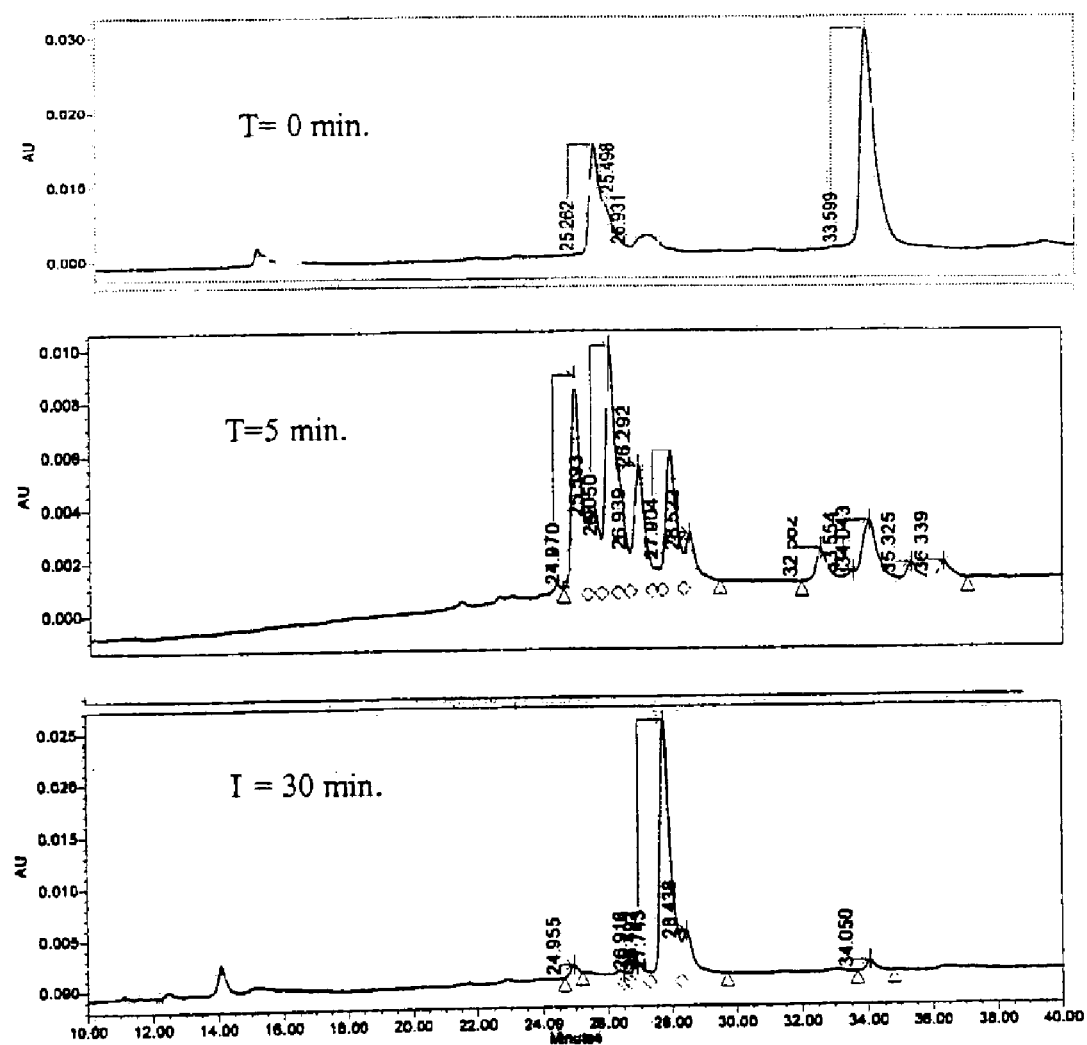
FIG. 26 illustrates a HPLC chromatogram of an enzyme cocktail reaction of a hexadecyl-PEG6 conjugated mixture of proinsulin-II.

(b) Enzyme Cocktail Cleavage of HexadecylPEG6 Oligomer-Conjugated Recombinant Proinsulin I. An aliquot of the Tris-HCl solution of the product mixture from was analyzed by HPLC to determine the polypeptide concentration. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.05 μmol/mL) was then allowed to react with trypsin ($1.56 \times 10^{-4}$ μmol/mL) and carboxypeptidase B ($0.78 \times 10^{-4}$ μmol/mL). After 30 minutes, the reaction was quenched by the addition of 9 mL of 0.1% trifluoroacetic acid in acetonitrile. The major products were identified by HPLC retention time and mass spectral analysis (FIGS. 25 and 26). Insulin and $Lys_{B29}$-Hexadecyl-PEG6-Oligomer-Conjugated Insulin were obtained. The product mixture from the reaction was processed and analyzed by HPLC. The HPLC retention time relative to that of reference standards and mass spectral analysis were used to determine the identity and purity of each product (Table 14).

TABLE 14

Oligomer-conjugates of Proinsulin II and Products or (Expected Products) from Enzyme Cocktail Cleavage

| Conjugate | Products | MW | Figure |
|---|---|---|---|
| Proinsulin II Mono A | Insulin hexadecyl-PEG6-oligomer-conjugated-leader peptide, (desThr insulin) and (Artificial C-peptide) | 5809 (M + 1) 2035 (M + 1) | — — |
| Proinsulin II Mono B | $Lys_{B29}$-hexadecyl-PEG6-oligomer-conjugated Insulin and (Leader peptide) | 6341 (M + 1) | 24 |
| Proinsulin II Di | LysB29-Hexadecyl-PEG6-Oligomer-Conjugated Insulin, (hexadecyl-PEG6-oligomer-conjugated-leader peptide) and (Artificial C-peptide) | 6341 (M + 1) | 24 |

Figure 27:
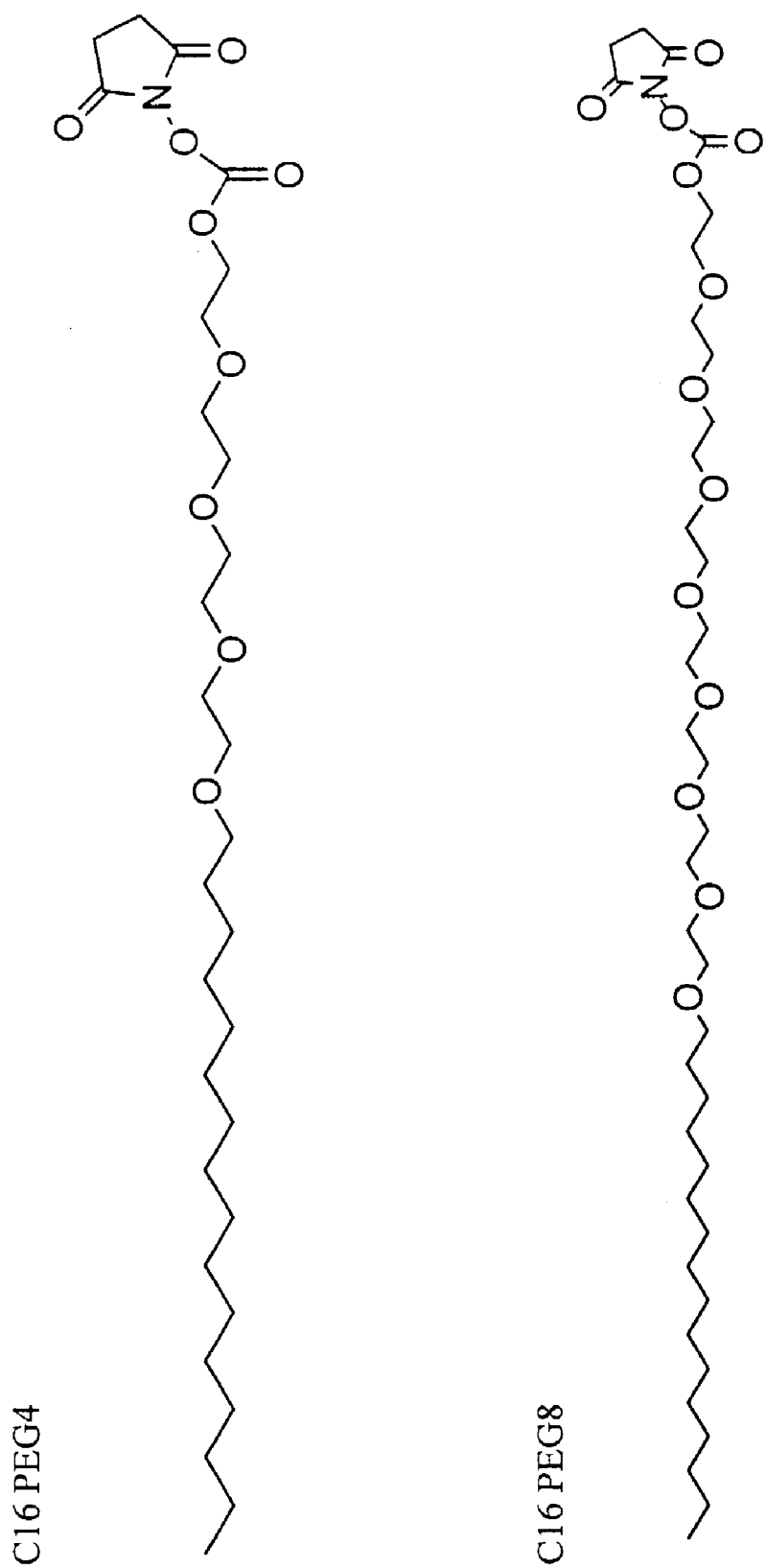
FIG. 27 illustrates structures of activated octaethylene glycol monohexadecylether (C16-PEG8) and activated tetraethylene glycol monohexadecylether (C16-PEG4)

Activated tetraethylene glycol monohexadecylether (C16-PEG4) (FIG. 27) and activated octaethylene glycol monohexadecylether (C16-PEG8) (FIG. 27) were conjugated with proinsulin II using this procedure and subjected to the enzyme cocktail described herein to get the final products $Ly_{SB29}$-Hexadecyl-PEG4-Oligomer-Conjugated Insulin and $Ly_{SB29}$-Hexadecyl-PEG8-Oligomer-Conjugated Insulin, respectively.

Example 37

Preparation of $LysB_{29}$-Acylated Insulin (a) Acylation of Recombinant Proinsulin I. Recombinant Proinsulin I (MW 10,642 Daltons) is obtained. A ($1.79 \times 10^{-3}$ mmol) portion of proinsulin I is dissolved in 1 mL of DMSO and added to triethylamine 0.25 mL, and the solution is stirred for 20 minutes. To the resulting solution is added a solution of N-hydroxysuccinimide ester of Palmitic acid ($CH_3 (CH_2)_{14}CO_2H$) ($9.30 \times 10^{-3}$ mmol) in 1 mL THF. The course of the conjugation (acylation) reaction is monitored by HPLC. When the reaction appears to be complete, it is quenched with 1% TFA solution. The reaction mixture is then processed and exchanged into 100 mM Tris-HCl Buffer, pH 7.6.

A small portion of the reaction mixture before exchanging with 100 mM Tris-HCl Buffer, pH 7.6 is processed and analyzed by HPLC. The major products are purified by HPLC and analyzed by mass spectroscopy. Two monoacylated, one diacylated and one tri acylated products of Proinsulin I are thus obtained. The HPLC retention time relative to that of reference standards and mass spectral analysis are used to determine the identity and purity of each product (Table 15).

TABLE 15

Oligomer-conjugates of Proinsulin I with Activated Palmitoyl

| Conjugate | (Product) | Expected MW |
|---|---|---|
| Proinsulin I Mono B | ($Lys_{B29}$-Palmitoyl ProinsulinI) | 6046 |
| Proinsulin I Mono A | (Lys64-Palmitoyl ProinsulinI) | 6046 |
| Proinsulin I Di | ($Lys_{B29}$, Lys 64 Di (Palmitoyl) ProinsulinI) | 6284 |
| Proinsulin I, Tri | ($Lys_{B29}$, Lys 64 and N-amino Leader peptide Tri (Palmitoyl) ProinsulinI) | 6522 |

(b) Enzyme Cocktail Cleavage of Palmitoyl Recombinant Proinsulin I. An aliquot of the Tris-HCl solution of the product mixture is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture (0.05 μmol/mL) is then allowed to react with trypsin ($1.56 \times 10^{-4}$ μmol/mL) and carboxypeptidase B ($0.78 \times 10^{-4}$ μmol/mL). After 30 minutes, the reaction is quenched by the addition of 9 mL of 0.1% trifluoroacetic acid in acetonitrile. The major products are identified by HPLC retention time and mass spectral analysis. Insulin, $Lys_{B29}$-Palmitoyl Insulin and Lys64-Palmitoyl C-peptide are obtained. The product mixture from the reaction is processed and analyzed by HPLC. The HPLC retention time relative to that of reference standards and mass spectral analysis are used to determine the identity and purity of each product.

Activated esters of Acyl chain (C2 to C18) are reacted with proinsulin I using the procedure in example 37(a) and subjected to the enzyme cocktail as in example 37(b) to get the final products Lys B29 Acylated Insulins and Lys64 acylated C-peptides corresponding to the acyl chain.

Example 38

Preparation of Insulin from Carbonylated Proinsulin (a) Carbonylation of Recombinant Proinsulin I. Recombinant Proinsulin I (MW 10,642 Daltons) is obtained. A ($1.79 \times 10^{-3}$ mmol) portion of proinsulin I is dissolved in 1 mL of DMSO and added to triethylamine 0.25 mL, and the solution is stirred for 20 minutes. To the resulting solution is added to a solution of Aryl carbonate ester ($9.30 \times 10^{-3}$ mmol) (N-hydroxysuccinimide carbonate ester of phenol) in 1 mL THF. The course of the conjugation (carbonylation) reaction is monitored by HPLC. When the reaction appears to be complete, it is quenched with 1% TFA solution. The reaction mixture is then processed to remove solvents, N-hydroxy succinimide and phenol, and exchanged into 100 mM Tris-HCl Buffer, pH 7.6.

A small portion of the reaction mixture before exchanging with 100 mM Tris-HCl Buffer, pH 7.6 is processed and analyzed by HPLC. The major products are purified by HPLC and analyzed by mass spectroscopy. Two monocarbonylated products, one dicarbonylated product and one tricarbonylated product of Proinsulin I are thus obtained. The HPLC retention time relative to that of reference standards and mass spectral analysis are used to determine the identity and purity of each product (Table 16).

TABLE 16

Oligomer-conjugates of Proinsulin I with Activated carbonate ester of phenol

| Conjugate | (Product) |
|---|---|
| Proinsulin I Mono B | ($Lys_{B29}$-carbonylated ProinsulinI) |
| Proinsulin I Mono A | (Lys64-carbonylated ProinsulinI) |
| Proinsulin I Di | ($Lys_{B29}$, Lys 64 Di (carbonylated) ProinsulinI) |
| Proinsulin I, Tri | ($Lys_{B29}$, Lys 64 and N-amino Leader peptide Tri (carbonylated) ProinsulinI) |

(b) Enzyme Cocktail Cleavage of Carbonylated Recombinant Proinsulin I. An aliquot of the Tris-HCl solution of the product mixture is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture (0.05 μmol/mL) is then allowed to react with trypsin ($1.56 \times 10^{-4}$ μmol/mL) and carboxypeptidase B ($0.78 \times 10^{-4}$ μmol/mL). After 30 minutes, the reaction is quenched by the addition of 9 mL of 0.1% trifluoroacetic acid in acetonitrile. The reaction mixture is then processed and exchanged into 10 mM Phosphate Buffer, pH 7.2.

A small portion of the reaction mixture before exchanging with 10 mM Phosphate Buffer, pH 7.2 is processed and analyzed by HPLC. The major products are purified by HPLC and analyzed by mass spectroscopy. The major products are identified by HPLC retention time and mass spectral analysis. Insulin, $Lys_{B29}$-Phenyl carbamate of Insulin and Lys64-Phenyl carbamate of C-peptide are obtained. The product mixture from the reaction is processed and analyzed by HPLC. The HPLC retention time relative to that of reference standards and mass spectral analysis are used to determine the identity and purity of each product.

(c) Pancreatic Elastase Enzyme Cleavage of Carbonylated Insulin. An aliquot of the 0.01M phosphate buffer solution of the product mixture is analyzed by HPLC to determine the polypeptide concentration. A solution of Pancreatic Elastase (Type III; from porcine pancreas) is prepared in 10 mM phosphate Buffer, pH 7.2. The product mixture ($5 \times 10^{-3}$M) is then allowed to react with pancreatic elastase ($2.56 \times 10^{-4}$M) at room temperature. After 60 minutes, the reaction is quenched by the addition of an equal volume of 0.02M citric acid.

The major products are identified by HPLC retention time and mass spectral analysis. Insulin and Lys64-C-peptide are obtained. The product mixture from the reaction is processed and analyzed by HPLC. The HPLC retention time relative to that of reference standards and mass spectral analysis are used to determine the identity and purity of each product.

Example 39

Enzyme Transformation Process Optimization

In one embodiment of the present invention, the concentration of enzyme needed to cleave peptides from a proinsulin polypeptide molecule to produce insulin can be reduced by up to 4000×, while maintaining effective and specific cleavage activity. A Trypsin-CPB cocktail is employed, according to the protocols described herein for cleavage of polypeptides to produce insulin, wherein the trypsin enzyme is present in an amount that is >700 moles of trypsin for each mole of proinsulin, and can be present, for example, in the following ratio: 1 mole proinsulin: 1/2000 mole trypsin. The carboxypeptidase B (CPB) can be present in the cocktail in an amount that is >2000–2200 moles CPB as compared to proinsulin and can be present for example in the following ratio: 1 mole proinsulin: 1/4000 mole CPB. Thus, the enzyme cocktail of trypsin and CPB can be employed as follows: 1 mole substrate: 1/>700 mole trypsin: 1/>2000–2200 mole CPB and can be, for example, 1 mole substrate: 1/2000 mole trypsin: 1/4000 mole CPB. The ratio of substrate, such as proinsulin, to trypsin and CPB can be any value above or below the values described herein, and can be, for example, 1 mole substrate: 1/750 moles trypsin, 1 mole substrate: 1/800 moles trypsin, 1 mole substrate/850 moles trypsin 1 mole substrate/900 moles trypsin, 1 mole substrate:1/950 moles trypsin, 1 mole substrate:1/1000 moles trypsin, 1 mole substrate:1/1200 moles trypsin, 1 mole substrate:1/1400 moles trypsin, 1 mole substrate:1/1500 moles trypsin, 1 mole substrate:1/1600 moles trypsin, 1 mole substrate:1/1700 moles trypsin, 1 mole substrate:1/1800 moles trypsin, 1 mole substrate:1/1900 moles trypsin, 1 mole substrate:1/2000 moles trypsin, 1 mole substrate:1/2200 moles trypsin, 1 mole substrate:1/2400 moles trypsin, 1 mole substrate:1/2500 moles trypsin, 1 mole substrate:1/2600 moles trypsin, 1 mole substrate:1/2800 moles trypsin, 1 mole substrate:1/3000 moles trypsin, 1 mole substrate:1/2100 moles CPB, 1 mole substrate:1/2200 moles CPB, 1 mole substrate:1/2400 moles CPB, 1 mole substrate:1/2500 moles CPB, 1 mole substrate:1/2600 moles CPB, 1 mole substrate:1/2800 moles CPB, 1 mole substrate:1/3000 moles CPB, 1 mole substrate:1/3200 moles CPB, 1 mole substrate:1/3400 moles CPB, 1 mole substrate: 1/3600 moles CPB, 1 mole substrate:1/3800 moles CPB, 1 mole substrate:1/4000 moles CPB, 1 mole substrate:1/4200 moles CPB, 1 mole substrate:1/4400 moles CPB, 1 mole substrate:1/4600 moles CPB, 1 mole substrate:1/4800 moles CPB, 1 mole substrate:1/5000 moles CPB, etc., and/or any combination thereof with respect to a ratio of substrate, trypsin and CPB.

Thus, the present invention also provides a method of producing insulin from a proinsulin polypeptide, comprising contacting the proinsulin polypeptide with an enzymatic cocktail to cleave C-peptide and leader peptide from the proinsulin polypeptide, wherein the enzymatic cocktail comprises a trypsin-like enzyme (e.g., trypsin, thrombin, enzymes from *Achrombacter lyticus*) and a carboxypeptidase-like enzyme (e.g., carboxypeptidase A, carboxypeptidase B), under conditions wherein c) the molar ratio of the trypsin-like enzyme to the carboxypeptidase-like enzyme is 1/>700:1/>2000.

In some embodiments of the present invention, when the substrate is a proinsulin polypeptide, the ratio of trypsin enzyme to CPB enzyme is a ratio of enzymes at which cleavage of the proinsulin polypeptide occurs at Arg31 and at Arg residues connecting the B-chain to the leader peptide and connecting the B-chain to the C-peptide and connecting the A-chain to the C-peptide but does not occur to a significant degree (e.g., is less than 1%, 5% or 10%) at Arg B22 of the proinsulin polypeptide.

Example 40

Figure 33:
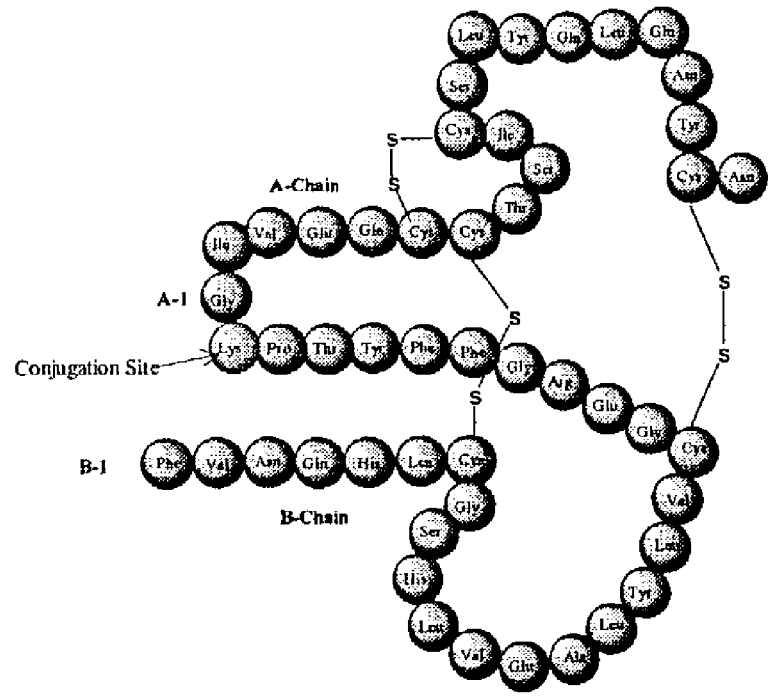
FIG. 33 illustrates conjugation to DesThr single chain precursor.

Use of Single Chain Insulin Precursors to Make Insulin Derivative Without Transpeptidation Process Conjugation (acylation) of insulin at the B-29 Lys amino residue of the B-chain is made by reacting the native insulin with an activated entity (e.g., N-hydroxysuccinimide ester of Oligomer) (FIG. 33) under a selected reaction medium. The selectivity of the reaction towards B-29 Lys is reduced mainly due to acylation at A-1 Gly as well as B-1 Phe amino groups towards the N-hydroxysuccinimide ester. Under these conditions, the reaction leads to a mixture of insulin conjugates composed of modifications at B-29 Lys as well as A-1 Gly and B-Phe. Subsequently, the B-29 Lys conjugate is purified from other products by chromatography at a low yield. It has been shown that use of optimized conditions involving an organic medium and an organic base and a stoichiometric amount of N-hydroxysuccinimide improved the acylation selectivity at B-29 Lys over A-1 Gly. However, the problem of modifications at other sites cannot be avoided with the use of unprotected insulin.

Figure 34:
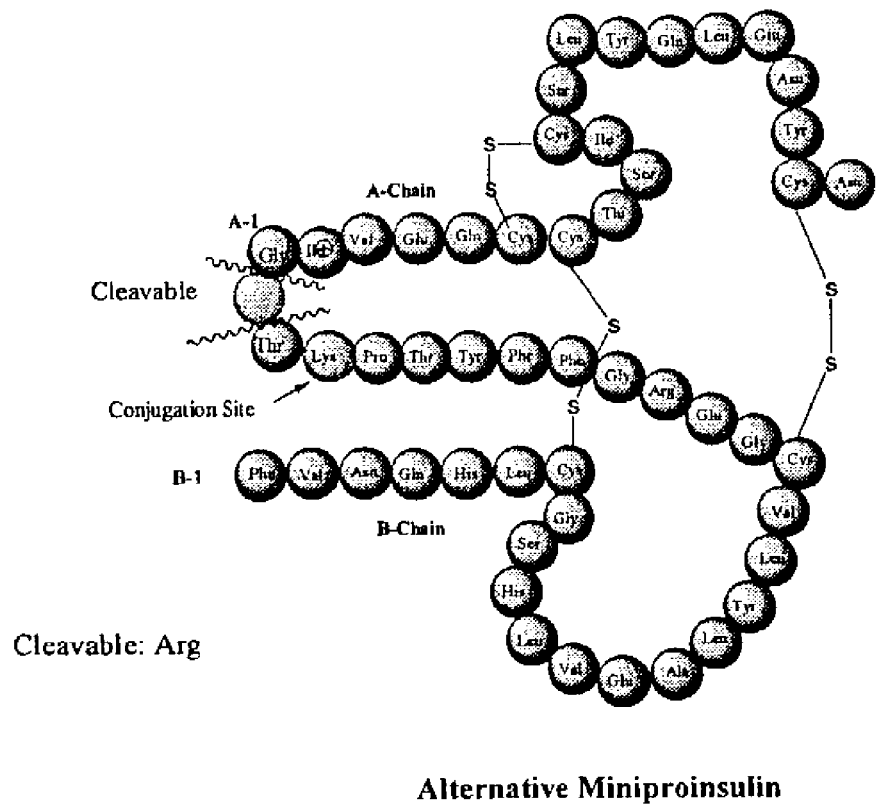
FIG. 34 illustrates non-transpeptidation construct 1 of a single chain insulin precursor.
Figure 35:
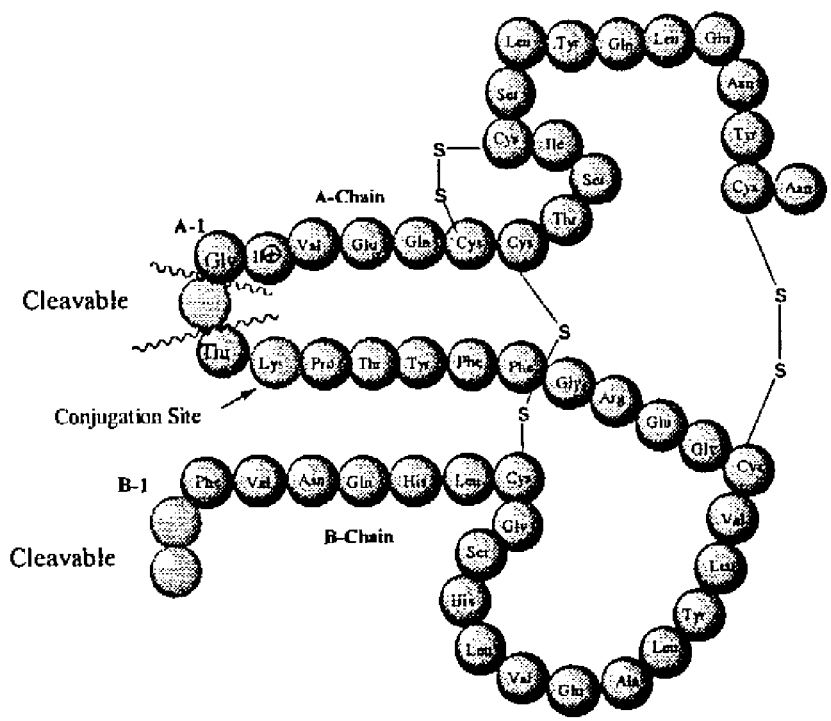
FIG. 35 illustrates a non-transpeptidation construct of a single chain insulin precursor with a leader peptide.

It has been shown in the present invention that use of natural and artificial proinsulins (FIGS. 34 and 35) provide a unique pathway to make insulin derivatives modified or conjugated at the Lys side chain of the B-chain with a selectivity greater than with the insulin pathway. In proinsulin(s), the amino terminus of the A-chain of insulin, A-1 Gly, is connected to the carboxy terminus of B-chain via a C-peptide. Since the A-1 Gly amino side chain is protected by the C-peptide, the reaction (acylation) of proinsulin with N-hydroxysuccinimide ester would selectively modify the Lys amino side chain (e.g., B-29, human insulin) of the B-chain. Upon enzyme cleavage with trypsin and carboxy peptidase, the conjugate would provide B-29 Lys acylated insulin. The proinsulin would be used as the starting material instead of insulin because even if the Lys (e.g., Lys 62 of natural proinsulin) on the C-peptide is acylated along with B-29 Lys, enzymatic cleavage with trypsin and carboxy peptidase of the N-terminus of the leader peptide, will still occur at Arg 63, Arg 32 and Arg 31 to provide the B chain Lys acylated insulin.

The new sequences can also be expressed from yeast systems (e.g., *Pichia, P. morpha*, etc.) as the result of the short C-peptide (C=0, −1, −2, −3, −4, −5, etc.).

Figure 36:
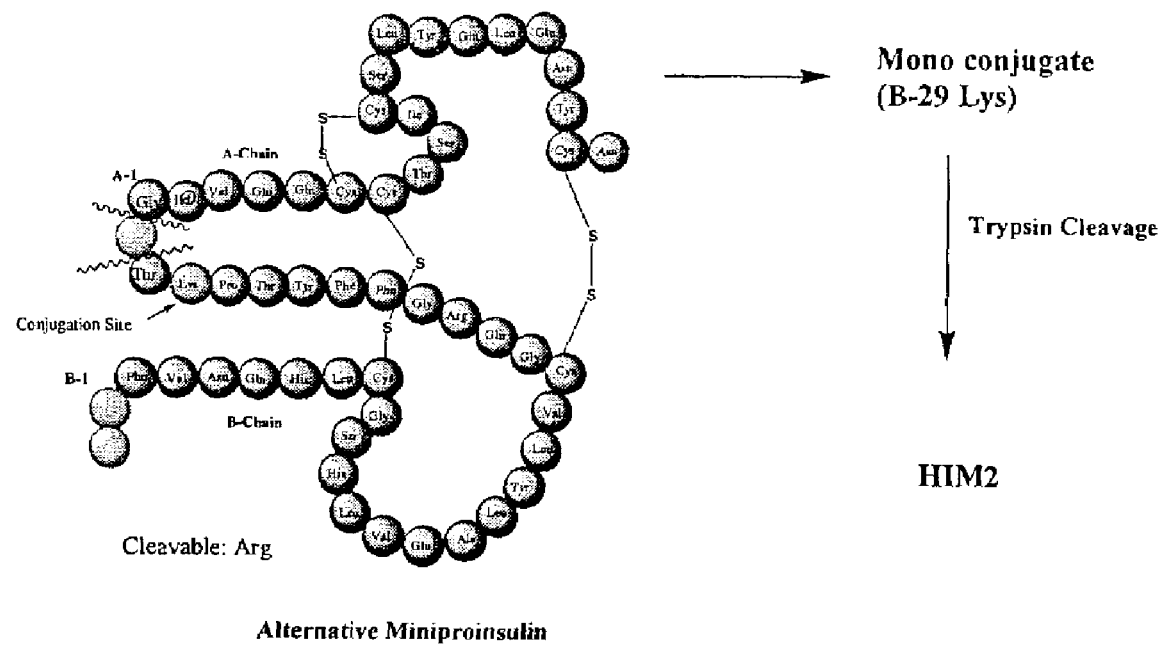
FIG. 36 illustrates a direct pathway to B-29 Lys modified insulin conjugate from single chain insulin precursor-3 without transpeptidation.
Figure 37:
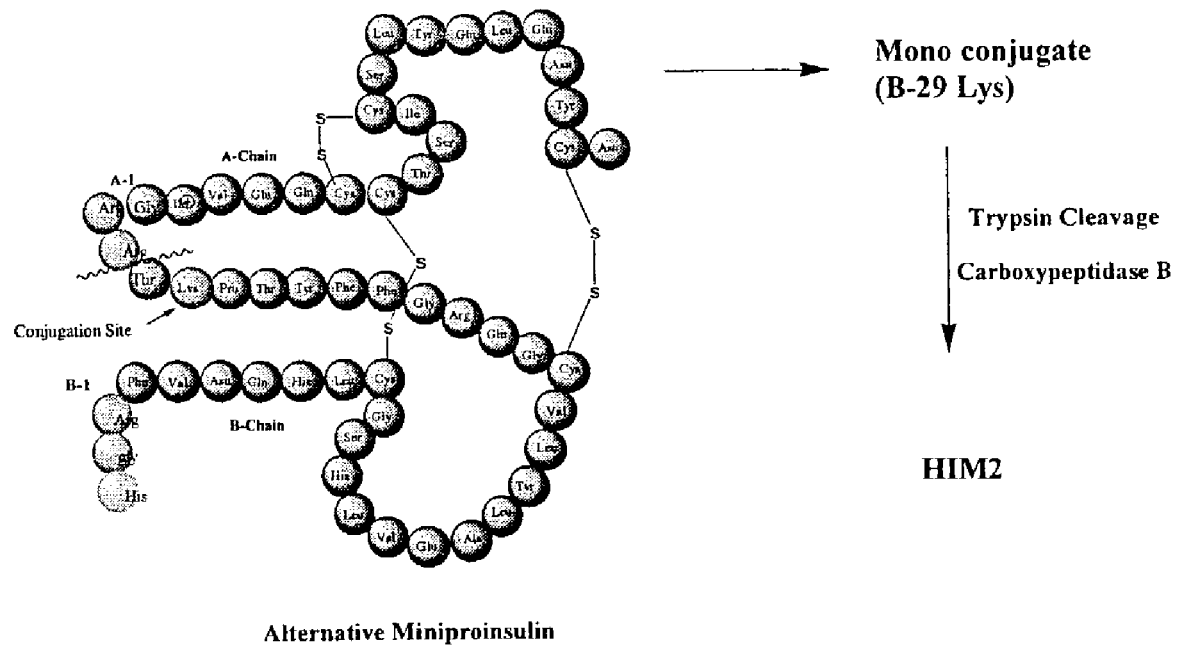
FIG. 37 illustrates a direct pathway to B-29 Lys modified insulin conjugate from a single chain insulin precursor with transpeptidation via an enzyme cocktail.

The advantages of the use of these new sequences as the starting material to provide Lys modified insulin (FIGS. 36 and 37) are as follows.

1. Since A-1 Gly amino terminus is protected from acylation, the use of proinsulin provides high selectivity for B-29 Lys modification.
2. B-1 Phe sites can also be blocked from conjugation in the presence of a leader sequence at B-1.
3. Conjugation at B-29 Lys prevents the removal of the B-30 Thr by trypsin and therefore no transpeptidation process would be needed to introduce Thr at B-30.
4. Both conjugates, mono B-29 Lys conjugate and di conjugate, B29 and L-1 (leader peptide-1), yield a single product, B-29 modified insulin upon cleavage.
5. The diconjugate, conjugated at B-29 Lys and B-1 Phe with the use of single chain insulin precursor without leader peptide, yields a single product, B-29 and B-1 modified insulin upon cleavage.
6. This pathway provides high conversion to B-29 product (>80%) compared to that obtained via conjugation using insulin.
7. This pathway can be used with any type of proinsulin regardless of the sequence of the noncleavable part of the spacer (mini C-peptide) between A and B chain or leader peptide.
8. This pathway can be utilized to produce modification at the Lys side chain regardless of the position of Lys on the B-chain. Therefore, it can be used with any type of pre-proinsulin (proinsulin with leader peptide or fusion protein) or mini proinsulin (proinsulin with small C-peptide chains) or proinsulin like molecule (e.g., pro LysPro).
9. This pathway provides a direct pathway to B-29Lys, B-1 Phe di-acylated (modified) insulin using a single chain insulin precursor without a leader peptide (e.g., construct 1).
10. This pathway provides a commercially cheaper and high yielding manufacturing scheme to produce B-29 Lys modified insulin (e.g., HIM2) over the use of insulin or non-Thr containing single chain insulin precursors.

Sequences of non-transpeptidation insulin single chain precursors:

Construct 1: B-chain-Arg-A-chain
Construct 2: His-Gly-Arg-B-chain-Arg-A-chain
Construct 3: His-Gly-Arg-B-chain-Arg-Arg-A-chain
Construct 3: Leader peptide-Arg-B-chain-Arg-Ala-Lys-Arg-A-chain
Construct 4: Leader peptide-Arg-B-chain-Arg-Pro-Arg-A-chain
Construct 5: B-chain-Arg-Arg-A-chain B-chain and A-chain: B- and A-chains of human and other (e.g., bovine, porcine, murine, etc.) insulin sequences, or modifications of any insulin sequence (e.g., Lys28Pro29 insulin) or insulin analogs without one (e.g., desThr B-chain) or more amino acids or replacement of one or more amino acids.

The present invention has been described herein with reference to various embodiments. These embodiments do not serve to limit the invention, but are set forth for illustrative purposes. The scope of the invention is defined by the claims that follow.

That which is claimed is:

1. A method of synthesizing an insulin polypeptide-oligomer conjugate comprising:
   (a) contacting a proinsulin polypeptide with an oligomer comprising a hydrophilic moiety and/or a lipophilic moiety under conditions sufficient to couple the oligomer to the proinsulin polypeptide and provide a proinsulin polypeptide-oligomer conjugate, wherein the proinsulin polypeptide comprises:
      (i) an insulin polypeptide; and
      (ii) one or more non-insulin polypeptides coupled to the insulin polypeptide by peptide bond(s) capable of being cleaved to yield the insulin polypeptide; and
   (b) cleaving the one or more non-insulin polypeptides from the proinsulin polypeptide-oligomer conjugate to provide the insulin polypeptide-oligomer conjugate.

2. The method of claim 1 wherein:
   (a) the proinsulin polypeptide comprises multiple conjugation sites; and
   (b) step (a) yields a proinsulin polypeptide-oligomer comprising multiple oligomers.

3. The method of claim 1 wherein:
   (a) the proinsulin polypeptide comprises one or more conjugation sites on the insulin polypeptide portion thereof, and
   (b) step (a) yields a proinsulin polypeptide-oligomer comprising one or more oligomers on the insulin polypeptide portion thereof.

4. The method of claim 3 wherein step (a) yields a proinsulin polypeptide-oligomer conjugate wherein the non-insulin polypeptide(s) are unconjugated.

5. The method of claim 1 wherein:
(a) the proinsulin polypeptide comprises:
  (i) at least one conjugation site on the insulin polypeptide portion thereof; and
  (ii) at least one conjugation site on one or more non-insulin polypeptide portions thereof; and
(b) step (a) yields a proinsulin polypeptide-oligomer comprising:
  (i) at least one oligomer coupled to the insulin polypeptide portion thereof; and
  (ii) at least one oligomer coupled to one or more of the non-insulin polypeptide portion(s) thereof.

6. The method of claim 1, wherein step (a) comprises:
(a) contacting the oligomer with an activating agent under conditions sufficient to provide an activated oligomer capable of coupling to a nucleophilic functionality on the proinsulin polypeptide; and
(b) contacting the activated oligomer with the proinsulin polypeptide under conditions sufficient to provide the proinsulin polypeptide-oligomer conjugate.

7. The method of claim 6, wherein step 0 is performed in situ.

8. The method of claim 6, wherein the molar ratio of activated oligomer to proinsulin polypeptide in step (b) is greater than about 1:1.

9. The method of claim 6, wherein the molar ratio of activated oligomer to proinsulin polypeptide in step (b) is greater than about 3:1.

10. The method of claim 6, wherein the molar ratio of activated oligomer to proinsulin polypeptide in step (b) is greater than about 4:1.

11. The method of claim 1, wherein the oligomer comprises a polyethylene glycol moiety.

12. The method of claim 1, wherein the oligomer consists essentially of a polyethylene glycol moiety.

13. The method of claim 1, wherein:
(a) the insulin polypeptide comprises an A-chain polypeptide and a B-chain polypeptide, and
(b) the one or more non-insulin polypeptides comprise a connecting peptide coupled at a first end to the C-terminus of the B-chain polypeptide and coupled at a second end to the N-terminus of the A-chain polypeptide.

14. The method of claim 13 wherein:
(a) the B-chain comprises a conjugation site at B29, and
(b) the insulin polypeptide-oligomer conjugate is conjugated at the B29 conjugation site.

15. The method of claim 13 wherein:
(a) the proinsulin polypeptide has a single lysine at B29, and (b) the insulin polypeptide-oligomer conjugate is a B29 monoconjugate.

16. The method of claim 1, wherein the connecting peptide is a C-peptide polypeptide.

17. The method of claim 16 wherein:
(a) the G-peptide comprises a lysine, and
(b) step (a) yields a proinsulin polypeptide-oligomer in which the lysine(s) of the C-peptide are coupled to oligomer(s).

18. The method of claim 1, wherein the connecting peptide is C-peptide.

19. The method of claim 1, wherein the connecting peptide is devoid of lysine residues.

20. The method of claim 1, wherein the proinsulin polypeptide further comprises a leader peptide coupled to the N-terminus of the B-chain polypeptide.

21. The method of claim 1 wherein:
(a) the leader peptide comprises a lysine, and
(b) step (a) yields a proinsulin polypeptide-oligomer in which the lysine(s) of the leader peptide are coupled to oligomer(s).

22. The method of claim 1, wherein the leader peptide is devoid of lysine residues.

23. The method of claim 1 wherein step (a) yields a proinsulin polypeptide-oligomer comprising an oligomer coupled at an N-terminus of the leader peptide.

24. The method of claim 1, wherein the one or more non-insulin polypeptides further comprise a leader peptide coupled to the N-terminus of the B-chain polypeptide.

25. The method of claim 24 wherein:
(a) the leader peptide comprises a lysine, and
(b) step (a) yields a proinsulin polypeptide-oligomer in which the lysine(s) of the C-peptide are coupled to oligomer(s).

26. The method of claim 24, wherein the leader peptide is devoid of lysine residues.

27. The method of claim 1, wherein:
(a) the insulin polypeptide comprises an A-chain polypeptide and a B-chain polypeptide, and
(b) the C-terminus of the B-chain polypeptide is coupled to the N-terminus of the A-chain polypeptide.

28. The method of claim 1, wherein the proinsulin polypeptide is proinsulin.

29. The method of claim 1, wherein the proinsulin polypeptide is proinsulin coupled at the N-terminus of the B-chain to a leader peptide by a cleavable peptide bond.

30. The method of claim 1, wherein the insulin polypeptide is insulin.

31. The method of claim 30, wherein the oligomer is coupled to the lysine at the B29 position of the insulin.

32. The method of claim 1, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $ProB^{29}$ insulin, human; $Leu^{B28}$ $Pro_{B29}$ insulin, human; $Val^{B28}$ $Pro^{B29}$ insulin, human; and $Ala^{B28}$ $Pro^{B29}$ insulin, human.

33. The method of claim 1, wherein the oligomer is present as a substantially monodispersed mixture.

34. The method of claim 1, wherein the oligomer is present as a monodispersed mixture.

35. The method of claim 1, wherein the hydrophilic moiety is a polyalkylene glycol moiety.

36. The method of claim 35, wherein the polyalkylene glycol moiety is a polyethylene glycol moiety.

37. The method of claim 35, wherein the polyalkylene glycol moiety has between 1 and 50 polyalkylene glycol subunits.

38. The method of claim 35, wherein the polyalkylene glycol moiety has between 3 and 50 polyalkylene glycol subunits.

39. The method of claim 35, wherein the polyalkylene glycol moiety has between 2 and 10 polyalkylene glycol subunits.

40. The method of claim 35, wherein the polyalkylene glycol moiety has between 4 and 10 polyalkylene glycol subunits.

41. The method of claim 35, wherein the polyalkylene glycol moiety has at least 2 polyalkylene glycol subunits.

42. The method of claim 1, wherein the lipophilic moiety is an alkyl or fatty acid moiety.

43. The method of claim 1, wherein the lipophilic moiety has between 1 and 28 carbon atoms.

44. The method of claim 1, wherein the lipophilic moiety has between 2 and 24 carbon atoms.

45. The method of claim 1, wherein the lipophilic moiety has between 3 and 18 carbon atoms.

46. The method of claim 1, wherein the lipophilic moiety has between 4 and 12 carbon atoms.

47. The method of claim 1, wherein the lipophilic moiety has between 5 and 7 carbon atoms.

48. The method of claim 1, wherein the lipophilic moiety has between 4 and 14 carbon atoms.

49. The method of claim 1, wherein the cleaving of the one or more non-insulin polypeptides from the proinsulin polypeptide-oligomer conjugate comprises contacting the proinsulin polypeptide-oligomer conjugate with one or more enzymes that are capable of cleaving the bond(s) between the one or more non-insulin polypeptides and the insulin polypeptide under conditions sufficient to cleave the one or more non-insulin polypeptides from the proinsulin polypeptide-oligomer conjugate.

50. The method of claim 49, wherein the one or more enzymes are selected from the group consisting of trypsin, carboxy peptidase B, and mixtures thereof.

51. The method of claim 1, wherein the connecting peptide has a terminal amino acid residue at the first end, and wherein the cleaving of the connecting peptide from the proinsulin polypeptide-oligomer conjugate comprises:
(a) contacting the proinsulin polypeptide-oligomer conjugate with a first enzyme under conditions sufficient to provide a terminal amino acid residue-insulin polypeptide-oligomer conjugate; and
(b) contacting the terminal amino acid residue-insulin polypeptide-oligomer conjugate with a second enzyme under conditions sufficient to provide the insulin polypeptide-oligomer conjugate.

52. The method of claim 51, wherein the terminal amino acid residue is an arginine residue.

53. The method of claim 52, wherein the insulin polypeptide is insulin, and wherein the connecting peptide is human C-peptide.

54. The method of claim 51, wherein the contacting of the proinsulin polypeptide-oligomer conjugate with a first enzyme and the contacting of the terminal amino acid residue-insulin polypeptide-oligomer conjugate with a second enzyme occur substantially concurrently.

55. The method of claim 54, wherein the first enzyme and the second enzyme are provided in a mixture comprising the first enzyme and the second enzyme.

56. The method of claim 51, wherein the first enzyme is trypsin, and wherein the second enzyme is carboxy peptidase B.

57. The method of claim 1, further comprising chemically modifying one or more of the oligomer(s) of the insulin polypeptide-oligomer conjugate.

58. The method of claim 1, further comprising activating one or more of the oligomer(s) of the insulin polypeptide-oligomer conjugate.

59. The method of claim 1, further comprising lengthening one or more of the oligomer(s) of the insulin polypeptide-oligomer conjugate.

60. The method of claim 1, further comprising shortening one or more of the oligomer(s) of the insulin polypeptide-oligomer conjugate.

61. The method of claim 1, wherein the yield of insulin polypeptide-oligomer conjugate is greater than 75 percent.

62. The method of claim 1, wherein the yield of insulin polypeptide-oligomer conjugate is greater than 85 percent.

63. The method of claim 1, wherein the yield of insulin polypeptide-oligomer conjugate is greater than about 90 percent.

64. The method of claim 1, wherein the yield of insulin polypeptide-oligomer conjugate is greater than 95 percent.

65. The method of claim 1, wherein the yield of insulin polypeptide-oligomer conjugate is greater than 99 percent.

66. A method of synthesizing an insulin molecule, comprising synthesizing an insulin polypeptide-oligomer conjugate according to claim 1 and hydrolyzing the oligomer(s) from the polypeptide-oligomer conjugate to yield the insulin molecule.

67. A method of synthesizing insulin, comprising synthesizing an insulin polypeptide-oligomer conjugate according to claim 1 and hydrolyzing the oligomer(s) from the polypeptide-oligomer conjugate to yield insulin.

68. A method of synthesizing an insulin polypeptide-oligomer conjugate comprising:
(a) contacting a proinsulin polypeptide comprising an insulin polypeptide coupled to one or more non-insulin polypeptides by peptide bond(s) capable of being cleaved to yield the insulin polypeptide with an oligomer comprising the structure of Formula I:

$$A\text{-}L_j\text{-}G_k\text{-}R\text{-}G'_m\text{-}R'\text{-}G''_n\text{-}T \qquad (I)$$

wherein:

A is an activatable moiety;

L is an optional linker moiety;

G, G' and G" are each optional spacer moieties;

R is a lipophilic moiety and R' is a polyalkylene glycol moiety, or R' is the lipophilic moiety and R is the polyalkylene glycol moiety, and wherein, (i) R and R' are both present, or (ii) R and G are absent and L is coupled to G' if present or to R' if G' is not present, or (iii) R' and G" are absent and T is coupled to G' if present or to R if G' is not present;

T is a terminating moiety; and j, k, m and n are individually 0 or 1;

under conditions sufficient to couple the oligomer to the insulin polypeptide portion of the proinsulin polypeptide and provide a proinsulin polypeptide-oligomer conjugate; and (b) cleaving the one or more non-insulin polypeptides from the proinsulin polypeptide-oligomer conjugate to provide the insulin polypeptide-oligomer conjugate.

69. The method of claim 68, wherein R and R' are both present.

70. The method of claim 68, wherein R and G are absent and L is coupled to G' if present or to R' if G' is not present.

71. The method of claim 70 wherein R' is a polyethylene glycol moiety.

72. The method of claim 68, wherein R' and G" are absent and T is coupled to G' if present or to R if G' is not present.

73. The method of claim 68, wherein A is selected from the group consisting of —C(O)—OH, C(S)—OH, —C(S)—SH, —OH, —SH, and NH$_2$.

74. The method of claim 68, wherein L is selected from the group consisting of alkyl moieties and fatty acid moieties.

75. The method of claim 68, wherein G, G' and G" are individually selected from the group consisting of sugar moieties, cholesterol, and glycerine moieties.

76. The method of claim 68, wherein T is selected from the group consisting of alkyl and alkoxy.

77. The method of claim 68, wherein:
A is a carboxylic acid moiety;
R is an alkyl moiety having between 3 and 8 carbon atoms;
R' is polyethylene glycol having between 4 and 10 polyethylene glycol subunits;
T is lower alkyl or lower alkoxy; and
j, k, m and n are 0.

78. The method of claim 68, wherein:
A is a carboxylic acid moiety;
R is an alkyl moiety having between 3 and 8 carbon atoms;
R' is polyethylene glycol having 7 polyethylene glycol subunits;
T is methoxy; and
j, k, m and n are 0.

79. A method of synthesizing an insulin polypeptide-oligomer conjugate comprising:
(a) contacting a proinsulin polypeptide comprising an insulin polypeptide coupled to one or more non-insulin polypeptides by peptide bond(s) capable of being cleaved to yield the insulin polypeptide with an oligomer comprising the structure of Formula II:

$$A\text{-}X(CH_2)_m Y(C_2H_4O)_n R \qquad (II)$$

wherein:
A is —C(O)—OH, C(S)—OH, —C(S)—SH, —OH, —SH, or NH$_2$;
X is an oxygen atom or a covalent bond, with the proviso that X is not an oxygen atom when A is —OH;
Y is an ester, an ether, a carbamate, a carbonate, or an amide bonding moiety;
m is between 0 and 30;
n is between 0 and 50;
m and n are not both 0; and
R is an alkyl moiety, a sugar moiety, cholesterol, adamantane, an alcohol moiety, or a fatty acid moiety;
under conditions sufficient to couple the oligomer to the insulin polypeptide portion of the proinsulin polypeptide and provide a proinsulin polypeptide-oligomer conjugate; and
(b) cleaving the one or more non-insulin polypeptides from the proinsulin polypeptide-oligomer conjugate to provide the insulin polypeptide-oligomer conjugate.

80. The method of claim 79, wherein m is between 3 and 16.
81. The method of claim 79, wherein m is between 4 and 14.
82. The method of claim 79, wherein m is between 5 and 10.
83. The method of claim 79, wherein n is between 3 and 18.
84. The method of claim 79, wherein n is between 4 and 14.
85. The method of claim 79, wherein n is between 5 and 10.
86. The method of claim 79, wherein R is lower alkyl.
87. The method of claim 79, wherein R is C1 to C3 alkyl.
88. The method of claim 79, wherein R is methyl.

89. A method of synthesizing an insulin polypeptide-oligomer conjugate comprising:
(a) contacting a proinsulin polypeptide comprising an insulin polypeptide coupled to one or more non-insulin polypeptides by peptide bond(s) capable of being cleaved to yield the insulin polypeptide with an oligomer comprising the structure of Formula III:

$$A\text{-}(CH_2)_m(OC_2H_4)_n OR \qquad (III)$$

wherein:
A is —C(O)—OH, C(S)—OH, —C(S)—SH, —OH, —SH, or NH$_2$;
m is between 0 and 25;
n is between 0 and 25;
m and n are not both 0; and
R is alkyl;
under conditions sufficient to couple the oligomer to the insulin polypeptide portion of the proinsulin polypeptide and provide a proinsulin polypeptide-oligomer conjugate; and
(b) cleaving the one or more non-insulin polypeptides from the proinsulin polypeptide-oligomer conjugate to provide the insulin polypeptide-oligomer conjugate.

90. The method of claim 89, wherein m is between 3 and 16.
91. The method of claim 89, wherein m is between 4 and 14.
92. The method of claim 89, wherein m is between 5 and 10.
93. The method of claim 89, wherein n is between 3 and 18.
94. The method of claim 89, wherein n is between 4 and 14.
95. The method of claim 89, wherein n is between 5 and 10.
96. The method of claim 89, wherein R is lower alkyl.
97. The method of claim 89, wherein R is $C_1$ to $C_3$ alkyl.
98. The method of claim 89, wherein R is methyl.

99. A method of synthesizing an insulin polypeptide-oligomer conjugate comprising:
(a) contacting a proinsulin polypeptide comprising an insulin polypeptide having an A-chain polypeptide and a B-chain polypeptide, which comprises a lysine residue; a connecting peptide coupled at a first end to the C-terminus of the B-chain polypeptide and coupled at a second end to the N-terminus of the A-chain polypeptide; and a leader peptide coupled to the N-terminus of the B-chain polypeptide with an oligomer comprising the structure of Formula IV:

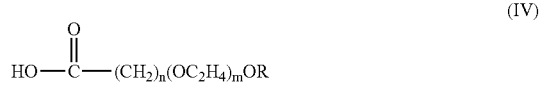

(IV)

wherein:
m is between 0 and 30.
n is between 0 and 50.
m and n are not both 0; and
R is alkyl;
under conditions sufficient to couple the oligomer to the lysine residue of the B-chain polypeptide of the insulin polypeptide portion of the proinsulin polypeptide and provide a proinsulin polypeptide-oligomer conjugate; and
(b) enzymatically cleaving the connecting peptide and the leader peptide from the proinsulin polypeptide-oligomer conjugate to provide the insulin polypeptide-oligomer conjugate.

100. The method of claim 99, wherein m is between 3 and 16.

101. The method of claim 99, wherein m is between 4 and 14.

102. The method of claim 99, wherein m is between 5 and 10.

103. The method of claim 99, wherein n is between 3 and 18.

104. The method of claim 99, wherein n is between 4 and 14.

105. The method of claim 99, wherein n is between 5 and 10.

106. The method of claim 99, wherein R is lower alkyl.

107. The method of claim 99, wherein R is $C_1$ to $C_3$ alkyl.

108. The method of claim 99, wherein R is methyl.

109. A method of synthesizing an insulin-oligomer conjugate comprising:
(a) contacting a proinsulin polypeptide, which comprises proinsulin coupled at its N-terminus to a leader peptide, with an oligomer comprising the structure of Formula V:

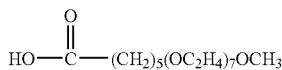

(V)

under conditions sufficient to couple the oligomer to the B29 lysine residue of the proinsulin and provide a proinsulin polypeptide-oligomer conjugate; and
(b) enzymatically cleaving the C-peptide and the leader peptide from the proinsulin polypeptide-oligomer conjugate to provide the insulin-oligomer conjugate.

110. The method of claim 109, wherein the enzymatically cleaving of the C-peptide and the leader peptide from the proinsulin polypeptide-oligomer conjugate comprises:
(a) contacting the proinsulin polypeptide-oligomer conjugate with a first enzyme under conditions sufficient to provide an $(Arg^{31})$-insulin-oligomer conjugate; and
(b) contacting the $(Arg^3)$-insulin polypeptide-oligomer conjugate with a second enzyme under conditions sufficient to provide the insulin polypeptide-oligomer conjugate.

111. The method of claim 110, wherein the first enzyme is trypsin.

112. The method of claim 110, wherein the second enzyme is carboxy peptidase B.

113. A method of synthesizing an insulin polypeptide-acyl oligomer conjugate comprising enzymatically cleaving one or more non-insulin polypeptides from a proinsulin polypeptide-acyl oligomer conjugate to provide the insulin polypeptide-acyl oligomer conjugate.

114. A method of synthesizing an insulin-acyl oligomer conjugate comprising enzymatically cleaving a leader peptide and a C-peptide from a proinsulin polypeptide-acyl oligomer conjugate comprising the following structure:

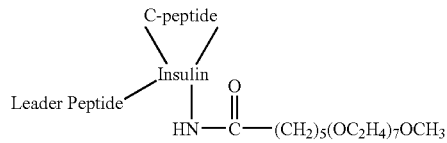

to provide the insulin-acyl oligomer conjugate comprising the following structure:

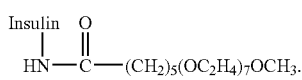

115. The method of claim 114, wherein the leader peptide is devoid of lysine residues.

116. The method of claim 114, wherein the enzymatically cleaving of the C-peptide and the leader peptide from the proinsulin polypeptide-acyl oligomer conjugate comprises:
(a) contacting the proinsulin polypeptide-oligomer conjugate with a first enzyme under conditions sufficient to provide a $(Arg^{31})$-insulin-oligomer conjugate; and
(b) contacting the $(Arg^{31})$-insulin polypeptide-oligomer conjugate with a second enzyme under conditions sufficient to provide the insulin polypeptide-oligomer conjugate.

117. The method of claim 116, wherein the first enzyme is trypsin.

118. The method of claim 116, wherein the second enzyme is carboxy peptidase B.

119. A method of synthesizing a proinsulin polypeptide-oligomer conjugate comprising contacting a proinsulin polypeptide with an oligomer comprising a hydrophilic moiety and a lipophilic moiety under conditions sufficient to provide the proinsulin polypeptide-oligomer conjugate.

120. A method of synthesizing a C-peptide polypeptide-oligomer conjugate comprising:
(a) contacting a pro-C-peptide polypeptide comprising a C-peptide polypeptide coupled to one or more non-insulin polypeptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate; and
(b) cleaving the one or more non-insulin polypeptides from the pro-C-peptide polypeptide-oligomer conjugate to provide the C-peptide polypeptide-oligomer conjugate.

121. The method of claim 120, wherein the C-peptide polypeptide is C-peptide.

122. The method of claim 120, wherein the pro-C-peptide polypeptide is a proinsulin polypeptide.

123. The method of claim 120, wherein the pro-C-peptide polypeptide is proinsulin.

124. The method of claim 1, wherein the proinsulin polypeptide is B-chain-Mg-A-chain.

125. The method of claim 1, wherein the proinsulin polypeptide is His-Gly-Arg-B-chain-Arg-A-chain.

126. The method of claim 1, wherein the proinsulin polypeptide is His-Gly-Mg-B-chain-Mg-Mg-A-chain.

127. The method of claim 1, wherein the proinsulin polypeptide is Leader peptide-Arg-B-chain-Arg-Pro-Arg-A-chain.

128. The method of claim 1, wherein the proinsulin polypeptide is Leader peptide-Arg-B-chain-Arg-Pro-Arg-A-chain.

129. The method of claim 1, wherein the proinsulin polypeptide is B-chain-Arg-Arg-A-chain.

130. The method of claim 1, wherein the oligomer comprises a $C_2$ to $C_{18}$ aryl group.

131. The method of claim 1, wherein the proinsulin polypeptide-oligomer conjugate comprises a LysB29 palmitoyl.

132. The method of claim 1, wherein the oligomer is a LysB29 $C_2$ to $C_{18}$ aryl group.

* * * * *

UNITED STATES PATENT AND TRADEMARK OFFICE
CERTIFICATE OF CORRECTION

PATENT NO.       : 7,166,571 B2
APPLICATION NO.  : 10/382022
DATED            : January 23, 2007
INVENTOR(S)      : Soltero et al.

It is certified that error appears in the above-identified patent and that said Letters Patent is hereby corrected as shown below:

Column 8, Line 45: "$\pm 11$" should be --$\pm 1$--.

Column 67, Line 65: "hexnoic acid" should be --hexanoic acid--

Column 68, Line 17: "ethoxy }-hexanoic acid" should be --ethoxy}-ethoxy)-hexanoic acid--

Column 68, Line 29: "ethoxy }-hexanoic acid" should be --ethoxy}-ethoxy)-hexanoic acid--

Column 89, Line 9: "$Lys_{B29}$" should be --LysB29--

Column 93, Line 42: "$LysB_{29}$" should be --LysB29--

Column 95, Line 4: "$Lys_{B29}$" should be --LysB29--

Column 95, Line 29: "$Lys_{64}$" should be --Lys64--

Column 95, Line 61: "$Lys_{64}$" should be --Lys64--

Column 96, Line 23: "$Lys_{B29}$" should be --LysB29--

Column 97, Line 7: "$LysB_{29}$" should be --LysB29--

Column 97, Line 37: "$Ly_{SB29}$" should be --LysB29--

Column 97, Line 38: "$Ly_{SB29}$" should be --LysB29--

Column 97, Line 44: "$LysB_{29}$" should be --LysB29--

Column 98, Line 29: "$Ly_{SB29}$" should be --LysB29--

Column 99, Line 34: "$Ly_{SB29}$" should be --LysB29--

Column 103, Line 21: "step 0" should be --step (a)--

Column 104, Line 42: "$Pro_{B29}$" should be --Pro$^{B29}$--

Column 106, Line 34: "Rand G" should be --R and G--

UNITED STATES PATENT AND TRADEMARK OFFICE
CERTIFICATE OF CORRECTION

PATENT NO. : 7,166,571 B2
APPLICATION NO. : 10/382022
DATED : January 23, 2007
INVENTOR(S) : Soltero et al.

It is certified that error appears in the above-identified patent and that said Letters Patent is hereby corrected as shown below:

Column 110, Line 45: "chain-Mg-A" should be --chain-Arg-A--

Column 110, Line 49: "Gly-Mg-B-Chain-Mg-Mg-A" should be --Gly-Arg-B-Chain-Arg-Arg-A--

Signed and Sealed this

Thirtieth Day of October, 2007

JON W. DUDAS
*Director of the United States Patent and Trademark Office*